(12) United States Patent
Stefanchik et al.

(10) Patent No.: US 9,211,159 B2
(45) Date of Patent: Dec. 15, 2015

(54) SURGICAL DEVICES WITH INTRACORPOREAL ELBOW JOINT

(75) Inventors: David Stefanchik, Morrow, OH (US); Omar J. Vakharia, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1047 days.

(21) Appl. No.: 13/309,856

(22) Filed: Dec. 2, 2011

(65) Prior Publication Data
US 2013/0144306 A1    Jun. 6, 2013

(51) Int. Cl.
*A61B 17/00* (2006.01)
*A61B 19/00* (2006.01)
*A61B 17/29* (2006.01)

(52) U.S. Cl.
CPC ......... *A61B 19/22* (2013.01); *A61B 17/29* (2013.01); *A61B 19/26* (2013.01); *A61B 2017/003* (2013.01); *A61B 2017/00738* (2013.01); *A61B 2017/291* (2013.01); *A61B 2017/2902* (2013.01); *A61B 2017/2927* (2013.01); *A61B 2019/2242* (2013.01)

(58) Field of Classification Search
CPC ........... A61B 2019/2242; A61B 19/22; A61B 19/2203; A61B 2017/2927; A61B 17/29
USPC ................................. 606/205, 206
See application file for complete search history.

(56) References Cited

U.S. PATENT DOCUMENTS

| | | |
|---|---|---|
| 4,394,864 A | 7/1983 | Sandhaus |
| 4,527,562 A | 7/1985 | Mericle |
| 4,579,118 A | 4/1986 | Failla |
| 4,762,455 A | 8/1988 | Coughlan et al. |
| 5,062,846 A | 11/1991 | Oh et al. |
| 5,330,502 A | 7/1994 | Hassler et al. |
| 5,449,374 A | 9/1995 | Dunn et al. |
| 5,464,416 A | 11/1995 | Steckel |
| 5,573,546 A | 11/1996 | Nakao |

(Continued)

FOREIGN PATENT DOCUMENTS

| | | |
|---|---|---|
| FR | 2845889 A1 | 4/2004 |
| GB | 2284242 A | 5/1995 |

(Continued)

OTHER PUBLICATIONS

Serway et al. "Physics for Scientists and Engineers vol. 1", 2004, Thomson/Brooks/Cole, 6th edition, pp. 293-295 and 298.

(Continued)

*Primary Examiner* — Victor Nguyen
*Assistant Examiner* — Kevin Everage
(74) *Attorney, Agent, or Firm* — Nutter McClennen & Fish LLP

(57) ABSTRACT

Surgical devices are disclosed herein that generally include an intracorporeal elbow joint to facilitate translational movement of an end effector while allowing a body portion of the surgical device and a trocar or working channel through which the device is inserted to be maintained in a fixed angular orientation relative to the patient. This allows a plurality of such devices to be used effectively with a single incision or access device. Such devices also generally provide end effector movement with six degrees of freedom, while maintaining a mechanical linkage between the user and the end effector and while mimicking and/or mirroring natural user movement. Various methods related to such devices are also disclosed.

40 Claims, 43 Drawing Sheets

(56) References Cited

U.S. PATENT DOCUMENTS

| | | | |
|---|---|---|---|
| 5,697,939 | A | 12/1997 | Kubota et al. |
| 5,702,408 | A | 12/1997 | Wales et al. |
| 5,792,135 | A | 8/1998 | Madhani et al. |
| 5,951,574 | A | 9/1999 | Stefanchik et al. |
| 6,120,433 | A | 9/2000 | Mizuno et al. |
| 6,197,017 | B1 | 3/2001 | Brock et al. |
| 6,364,888 | B1 | 4/2002 | Niemeyer et al. |
| 6,391,035 | B1 | 5/2002 | Appleby et al. |
| 7,398,707 | B2 | 7/2008 | Morley et al. |
| 7,689,320 | B2 | 3/2010 | Prisco et al. |
| 7,775,972 | B2 | 8/2010 | Brock et al. |
| 7,947,035 | B2 | 5/2011 | Miyamoto et al. |
| 8,007,511 | B2 | 8/2011 | Brock et al. |
| 8,083,667 | B2 | 12/2011 | Cooper et al. |
| 8,617,203 | B2 | 12/2013 | Stefanchik et al. |
| 2004/0236316 | A1 | 11/2004 | Danitz et al. |
| 2005/0096694 | A1* | 5/2005 | Lee .................. 606/205 |
| 2005/0204851 | A1 | 9/2005 | Morley et al. |
| 2007/0066986 | A1 | 3/2007 | Sanchez |
| 2007/0239203 | A1 | 10/2007 | Cooper et al. |
| 2008/0046000 | A1 | 2/2008 | Lee et al. |
| 2008/0065098 | A1* | 3/2008 | Larkin .................. 606/130 |
| 2008/0065108 | A1 | 3/2008 | Diolaiti |
| 2008/0255608 | A1 | 10/2008 | Hinman et al. |
| 2009/0287351 | A1 | 11/2009 | Howison et al. |
| 2010/0004663 | A1* | 1/2010 | Murphy et al. .......... 606/130 |
| 2010/0185212 | A1 | 7/2010 | Sholev |
| 2010/0225209 | A1 | 9/2010 | Goldberg et al. |
| 2011/0028793 | A1 | 2/2011 | Martin et al. |
| 2011/0118709 | A1 | 5/2011 | Burbank |
| 2012/0095298 | A1 | 4/2012 | Stefanchik et al. |
| 2012/0158013 | A1 | 6/2012 | Stefanchik et al. |
| 2012/0158014 | A1 | 6/2012 | Stefanchik et al. |
| 2013/0140835 | A1 | 6/2013 | Stefanchik et al. |
| 2013/0144274 | A1 | 6/2013 | Stefanchik et al. |
| 2013/0144395 | A1 | 6/2013 | Stefanchik et al. |

FOREIGN PATENT DOCUMENTS

| | | |
|---|---|---|
| WO | 03/086219 A2 | 10/2003 |
| WO | 2009/126955 A2 | 10/2009 |
| WO | 2010/030114 A2 | 3/2010 |

OTHER PUBLICATIONS

International Search Report and Written Opinion for Application No. PCT/US2012/066954, issued Jun. 18, 2013. (14 pages).

FlexDex: A Minimally Invasive Surgical Tool with Enhanced Dexterity and Intuitive Control, Awtar et al., Journal of Medical Devices, Sep. 2010, vol. 4.

Robot Technology, vol. 3A: Teleoperations and Robotics: Evolution and Development, p. 55, 1987.

Robot Technology, vol. 3A: Teleoperations and Robotics: Evolution and Development, pp. 67-93, 1984.

Robot Technology, vol. 3A: Teleoperations and Robotics: Evolution and Development, pp. cover, 24, 25, 54, 60, 61, 68, 69, 92, and 93, 1984.

* cited by examiner

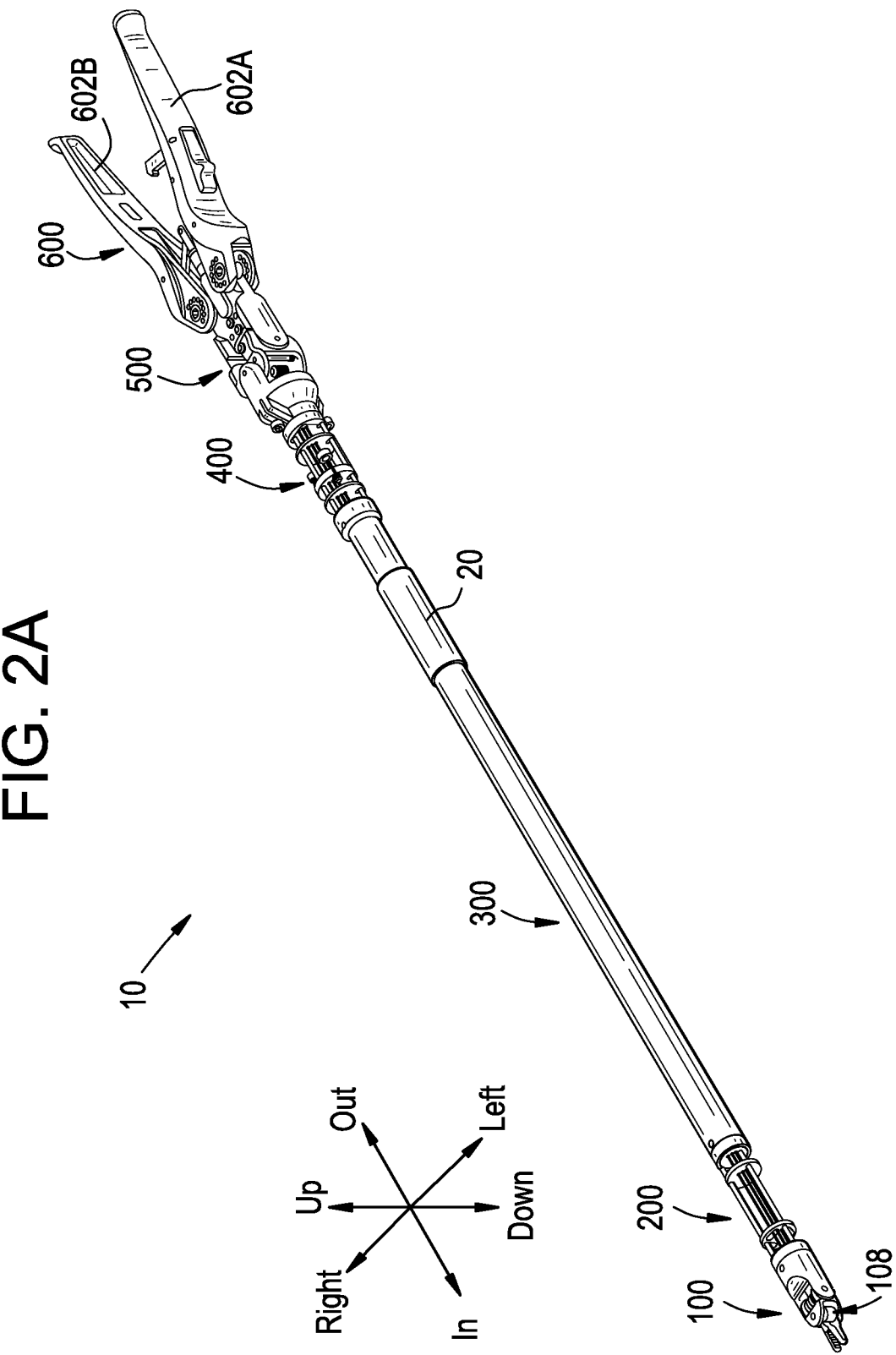

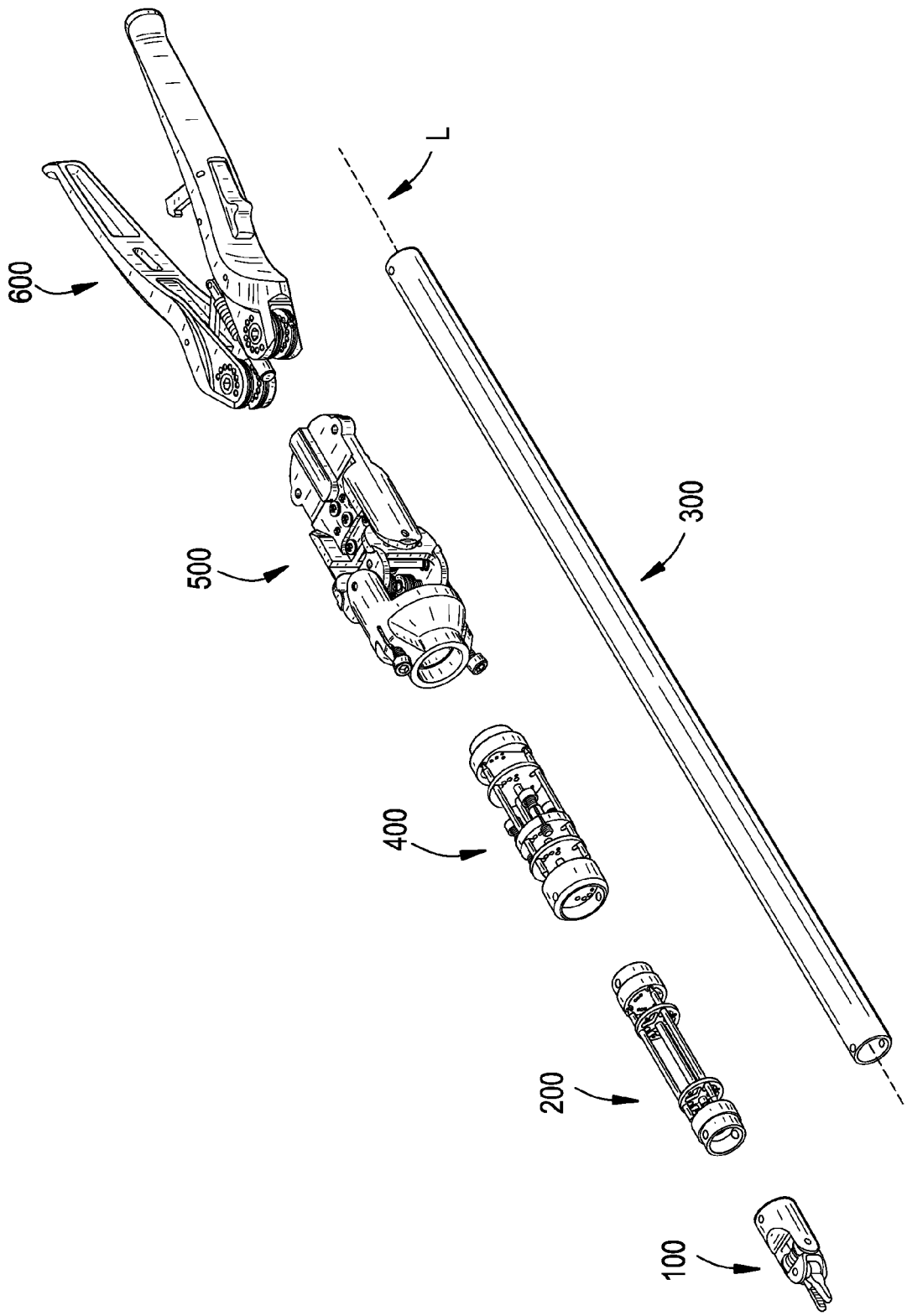

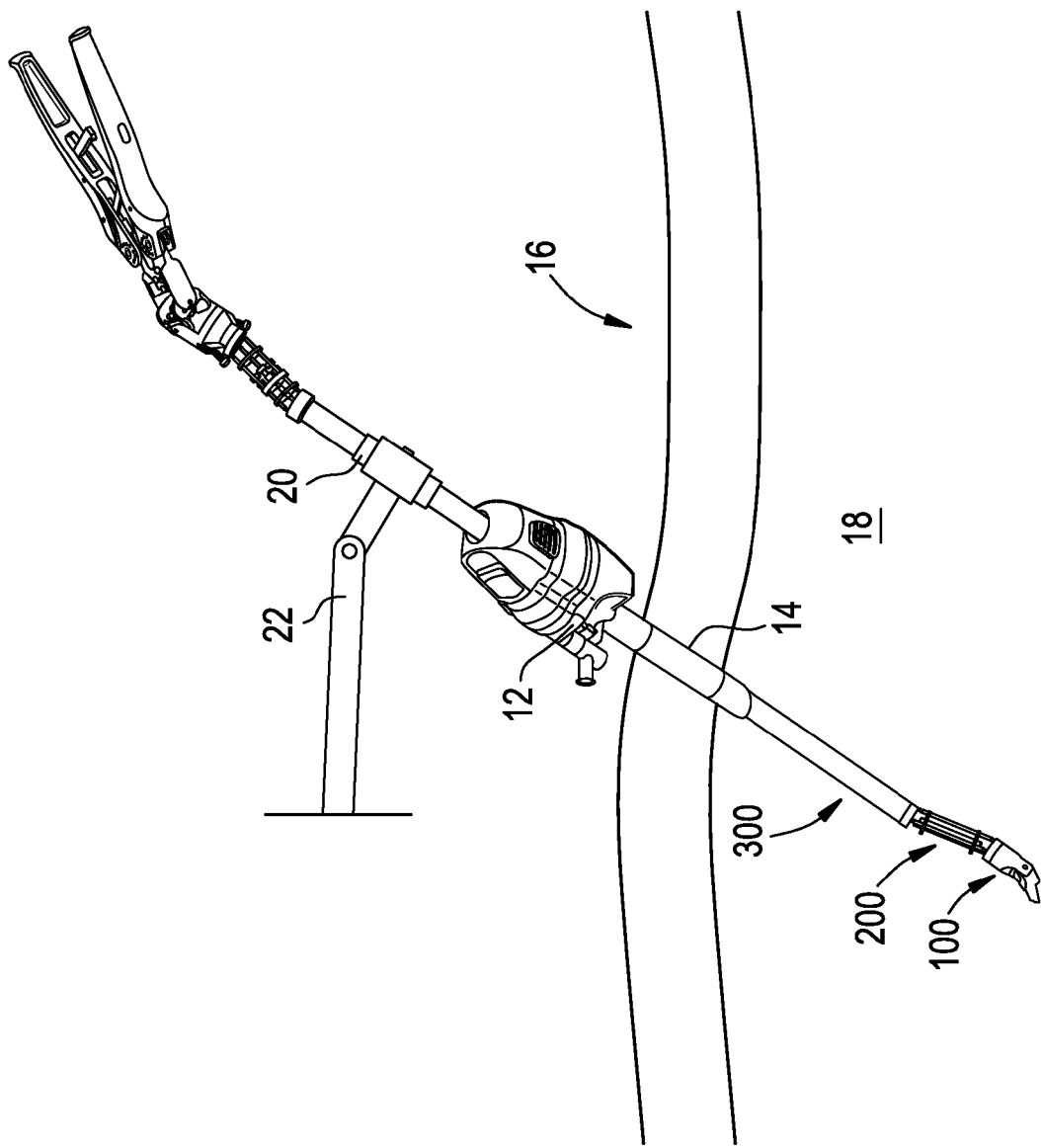

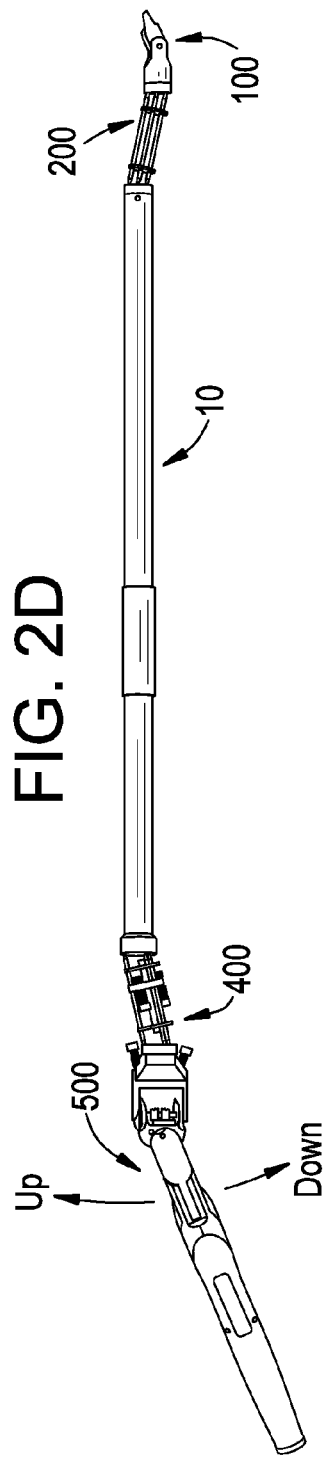
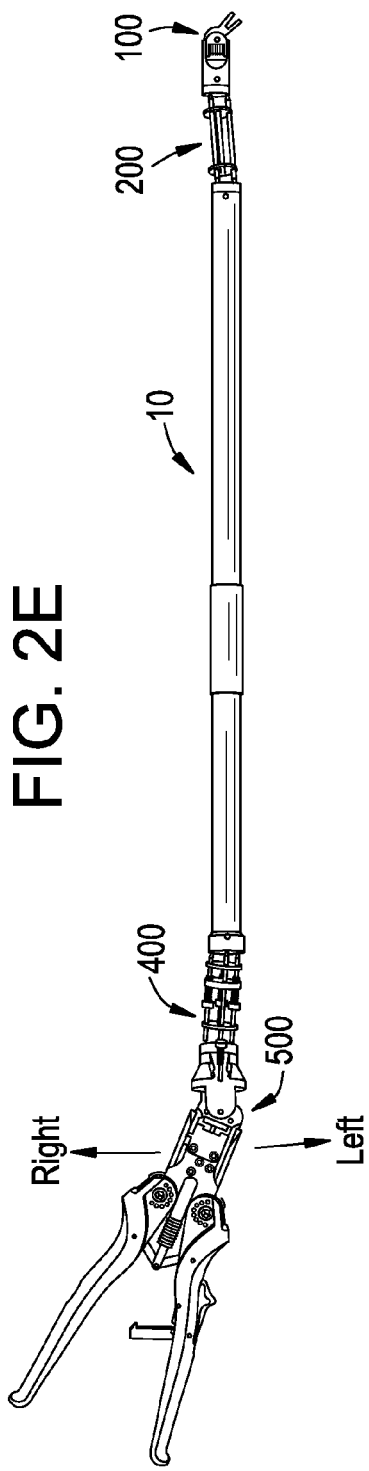
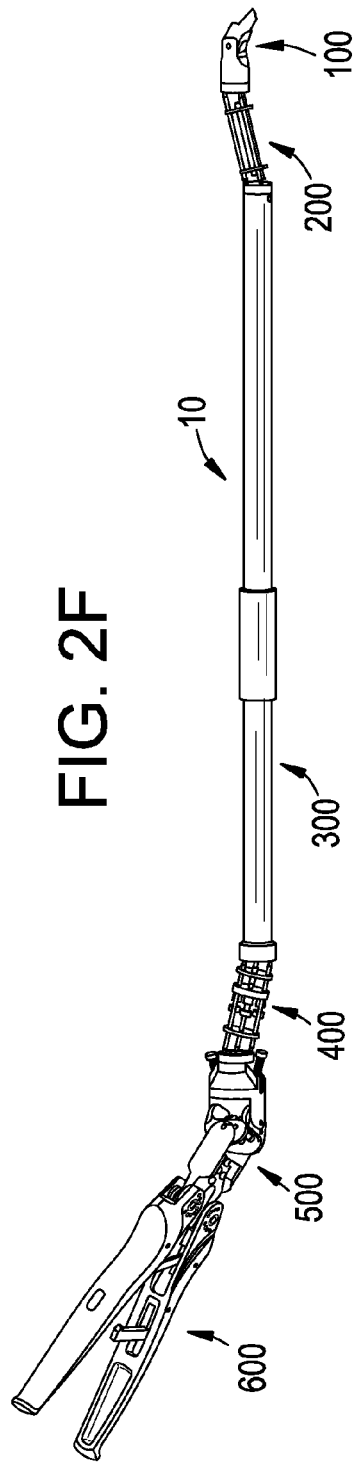
FIG. 2D
FIG. 2E
FIG. 2F

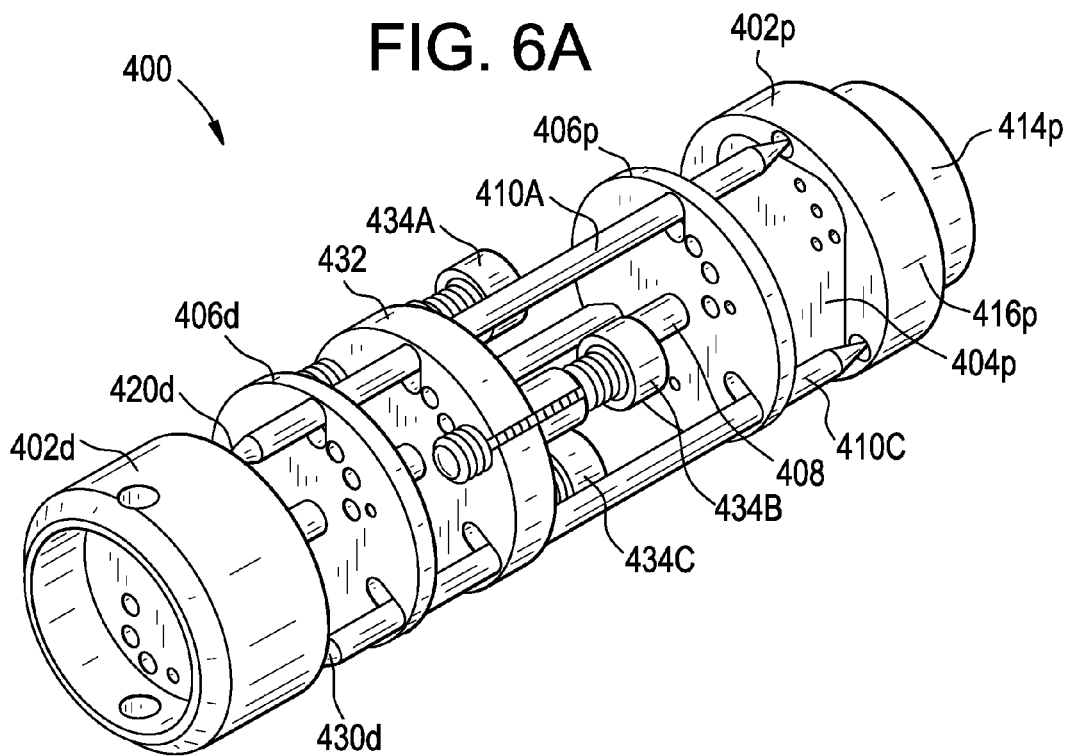
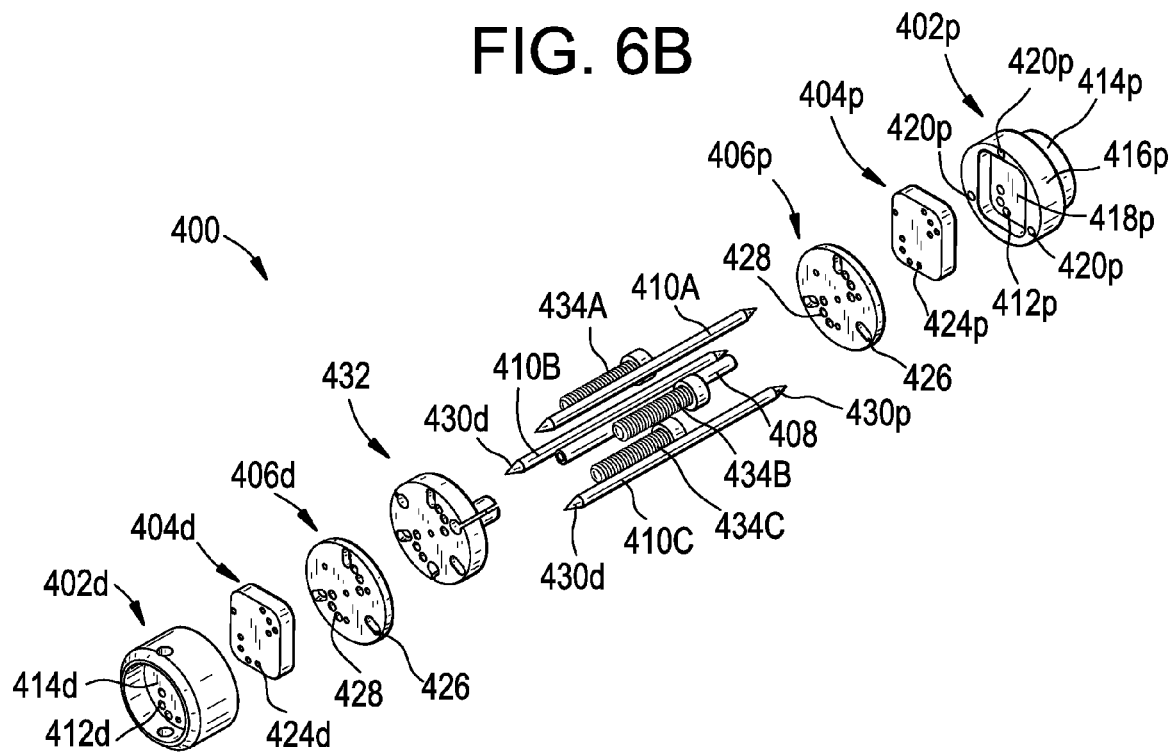

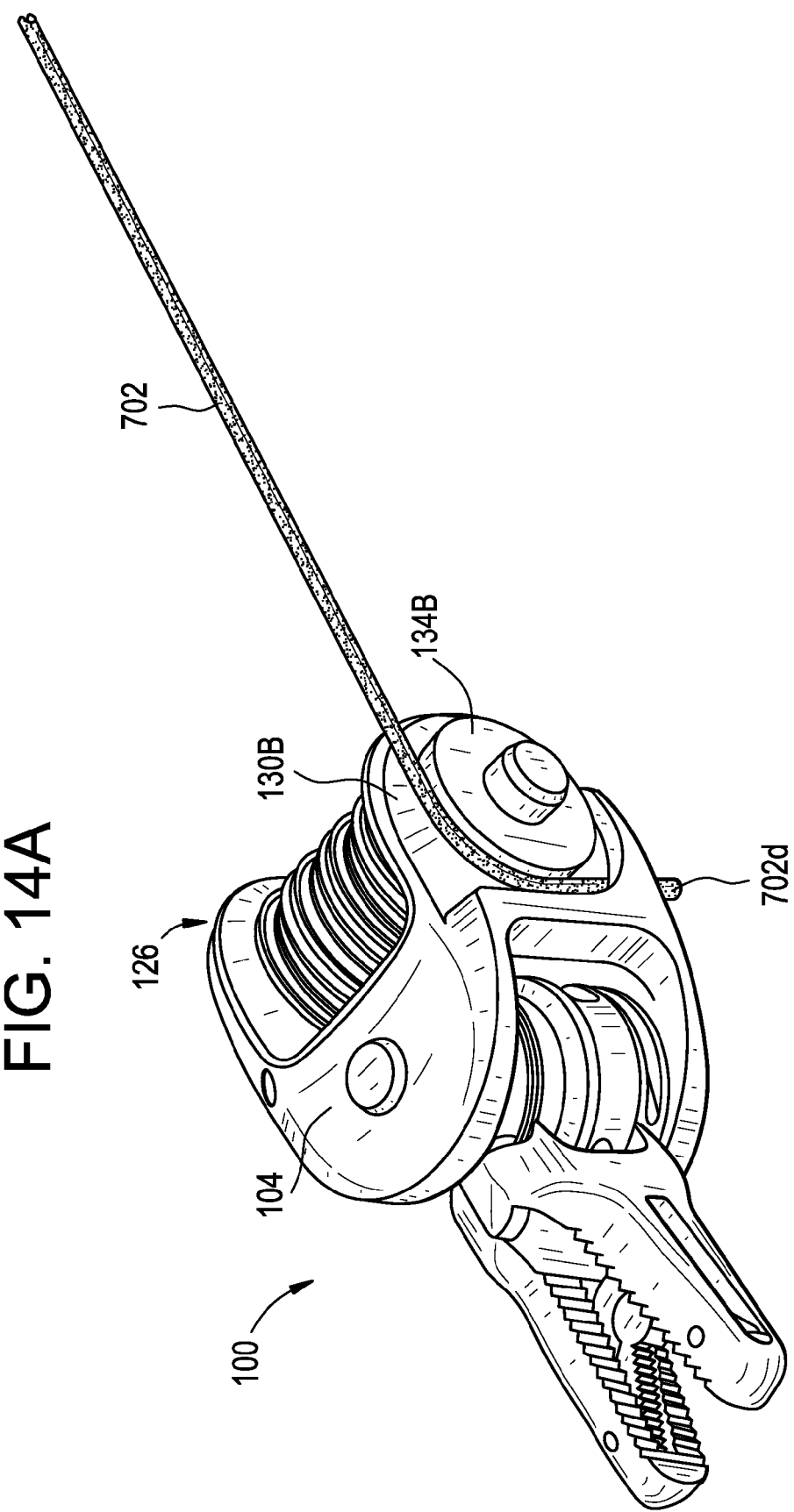

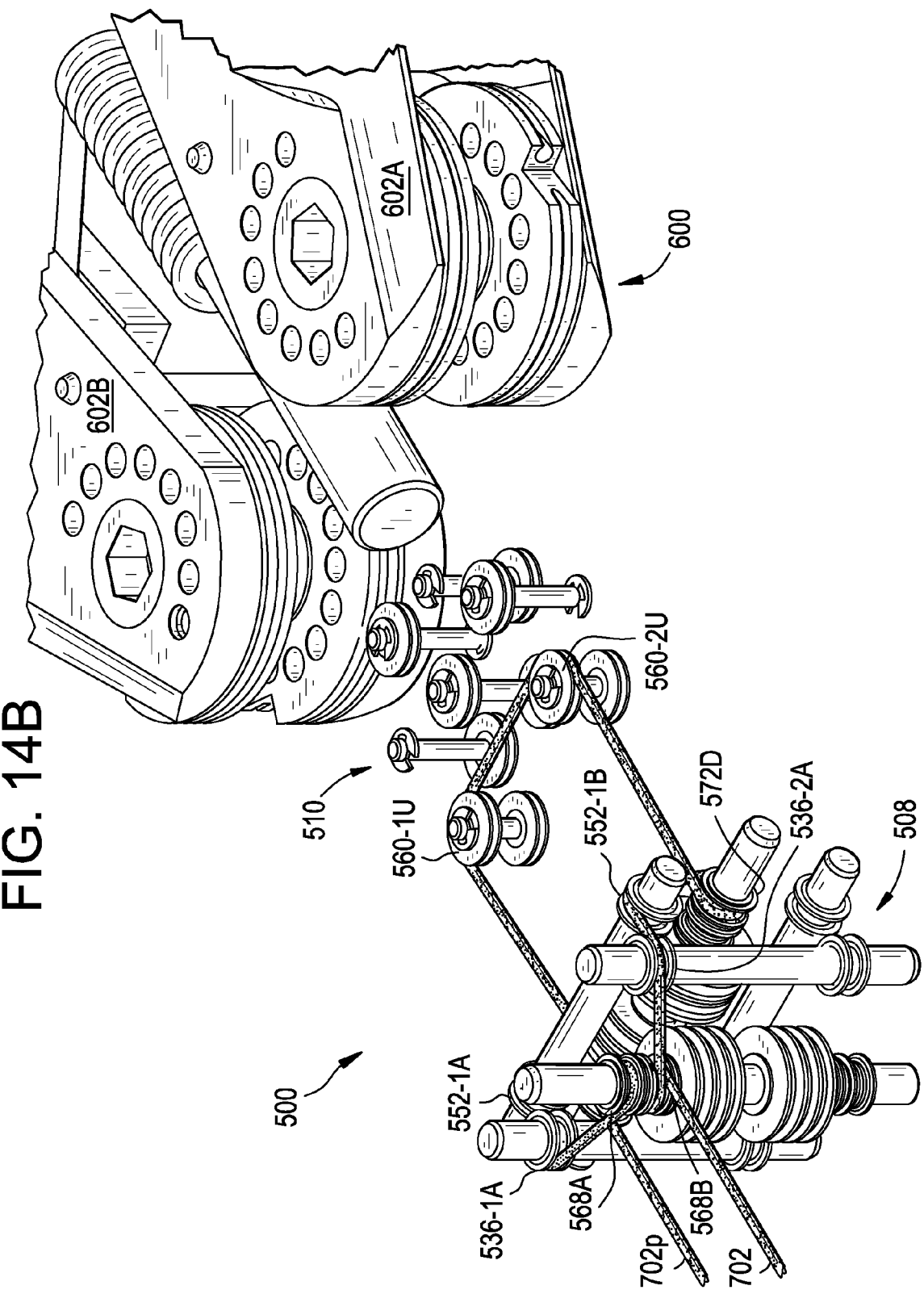

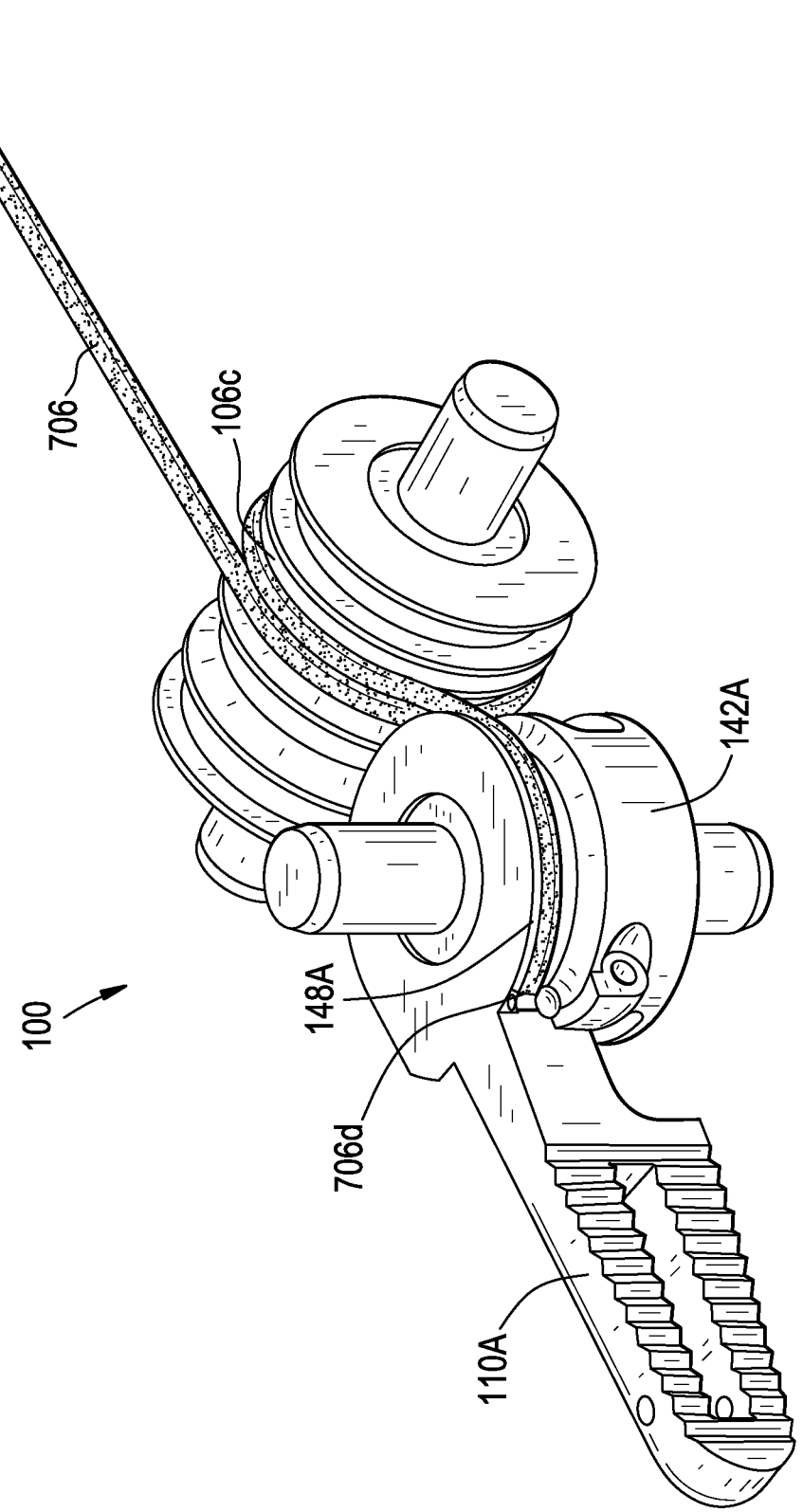

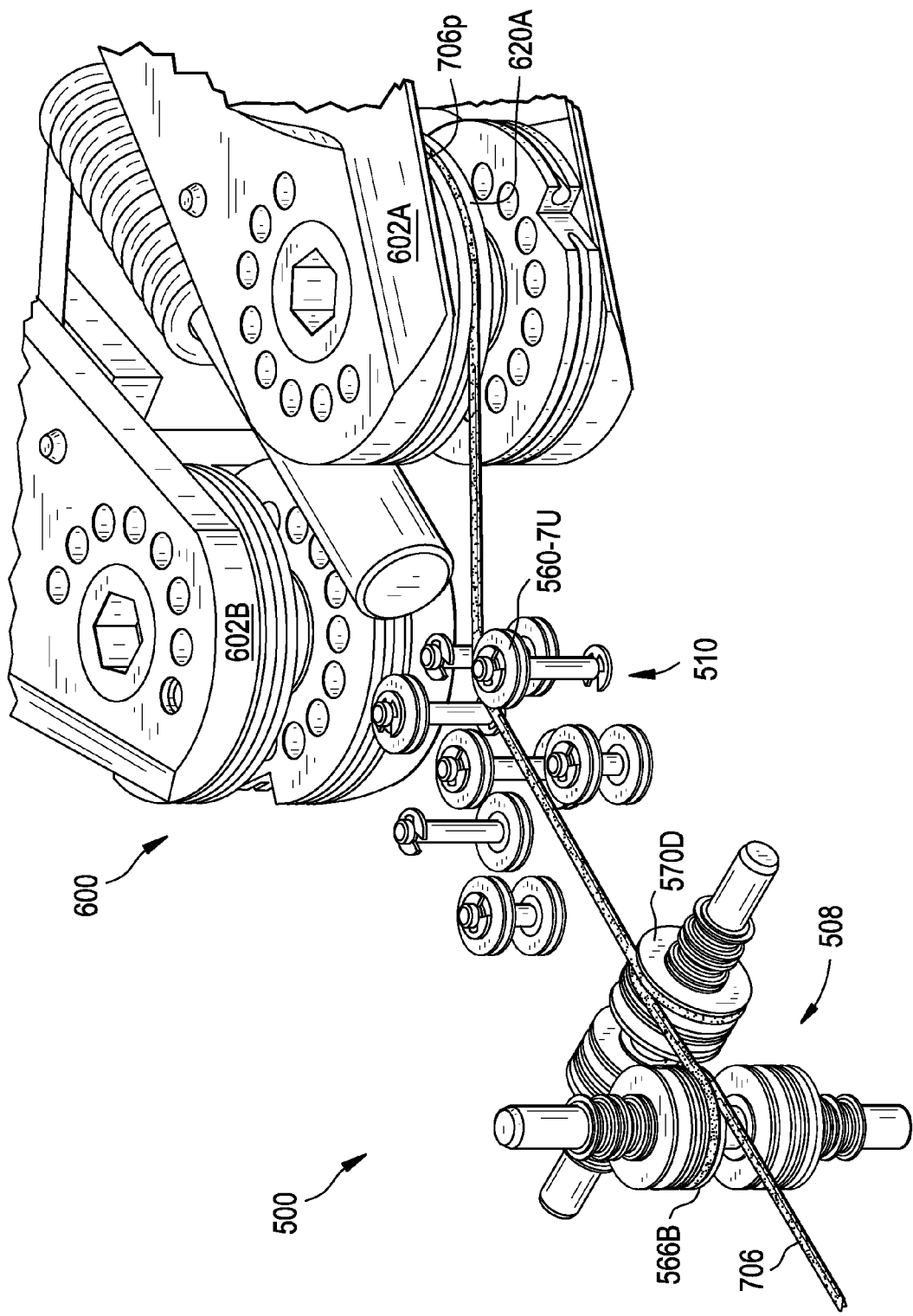

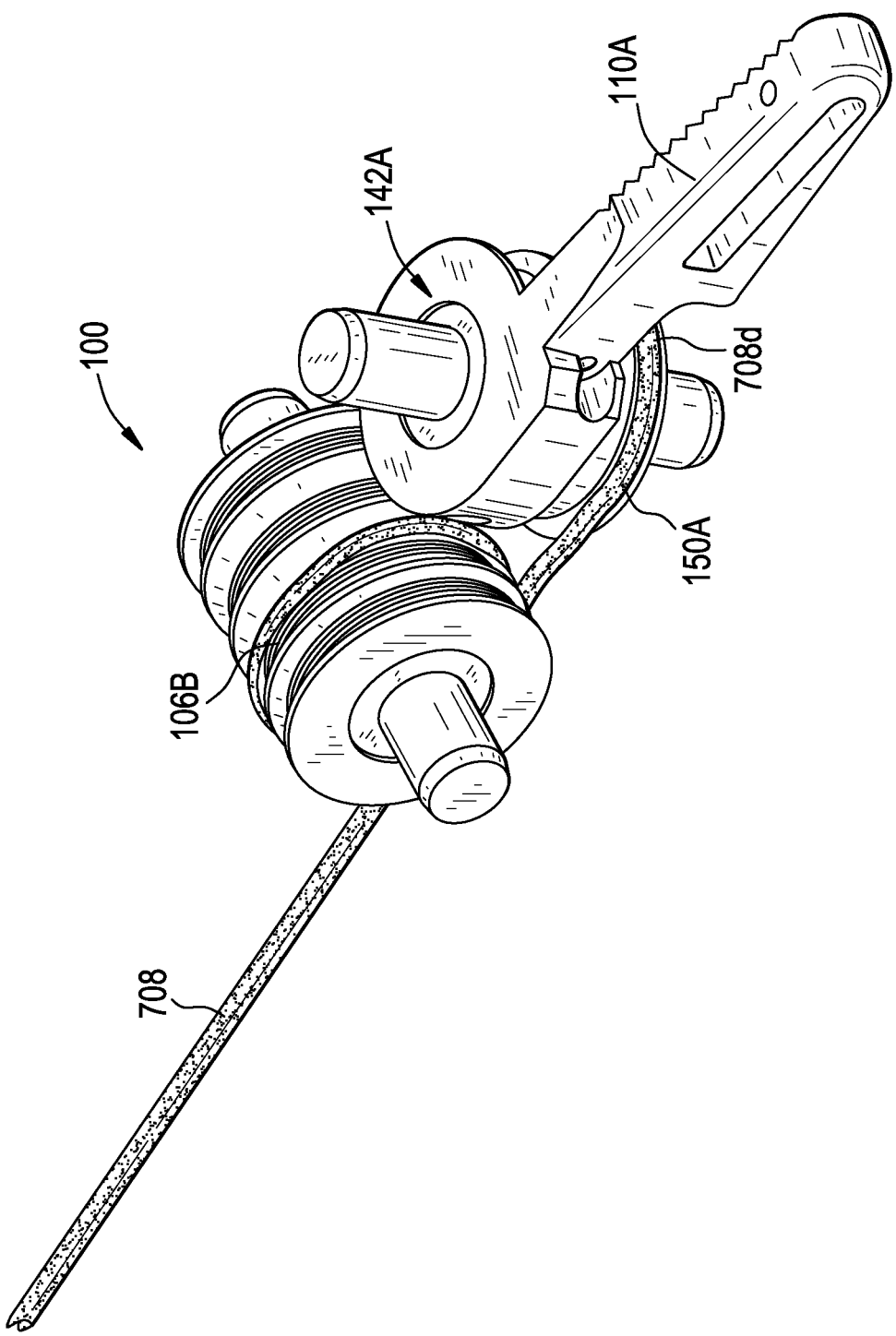

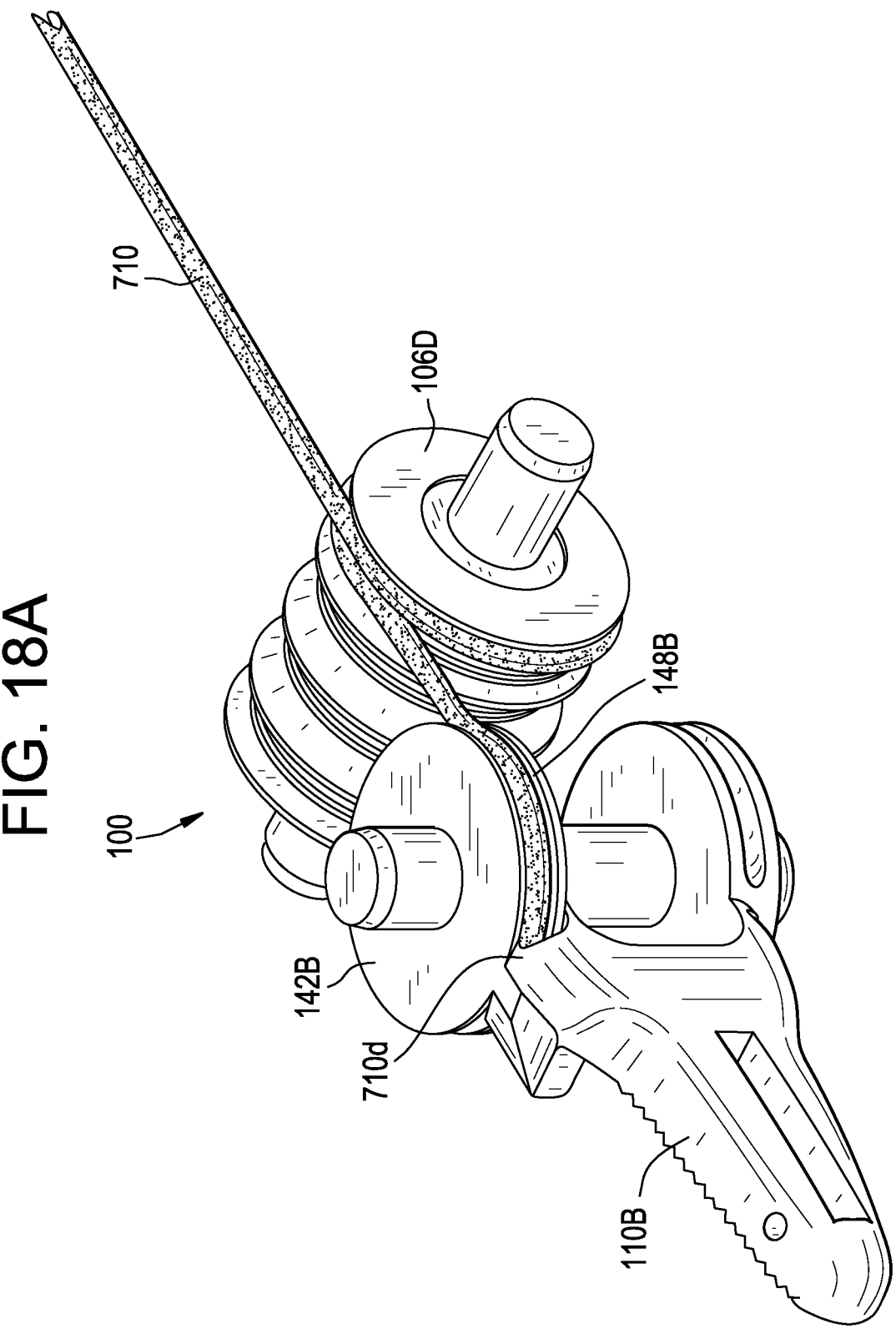

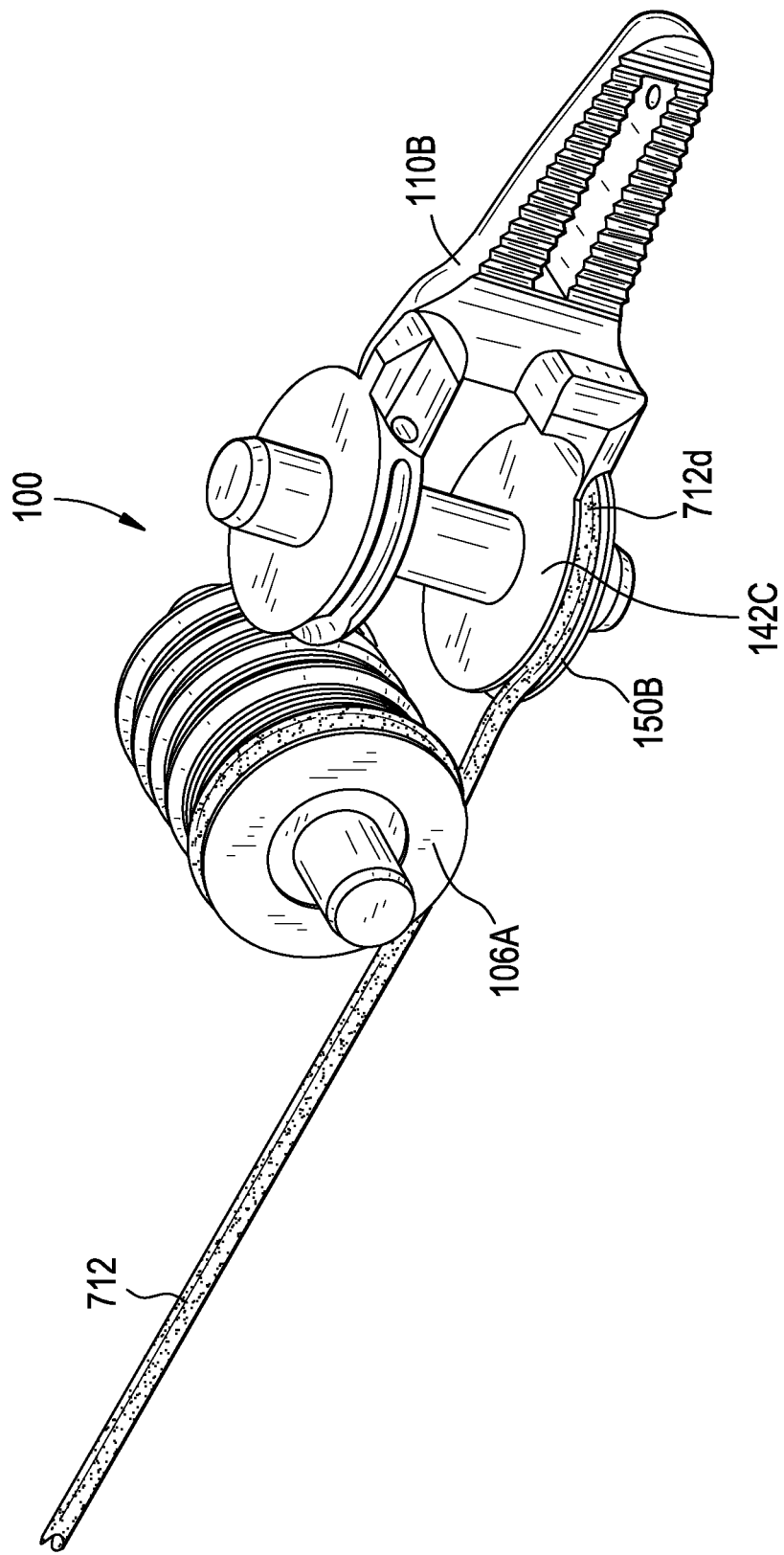

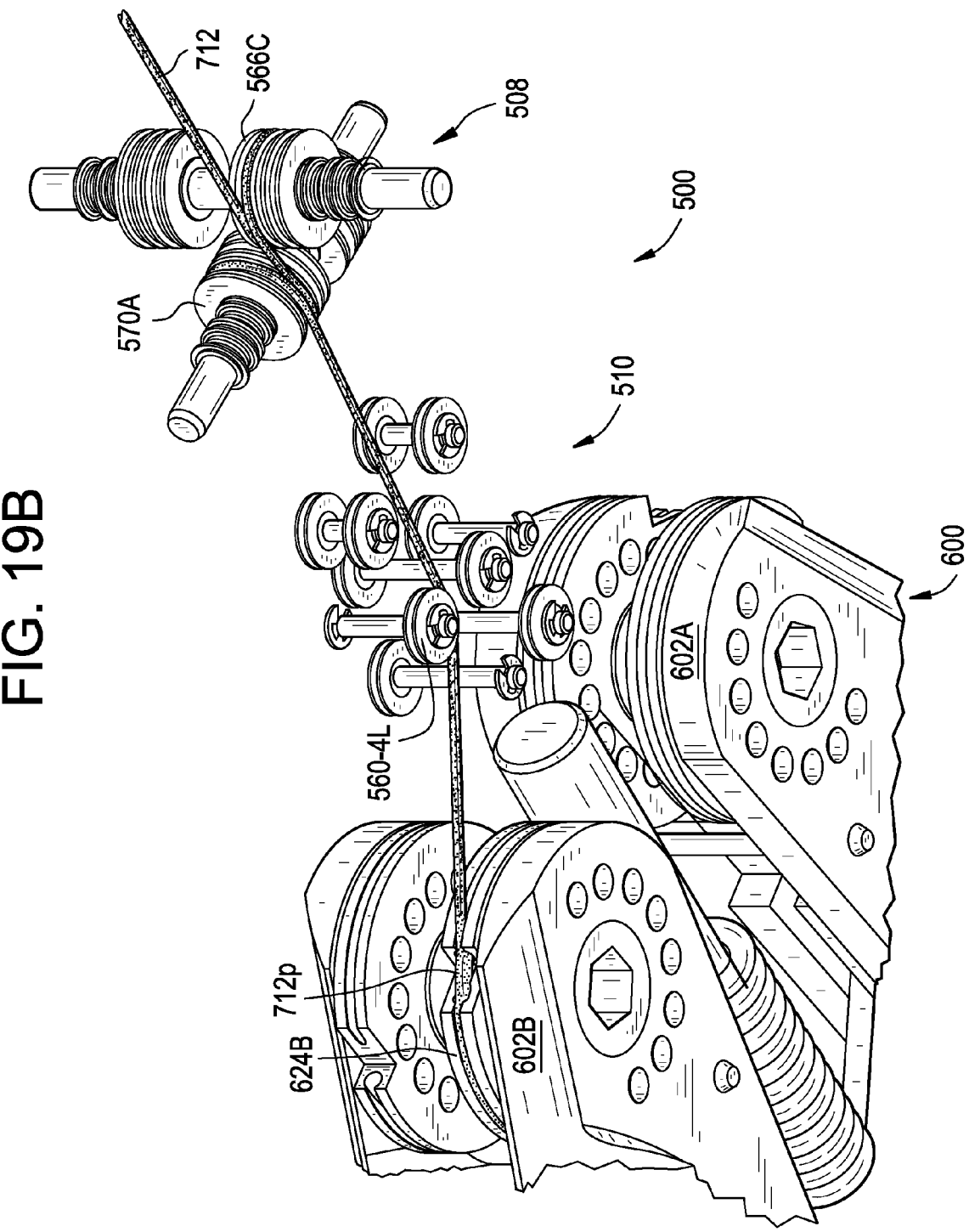

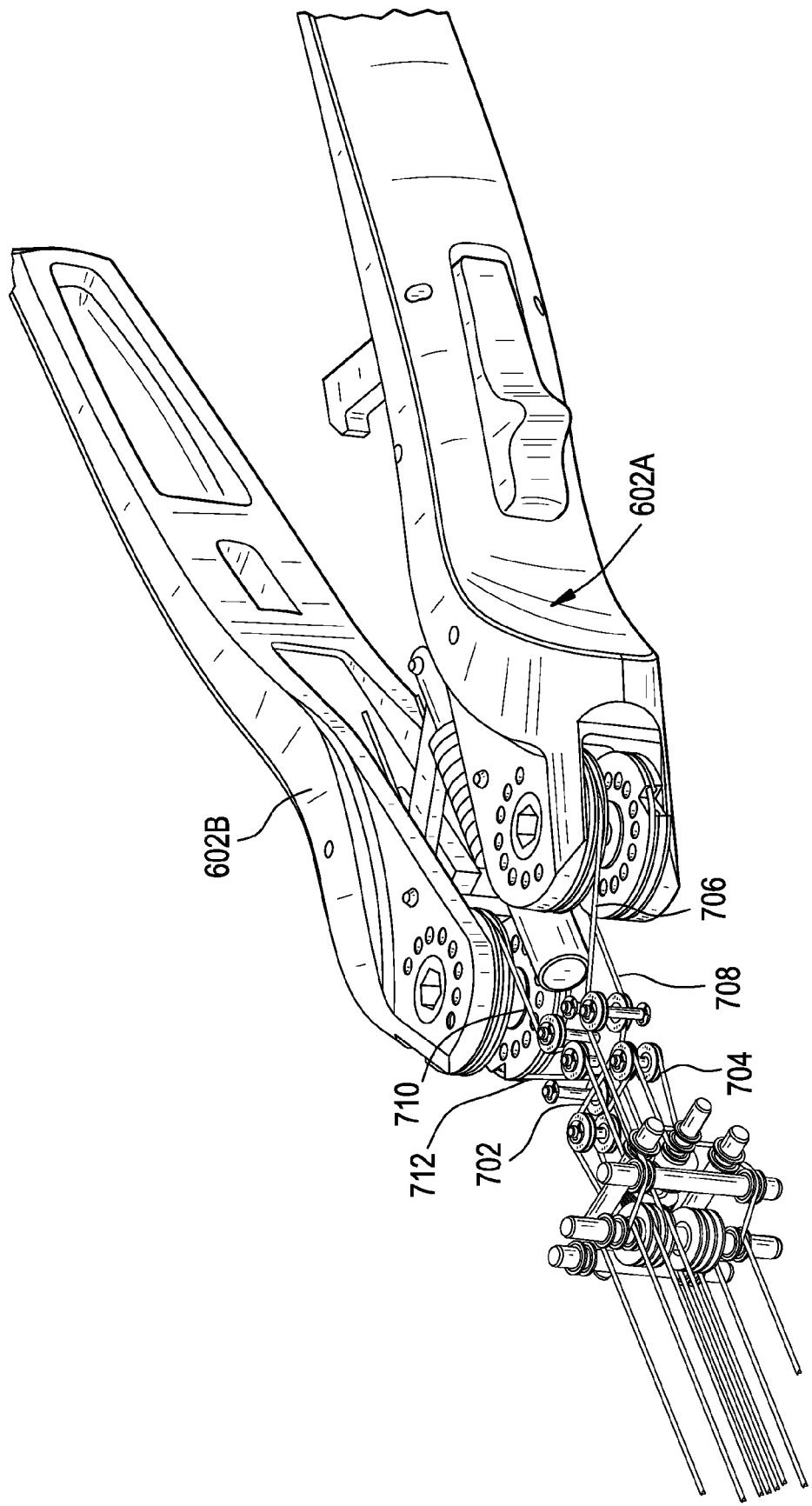

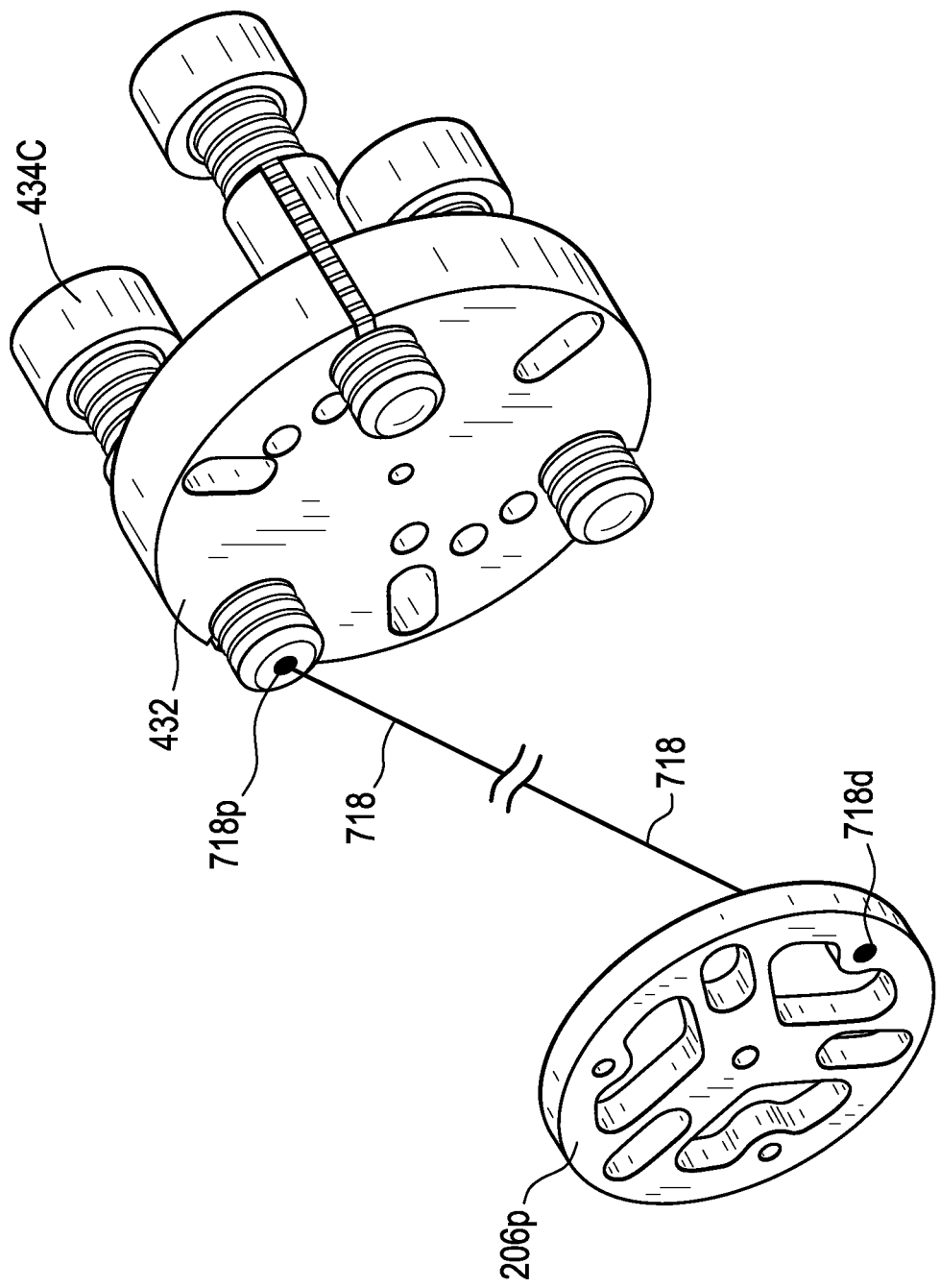

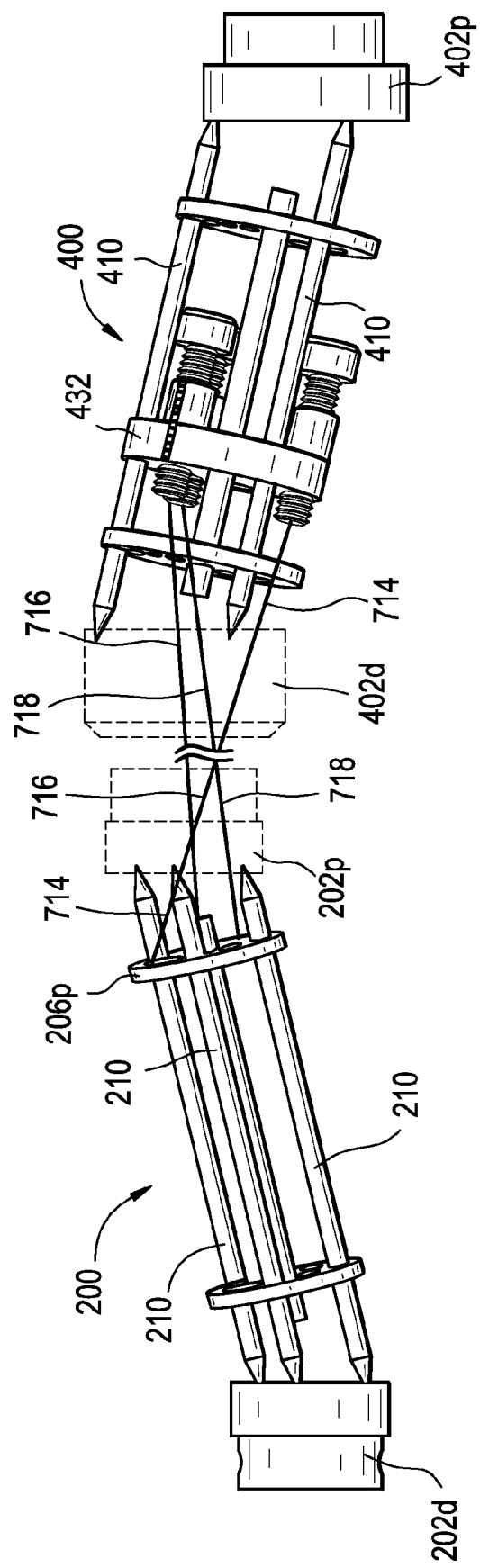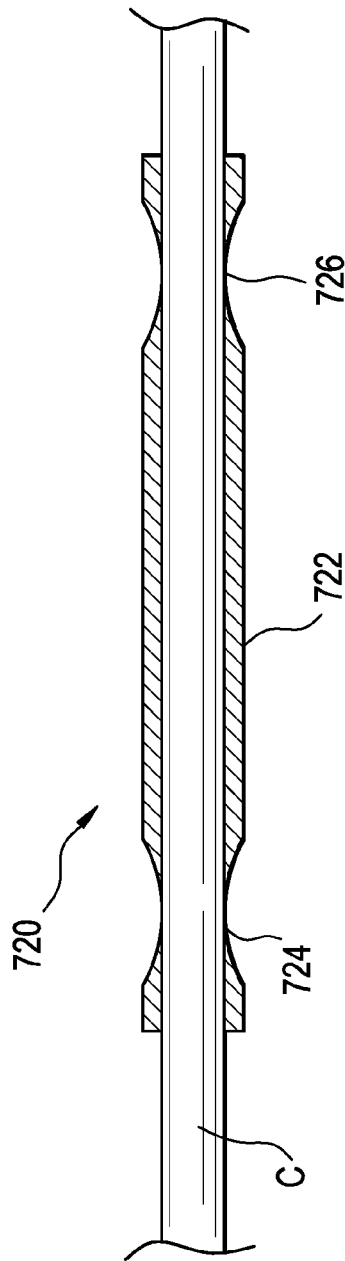

SURGICAL DEVICES WITH INTRACORPOREAL ELBOW JOINT

FIELD

The present invention relates to methods and devices for controlling movement of an end effector assembly on a distal end of a surgical device.

BACKGROUND

Minimally invasive surgery (MIS) is often preferred over traditional open surgery due to the reduced post-operative recovery time and minimal scarring associated therewith. Laparoscopic surgery is one type of MIS procedure in which one or more small incisions are formed in the abdomen and a trocar is inserted through each incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Conventional MIS devices include a handle, an elongate shaft, and an end effector at the distal end. Motion of the end effector is typically limited to four degrees of freedom: (1) rotation of the end effector about its longitudinal axis, which is achieved by rotating the entire device relative to the trocar, (2) in-out translational movement of the end effector, which is achieved by sliding the entire device longitudinally relative to the trocar, (3) up-down translational movement of the end effector, which is achieved by angling the device and trocar relative to the patient, and (4) left-right translational movement of the end effector, which is also achieved by angling the device and trocar relative to the patient. Some MIS devices also include a wrist joint proximal to the end effector which provides two additional degrees of freedom: (5) up-down pivot movement of the end effector and (6) left-right pivot movement of the end effector.

Conventional MIS devices suffer from a number of disadvantages. For example, the trocar angling that is required to achieve up-down translational movement and left-right translational movement of the end effector places a significant amount of strain on the incision in which the trocar is inserted, which can cause increased trauma and inadvertent release of insufflation gas. Moreover, this trocar angling makes it difficult if not impossible to operate effectively with two devices inserted into the same incision, or inserted into incisions that are in close proximity to each other, as the elongate shafts of the two devices interfere with one another when the devices are angled. Thus, in order to maintain optimum maneuverability, multiple incisions are used when multiple conventional MIS devices must be employed simultaneously, which further increases patient trauma and scarring.

By way of further example, controlling conventional MIS systems can be cumbersome, and motion error introduced by such devices makes end effector movement seem unnatural to the user. In addition, shear forces associated with conventional MIS instruments can be high, leading to increased user fatigue.

Various robotic systems have been developed to assist in MIS procedures. Robotic systems generally operate by translating user motion of a master device into control signals for driving a plurality of servos. The servos in turn selectively actuate a slave device to impart the desired motion thereto. One drawback with robotic systems, however, is the loss of a direct mechanical linkage between the user and the tissue or object being manipulated. With robotic systems, there can be no true force feedback given to the user. Another drawback is the high expense associated with such systems. Furthermore, robotic systems suffer from the same trocar angling requirements as conventional MIS devices.

Accordingly, there remains a need for improved methods and devices for controlling movement of an end effector assembly on a distal end of a surgical device.

SUMMARY

Surgical devices are disclosed herein that generally include an intracorporeal elbow joint to facilitate translational movement of an end effector while allowing a body portion of the surgical device and a trocar or working channel through which the device is inserted to be maintained in a fixed angular orientation relative to the patient. This allows a plurality of such devices to be used effectively with a single incision or access device. Such devices also generally provide end effector movement with six degrees of freedom, while maintaining a mechanical linkage between the user and the end effector and while mimicking and/or mirroring natural user movement. Various methods related to such devices are also disclosed.

In one aspect, a surgical device is provided that includes an elongate body having proximal and distal ends and a longitudinal axis, a master assembly coupled to the proximal end of the elongate body, the master assembly including a handle, and a slave assembly coupled to the distal end of the elongate body, the slave assembly including an end effector. Heave and sway of the handle relative to the longitudinal axis of the elongate body can cause corresponding heave and sway of the end effector relative to the longitudinal axis of the elongate body.

In some embodiments, the master assembly can be coupled to the elongate body by a proximal elbow assembly and the slave assembly can be coupled to the elongate body by a distal elbow assembly, the proximal and distal elbow assemblies being coupled to one another by a plurality of cables. The device can also include at least one mechanical linkage extending between the master assembly and the slave assembly. Actuation of the master assembly can cause corresponding actuation of the slave assembly.

Heave and sway of the slave component can be scaled in magnitude relative to heave and sway of the master component. Heave and sway of the master component can mimicked or mirrored by corresponding heave and sway of the slave component.

The device can also include a linear bearing in which the elongate body is slidably and rotatably received such that the elongate body can surge and roll with respect to the linear bearing. The device can also include a locking member slidable along the elongate body between a first position in which heave and sway of the master assembly is restrained by the locking member and a second position in which heave and sway of the master assembly is not restrained by the locking member.

In some embodiments, yaw of the handle pulls at least one of a plurality of yaw cables to cause corresponding yaw of the end effector, pitch of the handle pulls at least one of a plurality of pitch cables to cause corresponding pitch of the end effector, and heave and sway of the handle pulls at least one of a plurality of elbow cables to cause corresponding heave and sway of the end effector. The master assembly can include a central pulley system comprising a first pulley axle and a second pulley axle, the second pulley axle being perpendicularly oriented relative to the first pulley axle. Each of the plurality of yaw cables can wrap around one pulley disposed on the first pulley axle and one pulley disposed on the second pulley axle. Each of the plurality of pitch cables can wrap around two pulleys disposed on the first pulley axle and two pulleys disposed on the second pulley axle. Pulleys on the first and second pulley axles around which the yaw cables are wrapped can have a diameter that is approximately two times greater than a diameter of pulleys on the first and second pulley axles around which the pitch cables are wrapped.

The central pulley system can include a plurality of pulleys, each of the plurality of pulleys having first and second cable tracks extending circumferentially therearound. Each of the plurality of yaw cables and each of the plurality of pitch cables can be wrapped at least 225 degrees around at least one pulley of the central pulley system.

In another aspect, a surgical device is provided that includes an end effector having proximal and distal ends and a distal wrist assembly coupled to the proximal end of the end effector, the distal wrist assembly having a first pivot joint about which the end effector yaws and a second pivot joint about which the end effector pitches. The device also includes a distal elbow assembly coupled to a proximal end of the distal wrist assembly, the distal elbow assembly having a first elbow joint about which the distal wrist assembly heaves and sways. The device further includes a handle assembly having proximal and distal ends and first and second handle levers, and a proximal wrist assembly coupled to the distal end of the handle assembly, the proximal wrist assembly having a third pivot joint about which the handle assembly yaws and a fourth pivot joint about which the handle assembly pitches. The device also includes a proximal elbow assembly coupled to a distal end of the proximal wrist assembly, the proximal elbow assembly having a second elbow joint about which the proximal wrist assembly heaves and sways. An elongate body is disposed between the proximal and distal elbow assemblies. The device also includes a plurality of yaw cables extending from the handle assembly to the end effector, a plurality of pitch cables extending from the proximal wrist assembly to the distal wrist assembly, and a plurality of elbow cables extending from the proximal elbow assembly to the distal elbow assembly.

Yaw of the handle assembly pulls at least one of the yaw cables to cause corresponding yaw of the end effector, pitch of the handle assembly pulls at least one of the pitch cables to cause corresponding pitch of the end effector, and heave and sway of the handle assembly pulls at least one of the elbow cables to cause corresponding heave and sway of the end effector.

Yaw of the handle assembly can be mimicked or mirrored by corresponding yaw of the end effector. The corresponding yaw of the end effector can be scaled in magnitude relative to the yaw of the handle assembly. Pitch of the handle assembly can be mimicked or mirrored by the corresponding pitch of the end effector. The corresponding pitch of the end effector can be scaled in magnitude relative to the pitch of the handle assembly. Heave and sway of the handle assembly can be mimicked or mirrored by the corresponding heave and sway of the end effector.

In some embodiments, movement of the first and second handle levers towards one another pulls at least one of the yaw cables to cause corresponding movement of first and second jaws of the end effector towards one another. The first and second handle levers can pivot about at least one handle axis, the at least one handle axis being offset from a pivot axis of the third pivot joint and a pivot axis of the fourth pivot joint.

The device can also include a frame assembly that couples the elongate body to the proximal elbow assembly, the frame assembly including a plurality of pulleys for guiding the plurality of yaw cables, the plurality of pitch cables, and the plurality of elbow cables therethrough. The device can also include a linear bearing in which the elongate body is slidably and rotatably received such that the elongate body can surge and roll with respect to the linear bearing.

In some embodiments, each of the plurality of elbow cables includes a first end coupled to a first attachment point within the proximal elbow assembly and a second end coupled to a second attachment point within the distal elbow assembly, the first and second attachment points being offset 180 degrees from one another. Each of the plurality of elbow cables can be coupled to a corresponding tension adjustment screw threadably received in a tension plate of the proximal elbow assembly.

The device can also include a plurality of cable braces, each of the plurality of cable braces being coupled to a respective one of the plurality of elbow cables at two or more points, each of the plurality of braces being less susceptible to stretching than the plurality of elbow cables. The device can also include a locking member slidable along the elongate body between a first position in which movement of the proximal elbow assembly is restrained by the locking member and a second position in which movement of the proximal elbow assembly is not restrained by the locking member.

The proximal wrist assembly can include a central pulley system having a first pulley axle and a second pulley axle, the second pulley axle being perpendicularly oriented relative to the first pulley axle. Each of the plurality of yaw cables can wrap around one pulley disposed on the first pulley axle and one pulley disposed on the second pulley axle. Each of the plurality of pitch cables can wrap around two pulleys disposed on the first pulley axle and two pulleys disposed on the second pulley axle. Pulleys on the first and second pulley axles around which the yaw cables are wrapped can have a diameter that is approximately two times greater than a diameter of pulleys on the first and second pulley axles around which the pitch cables are wrapped. The central pulley system can include a plurality of pulleys, each of the plurality of pulleys having first and second cable tracks extending circumferentially therearound. Each of the plurality of yaw cables and each of the plurality of pitch cables can be wrapped at least 225 degrees around at least one pulley of the central pulley system. The handle assembly can include a plurality of handle pulleys, each of the plurality of handle pulleys having a terminal end of a respective yaw cable fixedly attached thereto.

In another aspect, a surgical device is provided that includes an end effector having proximal and distal ends, a distal wrist assembly coupled to the proximal end of the end effector, the distal wrist assembly having a first pivot joint about which the end effector yaws and a second pivot joint about which the end effector pitches, and a handle assembly having proximal and distal ends and first and second handle levers. The device also includes a proximal wrist assembly coupled to the distal end of the handle assembly, the proximal wrist assembly having a third pivot joint about which the handle assembly yaws and a fourth pivot joint about which the handle assembly pitches, and an elongate body disposed between the proximal and distal wrist assemblies. The device also includes a plurality of yaw cables extending from the handle assembly to the end effector and a plurality of pitch cables extending from the proximal wrist assembly to the distal wrist assembly. Yaw of the handle assembly pulls at least one of the yaw cables to cause corresponding yaw of the end effector, and pitch of the handle assembly pulls at least one of the pitch cables to cause corresponding pitch of the end effector.

In another aspect, a surgical device is provided that includes a proximal elbow assembly that includes first and second retainer housings, a first plurality of rods extending between and pivotally coupled to the first and second retainer housings, and a first plate disposed between the first and second retainer housings, the first plate having a plurality of openings through which the first plurality of rods are respectively received. The device also includes a distal elbow assembly that includes third and fourth retainer housings, a second plurality of rods extending between and pivotally coupled to the third and fourth retainer housings, and a second plate disposed between the third and fourth retainer housings, the second plate having a plurality of openings through which the second plurality of rods are respectively received. The device also includes an elongate body extending between the proximal and distal elbow assemblies, and a plurality of cables extending from the first plate, through the elongate body, to the second plate. Translational movement of the first retainer housing relative to the second retainer housing is transmitted through the plurality of cables to cause translational movement of the fourth retainer housing relative to the third retainer housing.

The device can include a handle coupled to the first retainer housing and an end effector coupled to the fourth retainer housing. The device can also include a proximal wrist assembly disposed between the handle and the first retainer housing, the proximal wrist assembly including a first pivot joint about which yaw of the handle can be adjusted relative to the first retainer housing and a second pivot joint about which pitch of the handle can be adjusted relative to the first retainer housing. The device can also include a distal wrist assembly disposed between the end effector and the fourth retainer housing, the distal wrist assembly including a third pivot joint about which yaw of the end effector can be adjusted relative to the fourth retainer housing and a fourth pivot joint about which pitch of the end effector can be adjusted relative to the fourth retainer housing.

In some embodiments, each of the plurality of cables attaches to an attachment point on the first plate and an attachment point on the second plate, the attachment point on the first plate being offset 180 degrees from the attachment point on the second plate.

In another aspect, an elbow assembly is provided that includes a proximal retainer housing having a first plurality of concavities formed therein, a distal retainer housing having a second plurality of concavities formed therein, a proximal elbow plate positioned between the proximal and distal retainer housings, the proximal elbow plate having a first plurality of openings formed therethrough, and a distal elbow plate positioned between the proximal and distal retainer housings, the distal elbow plate having a second plurality of openings formed therethrough. The elbow assembly also includes a torque tube extending between and being rigidly coupled to the proximal and distal elbow plates. The elbow assembly also includes a plurality of elongate rods, each of the plurality of rods extending through a corresponding one of the first plurality of openings and a corresponding one of the second plurality of openings, having a proximal end that is pivotally received within a corresponding one of the first plurality of concavities, and having a distal end that is pivotally received within a corresponding one of the second plurality of concavities.

In some embodiments, the proximal and distal ends of each of the plurality of rods are conical. The elbow assembly can also include a proximal retainer insert sized to be received within the proximal retainer housing and having a plurality of through holes formed therein through which control cables can be routed. The elbow assembly can also include a distal retainer insert sized to be received within the distal retainer housing and having a plurality of through holes formed therein through which control cables can be routed.

The elbow assembly can also include a cable tension plate having a plurality of openings formed therethrough, the plurality of rods extending through the plurality of openings. A plurality of tension adjustment members can be mounted to the cable tension plate.

In another aspect, an end effector assembly is provided that includes first and second major jaws pivotally coupled to each other about a first pivot joint, and first and second minor jaws pivotally coupled to each other about a second pivot joint. A distal end of the first minor jaw is pivotally coupled to the first major jaw and a distal end of the second minor jaw is pivotally coupled to the second major jaw.

In some embodiments, closure of the first and second major jaws at a first rate causes closure of the first and second minor jaws at a second rate that is greater than the first rate. The first major jaw can include a first recess sized to receive the first minor jaw, and/or the second major jaw can include a second recess sized to receive the second minor jaw. The first and second major jaws can be positioned in a closed configuration in which the first and second minor jaws are completely received within the first and second recesses.

In another aspect, a surgical method is provided that includes inserting a slave component of a surgical device into a body cavity, fixing an angular orientation of a body portion of the surgical device relative to the body cavity, and, while said angular orientation remains fixed, heaving and swaying a master component of the surgical device relative to the body portion, thereby causing corresponding heaving and swaying movement of the slave component relative to the body portion.

The method can also include surging the body portion to surge the slave component and/or rolling the body portion to roll the slave component. The method can also include yawing the master component relative to the body portion to yaw the slave component relative to the body portion and/or pitching the master component relative to the body portion to pitch the slave component relative to the body portion. The method can also include squeezing first and second handle levers of the master component together to cause first and second jaws of the slave component to move towards one another.

In some embodiments, movement of the master component induces scaled movement of the slave component. The method can also include articulating a wrist joint of the master component to control pitching and yawing movement of the slave component and/or articulating an elbow joint of the master component to control heaving and swaying movement of the slave component. The method can also include applying a pulling force to at least one wrist cable extending through the surgical device to induce yaw movement of the slave component, and/or applying a pulling force to at least one wrist cable extending through the surgical device to induce pitch movement of the slave component. The method can also include applying a pulling force to at least one elbow cable extending through the surgical device to induce heave movement of the slave component, and/or applying a pulling force to at least one elbow cable extending through the surgical device to induce sway movement of the slave component. The method can also include applying a pulling force to at least one wrist cable extending through the surgical device to actuate the slave component.

BRIEF DESCRIPTION OF THE DRAWINGS

The invention will be more fully understood from the following detailed description taken in conjunction with the accompanying drawings, in which:

FIG. 2A is a perspective view of one embodiment of a surgical device;

FIG. 2B is a perspective exploded view of the surgical device of FIG. 2A;

FIG. 2C is a perspective view of the surgical device of FIG. 2A inserted through a surgical access device and coupled to a frame;

FIG. 2D is a side view of the surgical device of FIG. 2A in an articulated configuration;

FIG. 2E is a bottom view of the surgical device of FIG. 2A in the same articulated configuration as in FIG. 2D;

FIG. 2F is a perspective view of the surgical device of FIG. 2A in the same articulated configuration as in FIGS. 2D-2E;

FIG. 6A is a perspective view of one embodiment of a proximal elbow assembly;

FIG. 6B is an exploded perspective view of the proximal elbow assembly of FIG. 6A;

FIG. 14A is a perspective view of the distal path of a first wrist cable;

FIG. 14B is a perspective view of the proximal path of the first wrist cable of FIG. 14A;

FIG. 16A is a perspective view of the distal path of a third wrist cable;

FIG. 16B is a perspective view of the proximal path of the third wrist cable of FIG. 16A;

FIG. 17A is a perspective view of the distal path of a fourth wrist cable;

FIG. 18A is a perspective view of the distal path of a fifth wrist cable;

FIG. 19A is a perspective view of the distal path of a sixth wrist cable;

FIG. 19B is a perspective view of the proximal path of the sixth wrist cable of FIG. 19A;

FIG. 20B is a perspective view of the proximal paths of the first through sixth wrist cables of FIGS. 14A-19B;

FIG. 21C is a perspective schematic view of the path of a third elbow cable;

FIG. 22 is a side schematic view of the distal elbow assembly of FIG. 4A, the proximal elbow assembly of FIG. 6A, and the elbow cables of FIGS. 21A-21C;

FIG. 23 is a cross-sectional side view of a cable and one exemplary embodiment of an anti-stretch brace;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Terminology

Figure 1:
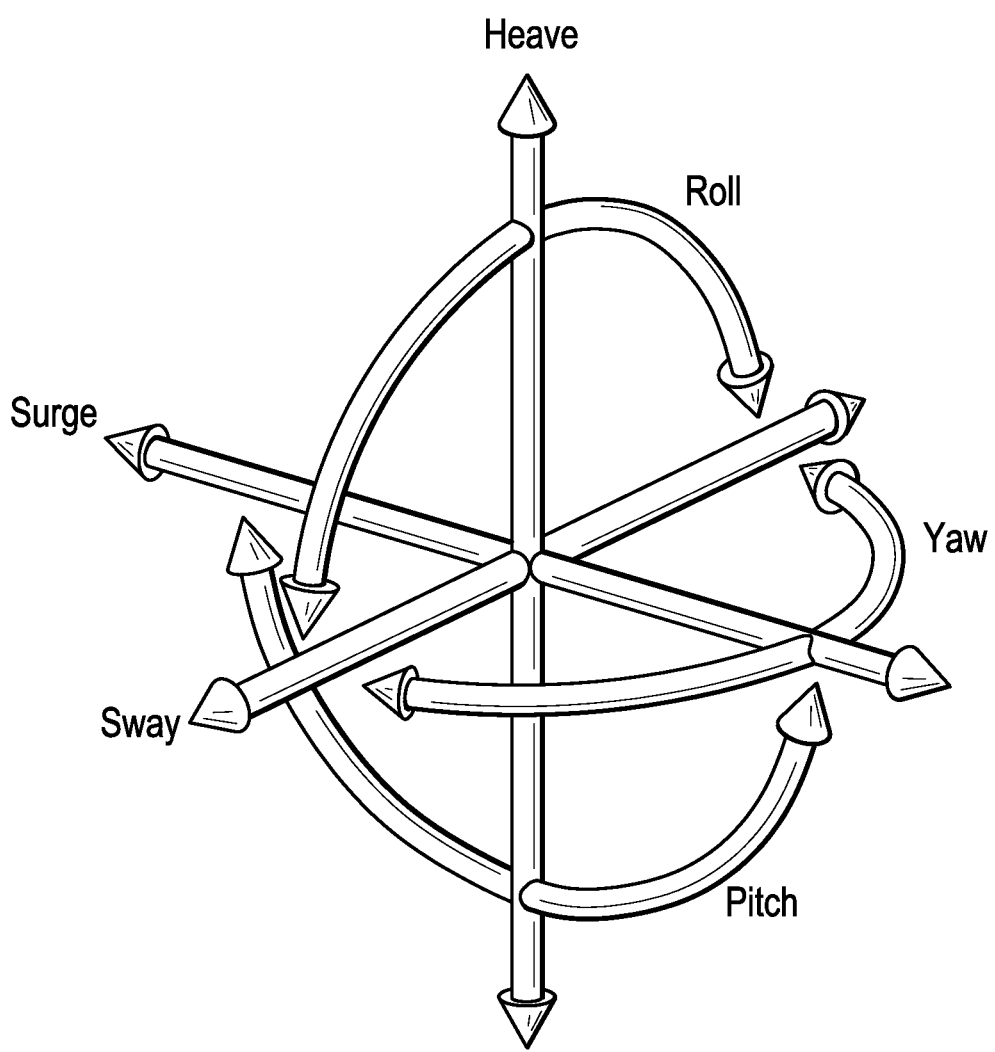
FIG. 1 is an illustration of the six degrees of freedom of a rigid body.
Figure 3A:
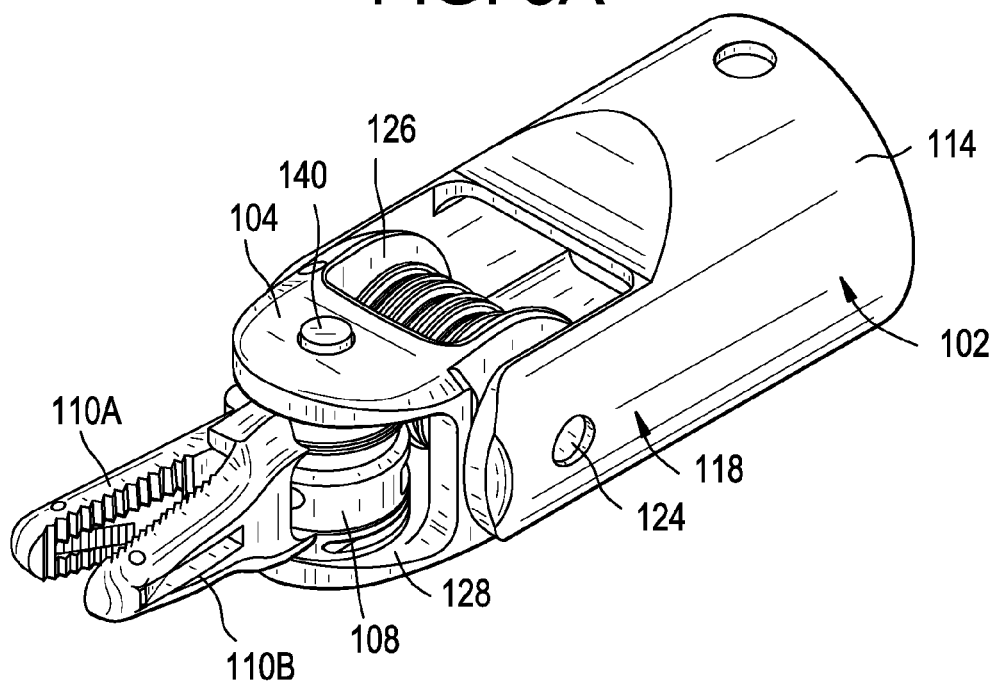
FIG. 3A is a perspective view of one embodiment of a distal wrist assembly.
Figure 3B:
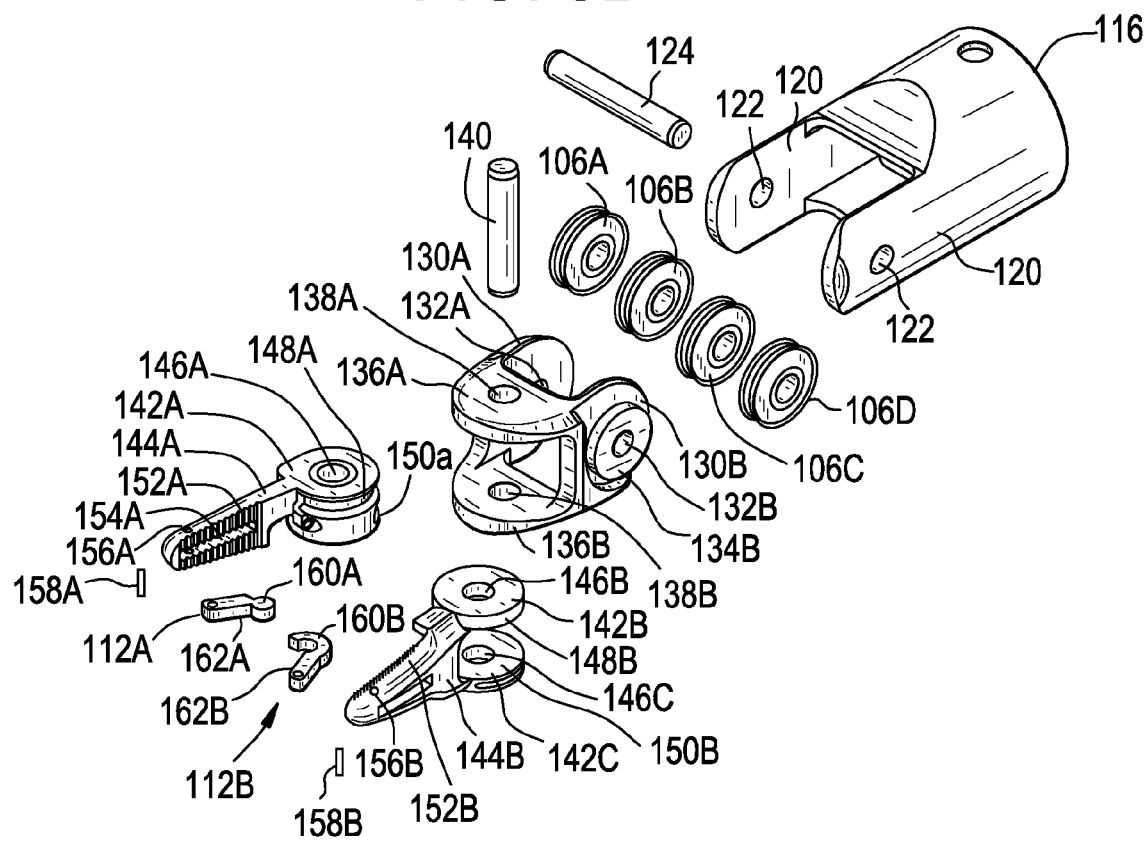
FIG. 3B is an exploded perspective view of the distal wrist assembly of FIG. 3A.
Figure 3C:
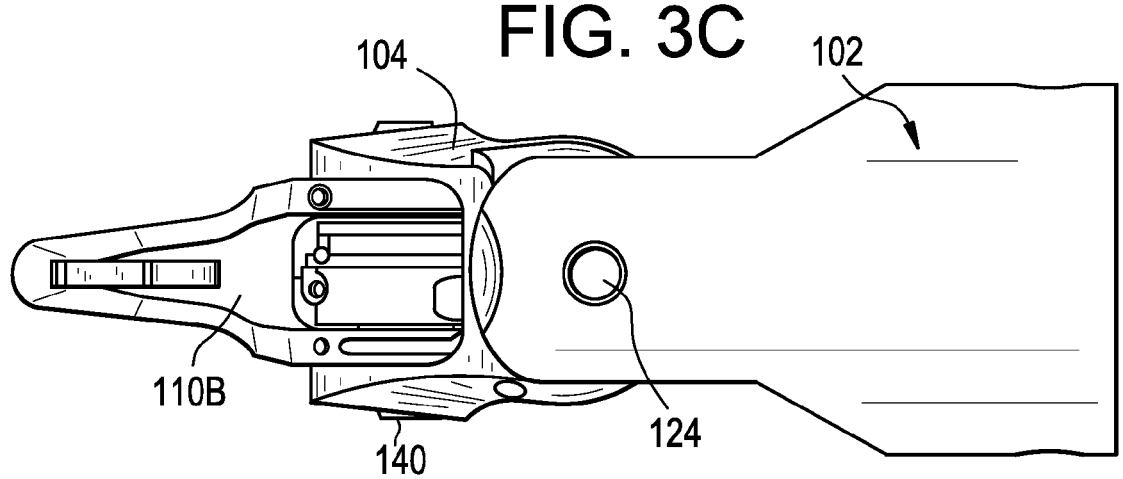
FIG. 3C is a side view of the distal wrist assembly of FIG. 3A.
Figure 3D:
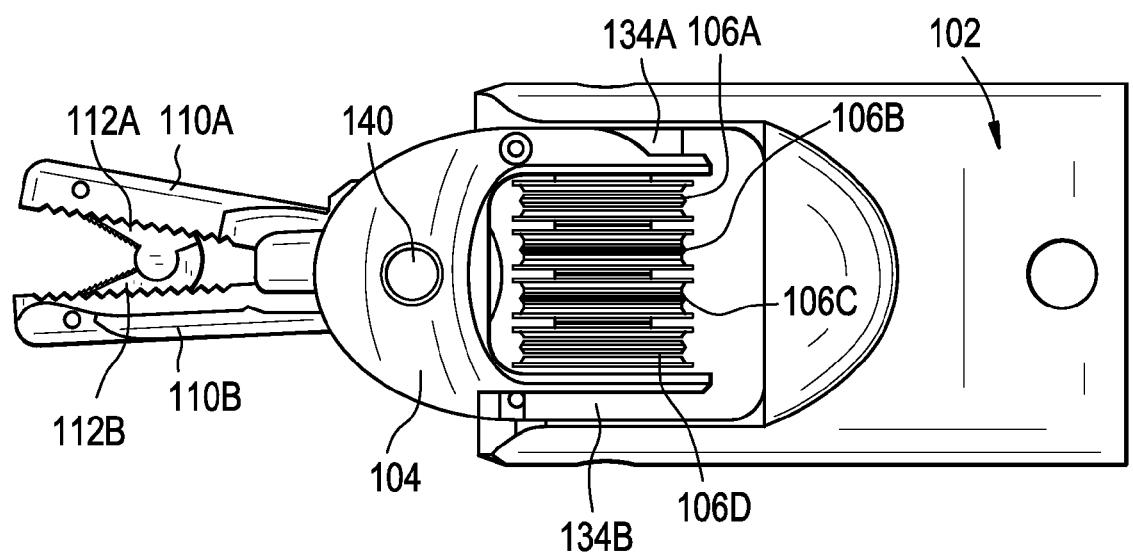
FIG. 3D is a top view of the distal wrist assembly of FIG. 3A.

There are a number of ways in which to describe an object's position and orientation in space. For example, the position and orientation of an object can be characterized in terms of the object's degrees of freedom. The degrees of freedom of an object are the set of independent variables that completely identify the object's position and orientation. As shown in FIG. 1, the six degrees of freedom of a rigid body with respect to a particular Cartesian reference frame can be represented by three translational (position) variables (e.g., surge, heave, and sway) and by three rotational (orientation) variables (e.g., roll, pitch, and yaw).

For convenience of description, surge is sometimes described herein as translational movement in an "in" direction or an "out" direction, heave is sometimes described as translational movement in an "up" direction or a "down" direction, and sway is sometimes described as translational movement in a "left" direction or a "right" direction. Likewise, roll is sometimes described herein as rotation about a longitudinal axis, pitch is sometimes described as pivoting in the up direction or the down direction, and yaw is sometimes described as pivoting in the left direction or the right direction. An exemplary mapping of the in, out, up, down, left, and right directions to a surgical device is shown in FIG. 2A. This mapping is generally used throughout the description that follows, for example to describe the relative positioning of components of the device (e.g., "upper," "lower," "left," "right") or to describe direction of movement within a particular degree of freedom (e.g., "leftwards," "rightwards," "up," "down"). This terminology and the illustrated mapping are not intended to limit the invention, and a person having ordinary skill in the art will appreciate that these directional terms can be mapped to the device or any component thereof in any of a variety of ways.

Components described herein as being coupled may be directly coupled, or they may be indirectly coupled via one or more intermediate components.

As noted below, the devices disclosed herein can be at least partially positioned inside a patient's body cavity through an access point in a tissue surface for minimally invasive surgical procedures. Typically, cannulas are used to provide a pathway through a tissue surface and to prevent a surgical device or guide tube from rubbing on patient tissue. Cannulas can be used for both incisions and natural orifices. Some surgical procedures require insufflation, and the cannula can include one or more seals to prevent insufflation gas from leaking past the surgical device or guide tube. In some embodiments, the cannula can have a housing coupled thereto with one or more sealed ports for receiving various types of instruments or for receiving a plurality of the devices disclosed herein. It will be appreciated by those skilled in the art that any of the surgical device components disclosed herein can have a functional seal disposed thereon, therein, and/or therearound to prevent and/or reduce insufflation leakage while any portion of the device is disposed through a surgical access port, such as the cannula noted above. The surgical devices disclosed herein can also be used in open surgical procedures. As used herein, a surgical access point is a point at which the device enters a body cavity through a tissue surface, whether through a cannula in a minimally invasive procedure or through an incision in an open procedure.

The various components of the devices disclosed herein can be formed from any of a variety of materials known in the art and suitable for use in surgical devices. For example, the various components can be formed from metal (e.g., stainless steel, titanium), plastic (e.g., polyetheretherketone (PEEK)), and/or combinations thereof.

Further details regarding surgical devices are disclosed in U.S. patent application Ser. No. 12/971,434, entitled "Surgical System and Methods for Mimicked Motion," the entire contents of which are incorporated herein by reference and in U.S. patent application Ser. No. 12/904,280, entitled "Laparoscopic Device with Distal Handle," the entire contents of which are incorporated herein by reference.

Surgical Device Generally

One exemplary embodiment of a surgical device 10 is illustrated in FIGS. 2A-2F. The surgical device 10 generally includes a distal wrist assembly 100, a distal elbow assembly 200, a body assembly 300, a proximal elbow assembly 400, a proximal wrist assembly 500, and a handle assembly 600. The device 10 can also include a plurality of cables, which for clarity of illustration are not shown in FIGS. 2A-2F.

The device 10 can include a "master" or "input" component (i.e., a pair of handle levers 602A, 602B included in the handle assembly 600) and a "slave" or "output" component (i.e., an end effector assembly 108 included in the distal wrist assembly 100). The device 10 can provide a mechanical linkage between the master component and the slave component such that movement or actuation of the master component effects corresponding movement or actuation of the slave component. As explained below, this corresponding movement or actuation can be mirrored, mimicked, or some combination thereof, depending on the configuration of the device. In addition, the degree of actuation or movement can be scaled.

In use, as shown in FIG. 2C, the distal wrist assembly 100, the distal elbow assembly 200, and at least a portion of the body assembly 300 can be inserted through the working channel of a surgical access device, such as a trocar or cannula 12 positioned in an incision 14 formed in a patient 16. The slave component can thus be positioned within a body cavity 18 of the patient 16, while the master component remains external to the body cavity 18.

The body assembly 300 of the device can be slidably and rotatably received within a linear bearing 20, the position and orientation of which can be fixed in a desired position within the operative field. For example, the linear bearing 20 can be coupled to a frame 22 that is affixed to a stationary object, such as a hospital bed, an operating table, the floor, the ceiling, etc. Although the position and orientation of the linear bearing 20 is fixed, the body assembly 300 is free to surge (e.g., by sliding along its longitudinal axis L in or out of the linear bearing 20 and the trocar 12) or to roll (e.g., by rotating about its longitudinal axis L relative to the linear bearing 20 and the trocar 12). It will be appreciated, however, that the frame and linear bearing 20 can substantially prevent the body assembly 300 from swaying, heaving, pitching, and yawing. This restriction dramatically reduces interference between plural devices inserted through a single incision or access device, as the elongate body assemblies of the plural devices can be kept substantially parallel or in a fixed angular orientation relative to one another. At the same time, the ability to move the end effector assemblies of the plural devices with at least six degrees of freedom can be preserved. Exemplary single site access devices with which the device 10 can be used are disclosed in U.S. Publication No. 2011/0028793, entitled "Methods and Devices for Providing Access into a Body Cavity," the entire contents of which are incorporated herein by reference.

Once the device 10 is secured to a frame or other fixed reference, the extracorporeal master component can be manipulated by a user to control movement and actuation of the intracorporeal slave component.

The end effector assembly 108 can be actuated by squeezing the handle levers 602A, 602B together to squeeze together the jaws of the end effector assembly, or by spreading the handle levers apart to spread apart the jaws of the end effector assembly. The end effector assembly 108 can also be moved with at least six degrees of freedom. Surge (in-out translational movement) and roll (longitudinal rotation) of the handle levers 602A, 602B can be communicated to the end effector assembly 108 by the body assembly 300. Sway (left-right translational movement) and heave (up-down translational movement) of the handle levers 602A, 602B can be communicated to the end effector assembly 108 by the proximal and distal elbow assemblies 200, 400. Pitch (up-down pivoting movement) and yaw (left-right pivoting movement) of the handle levers 602A, 602B can be communicated to the end effector assembly 108 by the proximal and distal wrist assemblies 100, 500.

FIGS. 2D-2F show views of the device 10 in an articulated position from various observation angles. The device is articulated in the exact same manner in each of FIGS. 2D-2F, the only change being in the position from which the device 10 is observed.

As shown in FIG. 2D, in which the device 10 is viewed from the side, tilting the nose of the handle levers up causes the proximal wrist assembly 500 to pivot. This pivoting is transmitted by cable to cause the distal wrist assembly 100 to pivot such that the nose of the end effector assembly is likewise tilted up, thereby achieving mimicked pitch.

As also shown in FIG. 2D, translating the nose of the handle levers down causes the proximal elbow assembly 400 to shift. This shifting is transmitted by cable to cause the distal elbow assembly 200 to shift such that the nose of the end effector assembly is likewise translated down, thereby achieving mimicked heave.

As shown in FIG. 2E, tilting the nose of the handle levers left causes the proximal wrist assembly 500 to pivot. This pivoting is transmitted by cable to cause the distal wrist assembly 100 to pivot such that the nose of the end effector assembly is likewise tilted left, thereby achieving mimicked yaw.

As also shown in FIG. 2E, translating the nose of the handle levers right causes the proximal elbow assembly 400 to shift. This shifting is transmitted by cable to cause the distal elbow assembly 200 to shift such that the nose of the end effector assembly is likewise translated right, thereby achieving mimicked sway.

The device 10 can thus permit extracorporeal control of end effector assembly actuation and end effector assembly movement with at least six degrees of freedom. The structure and operation of the device 10 is described in detail below.

Distal Wrist Assembly

The distal wrist assembly 100 can provide a first pivot joint for altering the pitch of the end effector assembly (e.g., for pivoting the end effector assembly in the "up-down" direction) and a second pivot joint for altering the yaw of the end effector assembly (e.g., for pivoting the end effector assembly in the "left-right" direction). The distal wrist assembly 100 can also include the end effector assembly and a plurality of pulleys for receiving the various cables that impart pitch (up-down pivot) or yaw (left-right pivot) motion to the end effector assembly.

As shown in FIGS. 3A-3D, the distal wrist assembly 100 can include first and second wrist frames 102, 104, a plurality of guide pulleys 106A, 106B, 106C, 106D, and an end effector assembly 108. In the illustrated embodiment, the end effector assembly 108 includes first and second major jaws 110A, 110B and first and second minor jaws 112A, 112B, however any of a variety of end effectors can be used without departing from the scope of the present invention. For clarity of illustration, the cables used to control movement of the distal wrist assembly 100 are not shown in FIGS. 3A-3D, however these cables are illustrated and described in detail below.

The first wrist frame 102 can include a cylindrical body portion 114 that defines a central passageway 116 through which the control cables can be routed. A clevis 118 extending distally from the cylindrical body portion 114 can be defined by a pair of opposed prongs 120, each prong having a through hole 122 formed therein for receiving a pitch (up-down) pivot pin 124.

The second wrist frame 104 can include a double clevis, the proximal clevis 126 being oriented perpendicular to the distal clevis 128. The proximal clevis 126 can include opposed prongs 130A, 130B having through holes 132A, 132B formed therein for receiving the pitch pivot pin 124 such that the second wrist frame 104 is rotatable about the pitch pivot pin 124. It will be appreciated that the pitch pivot pin 124 can be fixed with respect to one of the first wrist frame 102 and the second wrist frame 104, or can be rotatable relative to both the first wrist frame 102 and the second wrist frame 104. Each prong 130A, 130B of the proximal clevis 126 can also include an integral pulley 134A, 134B for receiving and/or seating a control cable. The proximal clevis 126 can be sized to be received within the clevis 118 of the first wrist frame 102 such that the first wrist frame 102, second wrist frame 104, and pitch pivot pin 124 form a pivot joint about which the end effector assembly 108 can be pivoted in the up-down direction (e.g., about which the end effector assembly 108 can pitch). The pitch pivot pin 124 can also serve as an axle for the guide pulleys 106A, 106B, 106C, 106D which are individually rotatable relative to the pitch pivot pin 124.

The distal clevis 128 of the second wrist frame 104 can include opposed prongs 136A, 136B having through holes 138A, 138B formed therein for receiving a yaw (left-right) pivot pin 140. The opposed prongs 136A, 136B can be spaced a distance apart from one another such that the end effector assembly 108, and in particular the cylindrical portions 142A, 142B, 142C of the first and second major jaws 110A, 110B, can be rotatably received therebetween, as described below.

The first major jaw 110A can include a proximal cylindrical portion 142A and an elongate distal tip 144A. The proximal cylindrical portion 142A can have a through hole 146A formed therein for receiving the yaw pivot pin 140, and can have upper and lower cable tracks 148A, 150A formed therein such that the proximal cylindrical portion 142A can act as a cable pulley. The distal tip 144A can have a gripping surface 152A with a plurality of surface features formed thereon to facilitate gripping or grasping of various objects with the device 10, such as needles, sutures, or tissue. A cavity or recess 154A can be formed in the gripping surface 152A for receiving the first minor jaw 112A. A through hole 156A can be formed in the distal tip 144A intersecting with the cavity 154A for receiving a first minor jaw pivot pin 158A about which the first minor jaw 112A rotates.

The second major jaw 110B can include upper and lower proximal cylindrical portions 142B, 142C and an elongate distal tip 144B. The upper and lower proximal cylindrical portions 142B, 142C can have through holes 146B, 146C formed therein for receiving the yaw pivot pin 140 and can be spaced apart from one another such that the proximal cylindrical portion 142A of the first major jaw 110A can be received therebetween. The upper and lower proximal cylindrical portions 142B, 142C can also have respective cable tracks 148B, 150B formed therein such that they can act as cable pulleys. The distal tip 144B can have a gripping surface 152B with a plurality of surface features formed thereon which can be sized and positioned to interlock with and engage the surface features formed on the first major jaw 110A. A cavity or recess 154B can be formed in the gripping surface 152B for receiving the second minor jaw 112B. A through hole 156B can be formed in the distal tip 144B intersecting with the cavity 154B for receiving a second minor jaw pivot pin 158B about which the second minor jaw 112B rotates.

The second wrist frame 104, the first and second major jaws 110A, 11B, and the yaw pivot pin 140 can collectively form a pivot joint about which the end effector assembly 108 can yaw (i.e., pivot in the left-right direction). When the first and second major jaws 110A, 110B are pivoted about the yaw pivot pin 140 simultaneously in the same direction, left-right pivot motion or yaw of the end effector assembly 108 can be achieved. If only one of the jaws 110A, 110B is pivoted about the yaw pivot pin 140, or if the jaws 110A, 110B are pivoted in opposite directions, actuation of the end effector assembly 108 (e.g. opening or closing of the jaws) can be achieved.

The first and second major jaws 110A, 110B can be actuated using one or more cables, as described in detail below. One concern associated with cable-based systems is that an increase in cable tension is generally required to achieve an increase in closing or gripping force at the end effector. The increased tension on the cables increases friction between the cables and the various pulleys about which they are wrapped, dramatically increasing the input force required to manipulate the device and reducing the overall smoothness of operation. In the illustrated embodiment, this issue is addressed by the first and second minor jaws 112A, 112B of the end effector assembly 108.

The first and second minor jaws 112A, 112B can each include a proximal cylindrical portion 160A, 160B and a distal tip portion 162A, 162B having a gripping surface formed thereon. The proximal cylindrical portions 160A, 160B of the jaws 112A, 112B can be rotatably coupled to each other, for example using a ball and socket joint, cylinder and cup joint, pivot pin, or other coupling. In addition, the distal tips 162A, 162B of the jaws 112A, 112B can be rotatably coupled to the first and second major jaws 110A, 110B via the first and second minor jaw pivot pins 158A, 158B, respectively. In operation, as the major jaws 110A, 110B approach one another, moving towards a closed position, the minor jaws 112A, 112B likewise approach one another, while simultaneously being received within the corresponding cavities 154A, 154B formed in the major jaws 110A, 110B.

The minor jaws 112A, 112B can be shorter than the major jaws 110A, 110B and therefore can provide a mechanical advantage which amplifies the closing force without requiring a corresponding increase in cable tension. The length of the minor jaws 112A, 112B and the point at which they are coupled to the major jaws 110A, 110B can be varied to obtain the desired amplification factor. In the illustrated embodiment, the proximal ends of the minor jaws 112A, 112B are positioned distal to the proximal ends of the major jaws 110A, 110B and the distal ends of the minor jaws 112A, 112B are positioned adjacent to or just proximal to the distal ends of the major jaws 110A, 110B. The ratio of the length of the major jaws 110A, 110B to the length of the minor jaws 112A, 112B can be about 2:1, as shown, or can be any of a variety of other ratios, such as 3:1, 4:1, 5:1, 10:1, etc.

Distal Elbow Assembly

The distal elbow assembly 200 can provide for 360 degree translational movement of the distal wrist assembly 100 (and thus the end effector assembly 108) relative to the body assembly 300.

As shown in FIGS. 4A-4D, the distal elbow assembly 200 can include proximal and distal retainer housings 202$p$, 202$d$, proximal and distal retainer inserts 204$p$, 204$d$, proximal and distal elbow plates 206$p$, 206$d$ coupled to one another by a torque tube 208, and a plurality of cone rods 210A, 210B, 210C. For clarity of illustration, the cables used to control movement of the distal elbow assembly 200 are not shown in FIGS. 4A-4D, nor are the cables used to control movement of the distal wrist assembly 100, which cables extend through the distal elbow assembly 200. These cables are illustrated and described in detail below.

The proximal and distal retainer housings 202$p$, 202$d$ can include cylindrical bodies having passageways 212$p$, 212$d$ formed therethrough for receiving the cables used to impart motion to the distal wrist assembly 100. A reduced diameter portion 214$d$ of the distal retainer housing 202$d$ can be sized to be received within the proximal end of the first wrist frame 102, so as to couple the distal wrist assembly 100 to the distal elbow assembly 200. A reduced diameter portion 214$p$ of the proximal retainer housing 202$p$ can be sized to be received within a distal opening 304 of the body assembly 300, so as to couple the distal elbow assembly 200 to the body assembly 300. The proximal and distal retainer housings 202$p$, 202$d$ can be coupled to the distal wrist assembly 100 and the body assembly 300, respectively, using any of a variety of techniques, such as a friction fit, weld joint, adhesives, screws, pins, rivets, and so forth. In addition, tension applied to the cables extending through the device 10 can augment the mating between the various assemblies thereof.

An enlarged diameter portion 216$p$ of the proximal retainer housing 202$p$ can be sized to receive the proximal retainer insert 204$p$. The inner circumference of the enlarged diameter portion 216$p$ can include three protrusions 218$p$ spaced evenly 120 degrees apart from one another. A concavity 220$p$ can be formed in the distal-facing surface of each of the protrusions 218$p$ for receiving the proximal conical tip 230$p$ of a corresponding cone rod 210.

The proximal retainer insert 204$p$ can include a cylindrical body having three cutouts 222$p$ formed therein. The three cutouts 222$p$ can be spaced evenly 120 degrees apart from one another about the circumference of the proximal retainer insert 204$p$ and can be sized to receive the three protrusions 218$p$ formed in the proximal retainer housing 202$p$. The proximal retainer insert 204$p$ can also include a plurality of through holes 224$p$ which can serve as a guide channel for the various cables extending through the device 10. The through holes 224$p$ can optionally be coated or lined with a friction reducing material to facilitate sliding of the cables therethrough. It will be appreciated that although the proximal retainer housing 202$p$ and proximal retainer insert 204$p$ are shown as separate components, they can also be integrally formed with each other.

For the sake of brevity, a detailed description of the construction and function of the distal retainer housing 202$d$ and insert 204d is omitted, it being understood that the distal retainer housing 202d and insert 204d are essentially identical to the proximal retainer housing 202p and insert 204d, except that they are flipped 180 degrees.

The proximal and distal elbow plates 206p, 206d can be coupled to one another via the torque tube 208, which can be mated to the center of the elbow plates 206p, 206d. The torque tube 208 can be fixedly coupled or formed integrally with the proximal and distal elbow plates 206p, 206d such that rotational movement of the elbow plates relative to one another about the longitudinal axis of the torque tube 208 is prevented. The proximal and distal elbow plates 206p, 206d can be disk shaped bodies having a variety of openings formed therein. Three oval-shaped rod passages 226 can be formed in the elbow plates, through which the cone rods 210 can be slidably received. The three rod passages 226 can be spaced equally 120 degrees apart from one another about the circumference of the elbow plates 206p, 206d. The size and oval shape of the passages 226 can permit the cone rods 210 to angle slightly radially towards and away from the center of the elbow plate, but can prevent the rods 210 from angling tangentially relative to the elbow plate. This allows for translational movement of the distal retainer housing 202d relative to the proximal retainer housing 202p, while preventing rotation of the distal retainer housing 202d relative to the proximal retainer housing 202p about the longitudinal axis of the torque tube 208. In other words, the elbow plates 206p, 206d and torque tube 208 can prevent the distal elbow assembly 200 from twisting about the longitudinal axis of the torque tube 208.

The elbow plates 206p, 206d can also include a number of through holes 228 to allow passage of the various cables extending through the device 10.

The cone rods 210 can be substantially rigid, elongate, cylindrical bodies having conical tips 230p, 230d formed at the proximal and distal ends thereof. Each cone rod 210 can extend from the distal retainer housing 202d, where its distal tip 230d can be seated within a corresponding concavity 220d, through the proximal and distal elbow plates 206p, 206d, and into the proximal retainer housing 202p, where its proximal tip 230p can be seated within a corresponding concavity 220p. The cone rods 210 can be formed with conical tips to reduce friction as the rods are angled within the concavities 220p, 220d. The cone rods 210 can be free to slide relative to the proximal and distal elbow plates 206p, 206d, which serve to maintain a substantially parallel relationship between all three cone rods 210A, 210B, 210C at all times, regardless of how the distal elbow assembly 200 is manipulated. As described in further detail below, cables extending through the device 10 can be coupled at various points to the proximal elbow plate 206p. When tension is applied to one or more of the cables (i.e., when one or more of the cables are pulled), the proximal elbow plate 206p moves laterally and is angled relative to the proximal retainer housing 202p, causing the cone rods 210 to tilt in the same direction relative to the proximal retainer housing 202p. As a result, the distal retainer housing 202d, as well as the distal wrist assembly 100 and end effector assembly 108 coupled thereto, are translated relative to the proximal retainer housing 202p.

Figure 4A:
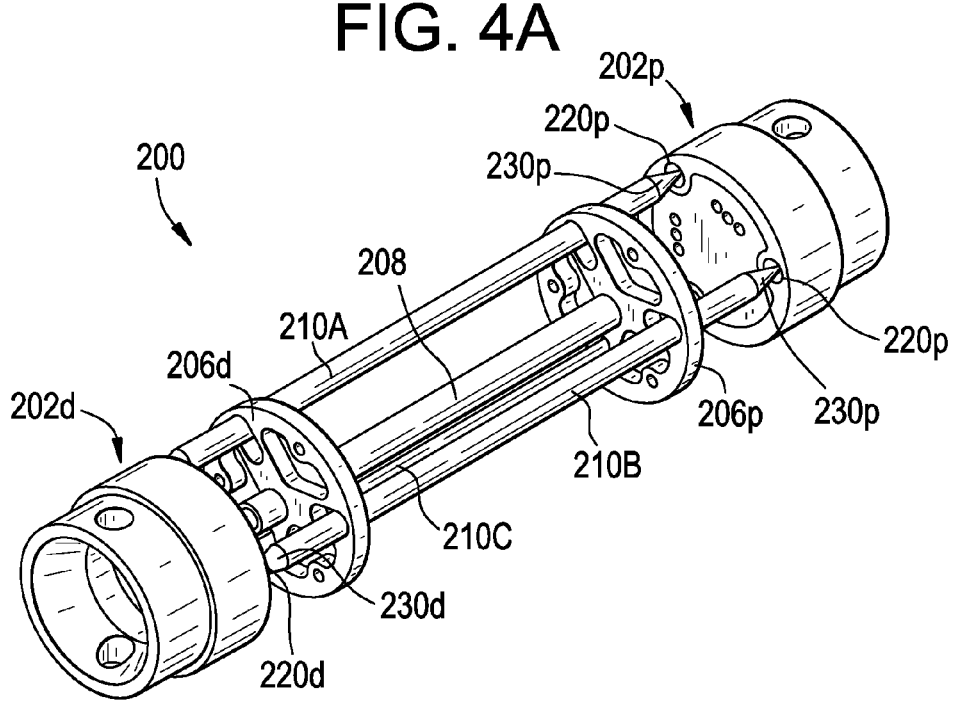
FIG. 4A is a perspective view of one embodiment of a distal elbow assembly.
Figure 4B:
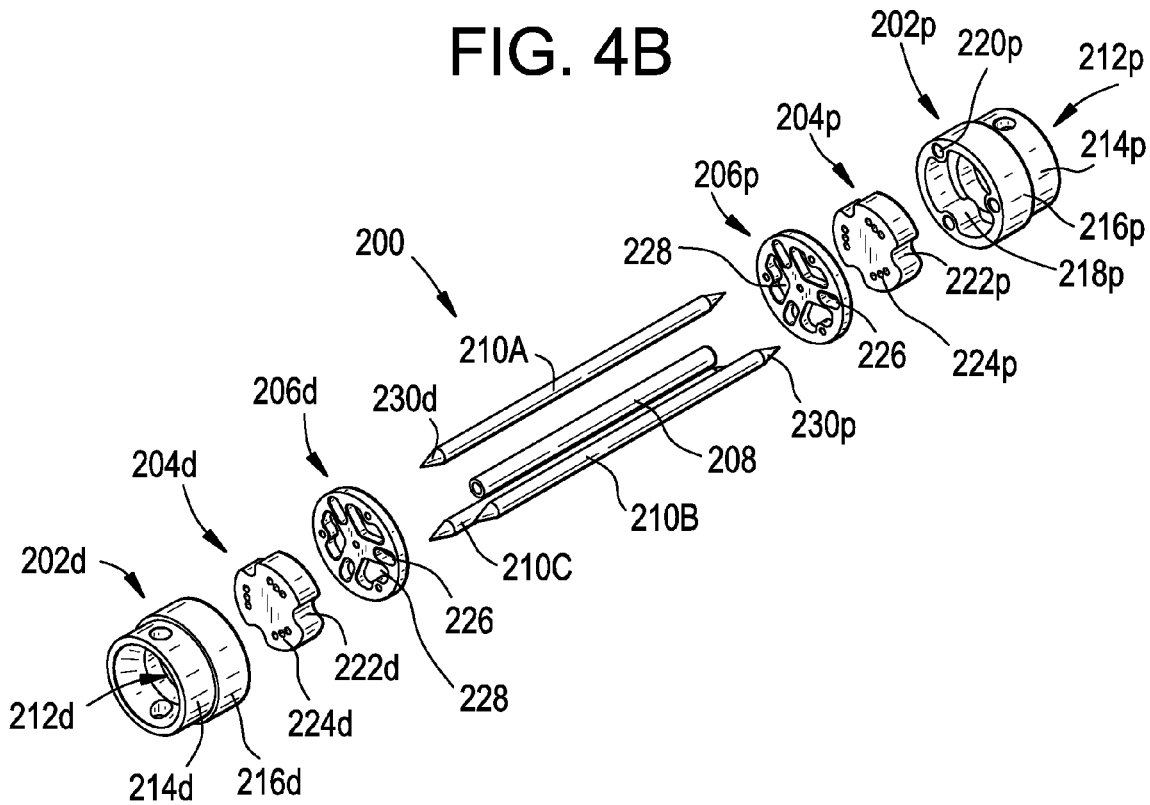
FIG. 4B is an exploded perspective view of the distal elbow assembly of FIG. 4A.
Figure 4C:
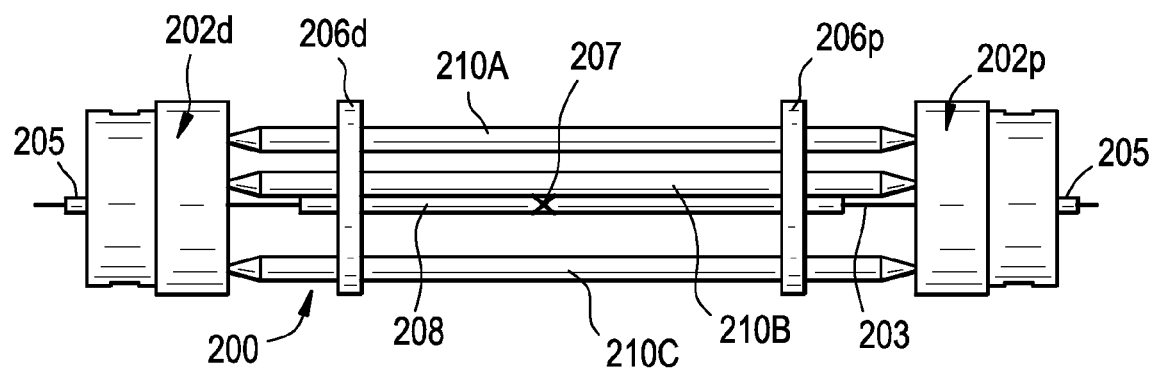
FIG. 4C is a side view of the distal elbow assembly of FIG. 4A.
Figure 4D:
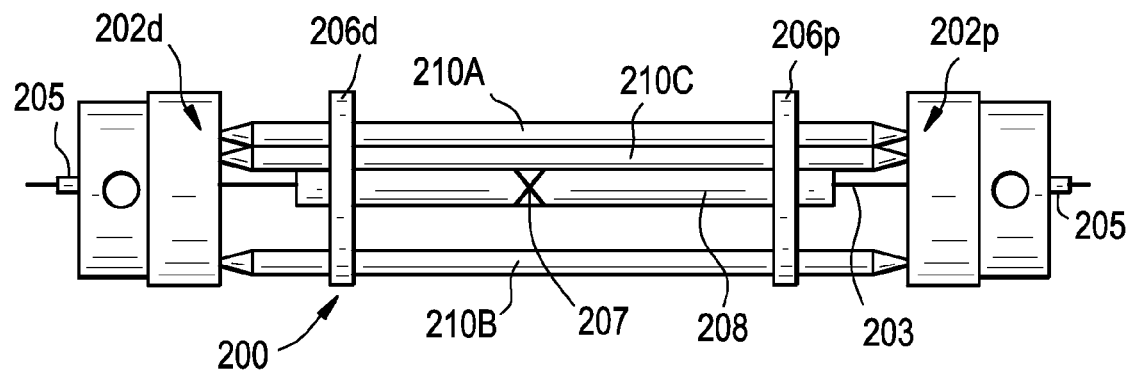
FIG. 4D is a top view of the distal elbow assembly of FIG. 4A.

The cone rods 210 can be substantially the same length and can be retained under compression within the concavities 220p, 220d formed in the proximal and distal retainer housings 202p, 202d by tension applied to the cables extending through the device 10. As shown in FIGS. 4C and 4D, an anchor cable 203 can extend through the distal retainer housing 202d, the torque tube 208, and the proximal retainer housing 202p. First and second clips 205 can be crimped onto the ends of the anchor cable 203, adjacent to the proximal and distal retainer housings 202p, 202d. In addition, a center point 207 of the torque tube 208 can be crimped down around the anchor cable 203. The anchor cable 203 can thus be effective to maintain the torque tube 208 and the elbow plates 206p, 206d mounted thereto in a substantially fixed longitudinal position within the distal elbow assembly 200 (e.g., approximately centered between the proximal and distal retainer housings 202p, 202d in the longitudinal direction).

Body Assembly

The body assembly 300 couples the proximal and distal elbow assemblies 200, 400 to one another and houses the various cables used to control movement and actuation of the device 10. The length of the body assembly 300 can vary depending on any of a variety of parameters, such as surgeon preference, patient size, and location within a patient of a surgery to be performed. The diameter of the body assembly 300 can be selected to correspond to the diameter of a working channel in which the device 10 is to be used.

Figure 5:
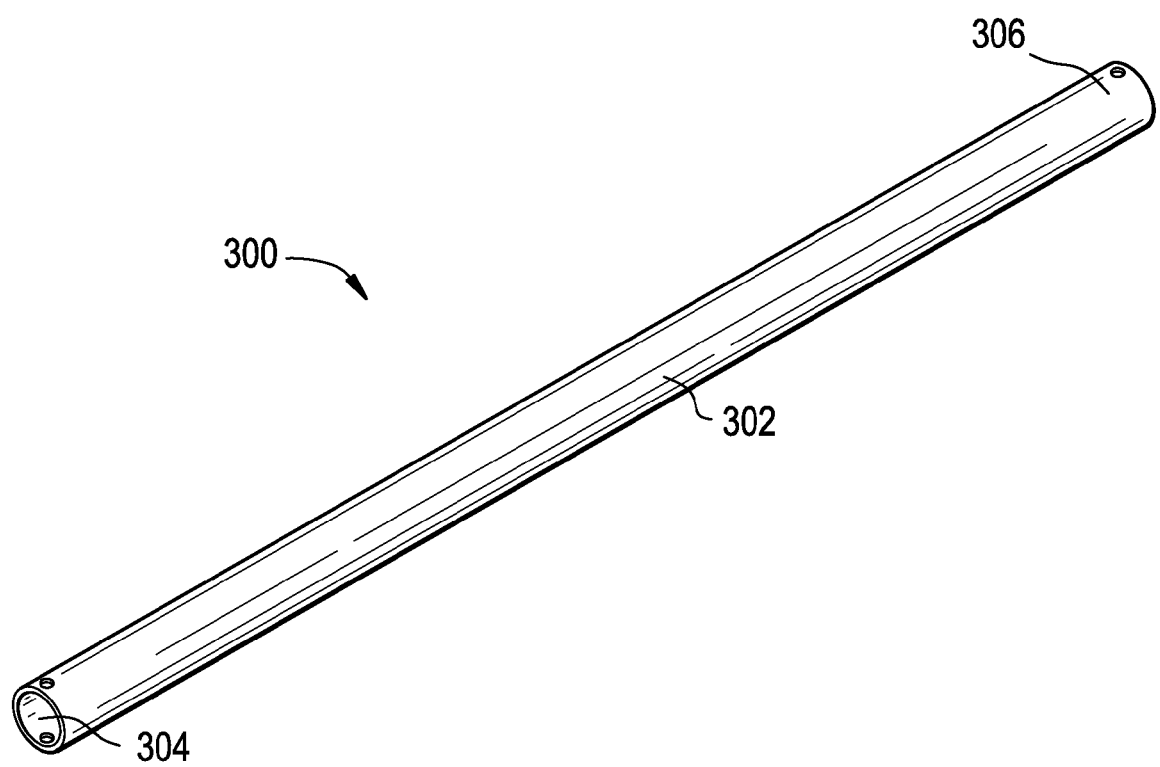
FIG. 5 is a perspective view of one embodiment of a body assembly.

As shown in FIG. 5, the body assembly 300 can include an elongate tubular outer housing 302. The outer housing 302 of the body assembly 300 can include a distal opening 304 sized to receive the reduced diameter portion 214p of the proximal retainer housing 202p of the distal elbow assembly 200. The outer housing 302 can also include a proximal end 306 sized to be received within a distal cavity 414d formed in the distal retainer housing 402d of the proximal elbow assembly 400, as explained below.

The outer housing 302 of the body assembly 300 can be sized to be slidably and rotatably received within a central lumen of the linear bearing 20. In one embodiment, the linear bearing 20 includes a hollow tube having a plurality of ball bearings or other friction reducing features lining an interior surface thereof, such that the body assembly 300 can slide longitudinally within the linear bearing (surge) and rotate longitudinally within the linear bearing (roll).

Proximal Elbow Assembly

The proximal elbow assembly 400 is the "master" counterpart to the "slave" distal elbow assembly 200. Movement of the proximal elbow assembly 400 can be mirrored by the distal elbow assembly 200 such that translational movement (e.g., heave and sway) of components proximal to the proximal elbow assembly 400 can be mimicked by components distal to the distal elbow assembly 200.

As shown in FIGS. 6A-6D, the proximal elbow assembly 400 can include proximal and distal retainer housings 402p, 404d, proximal and distal retainer inserts 404p, 404d, proximal and distal elbow plates 406p, 406d coupled to one another by a torque tube 408, a plurality of cone rods 410A, 410B, 410C, and a cable tension plate 432. For clarity of illustration, the cables used to control movement of the distal wrist assembly 100, which cables extend through the proximal elbow assembly 400, are not shown in FIGS. 6A-6D. The cables that control movement of the distal elbow assembly 200 are also not shown in FIGS. 6A-6D. These cables are illustrated and described in detail below.

The construction and function of the proximal elbow assembly 400 is essentially identical to that of the distal elbow assembly 200, with the exceptions noted herein and shown in the drawings.

The proximal and distal retainer housings 402p, 402d can include cylindrical bodies having a plurality of passageways 412p, 412d formed therethrough for receiving the cables used to impart motion to the distal wrist assembly 100. The distal retainer housing 402d can also include passageways for receiving the cables used to impart motion to the distal elbow assembly 200. A cavity 414d sized to receive the proximal end 306 of the body assembly 300 can be formed in the distal retainer housing 402d, and can thus form a female coupling for engagement with the body assembly 300. A reduced diameter portion 414p of the proximal retainer housing 402p can be sized to be received within the distal end of the proximal wrist assembly 500, and can thus provide a male coupling for engagement with the proximal wrist assembly 500. The proximal and distal retainer housings 402p, 402d can be coupled to the proximal wrist assembly 500 and the body assembly 300, respectively, using any of a variety of techniques, such as a friction fit, weld joint, adhesives, screws, pins, rivets, and so forth. In addition, tension applied to the cables extending through the device 10 can augment the mating between the various assemblies thereof.

An enlarged diameter portion 416p of the proximal retainer housing can include a recess 418p that is sized to receive the proximal retainer insert 404p. The distal facing surface of the proximal retainer housing 402p can include three concavities 420p positioned around the periphery of the recess 418p. The three concavities 420p can be spaced evenly 120 degrees apart from one another about the circumference of the retainer housing 402p, and can be sized to receive the proximal conical tips 430p of corresponding cone rods 410.

The proximal retainer insert 404p can include a rectangular body having a shape that minors the recess 418p of the proximal retainer housing 402p, such that the retainer insert 404p can be positioned within the retainer housing 402p. The proximal retainer insert 404p can also include a plurality of through holes 424p which can serve as a guide channel for the various cables extending through the device 10. The through holes 424p can optionally be coated or lined with a friction reducing material to facilitate sliding of the cables therethrough. It will be appreciated that although the proximal retainer housing 402p and the proximal retainer insert 404p are shown as separate components, they can also be integrally formed with each other.

The distal retainer housing 402d and insert 404d are substantially identical to the proximal retainer housing 402p and insert 404p, except that they are flipped 180 degrees in the proximal-distal direction. In addition, as described above, the proximal retainer housing 402p can include a male coupling whereas the distal retainer housing 402d can provide a female coupling.

The proximal and distal elbow plates 408p, 408d can be coupled to one another via the torque tube 408, which can be mated to the center of the elbow plates. The torque tube 408 can be fixedly coupled or formed integrally with the proximal and distal elbow plates 408p, 408d such that rotational movement of the elbow plates relative to one another about the longitudinal axis of the torque tube 408 is prevented. The proximal and distal elbow plates 408p, 408d can be disk shaped bodies having a variety of openings formed therein. Three oval-shaped rod passages 426 can be formed in the elbow plates, through which the cone rods 410 can be slidably received. The three rod passages 426 can be spaced equally 120 degrees apart from one another about the circumference of the elbow plates. The size and oval shape of the passages 426 can permit the cone rods 410 to angle slightly radially towards and away from the center of the elbow plate, but prevent the rods from angling tangentially relative to the elbow plate. This allows for translational movement of the distal retainer housing 402d relative to the proximal retainer housing 402p, while preventing rotation of the distal retainer housing 402d relative to the proximal retainer housing 402p about the longitudinal axis of the torque tube 408. In other words, the elbow plates 406p, 406d and torque tube 408 can prevent the proximal elbow assembly 400 from twisting about the longitudinal axis of the torque tube 408.

The elbow plates 406p, 406d can also include a number of through holes 428 to allow passage of the various cables extending through the device 10.

The cone rods 410 can be substantially rigid, elongate, cylindrical bodies having conical tips 430p, 430d formed at the proximal and distal ends thereof. Each cone rod 410 can extend from the distal retainer housing 402d, where its distal tip 430d can be seated within a corresponding concavity 420d, through the proximal and distal elbow plates 406p, 406d, and into the proximal retainer housing 402p, where its proximal tip 430p can be seated within a corresponding concavity 420p. The cone rods 410 can be formed with conical tips to reduce friction as the rods are angled within the concavities 420p, 420d. The cone rods 410 can be free to slide relative to the proximal and distal elbow plates 406p, 406d, which serve to maintain a substantially parallel relationship between all three cone rods 410A, 410B, 410C at all times, regardless of how the proximal elbow assembly 400 is manipulated. The cone rods 410 can be substantially the same length and can be retained under compression within the concavities 420p, 420d formed in the proximal and distal retainer housings 402p, 402d by tension applied to the cables extending through the device 10.

The proximal elbow assembly 400 can also includes a cable tension plate 432. The tension plate 432 can be similar in construction to the proximal and distal elbow plates 406p, 406d, in that it can be substantially disk-shaped, rigidly coupled to the torque tube 408, and can include a plurality of oval-shaped rod passages 426 for receiving the cone rods 410 and a plurality of round through holes 428 for receiving the cables used to impart motion to the distal wrist assembly 100. As described in further detail below, cables extending through the device 10 can be coupled at various points to the cable tension plate 432. In particular, three cables used to control the distal elbow assembly 200 can be coupled to three tension screws 434A, 434B, 434C, which are threadably coupled to the tension plate 432. Accordingly, the tension of any one of the three cables can be adjusted by turning its corresponding tension screw 434.

Figure 6C:
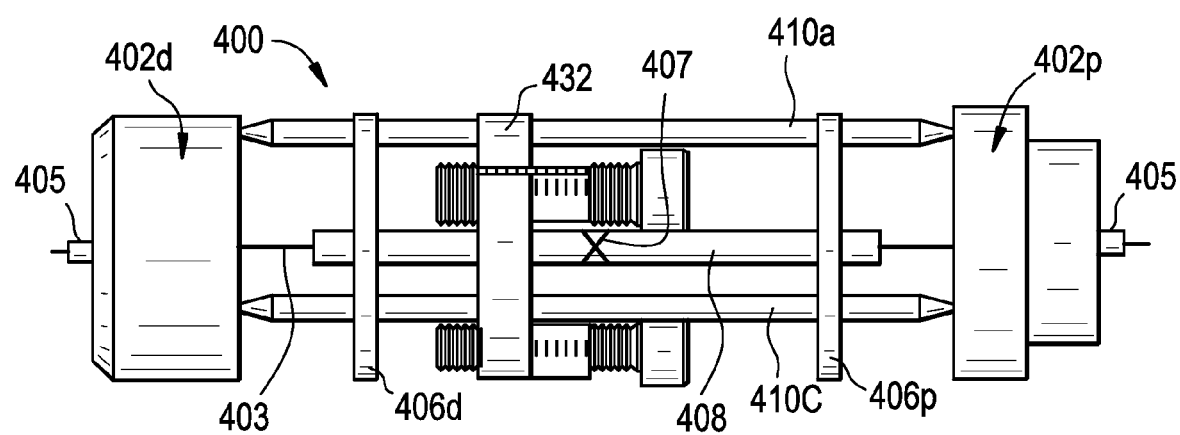
FIG. 6C is a side view of the proximal elbow assembly of FIG. 6A.
Figure 6D:
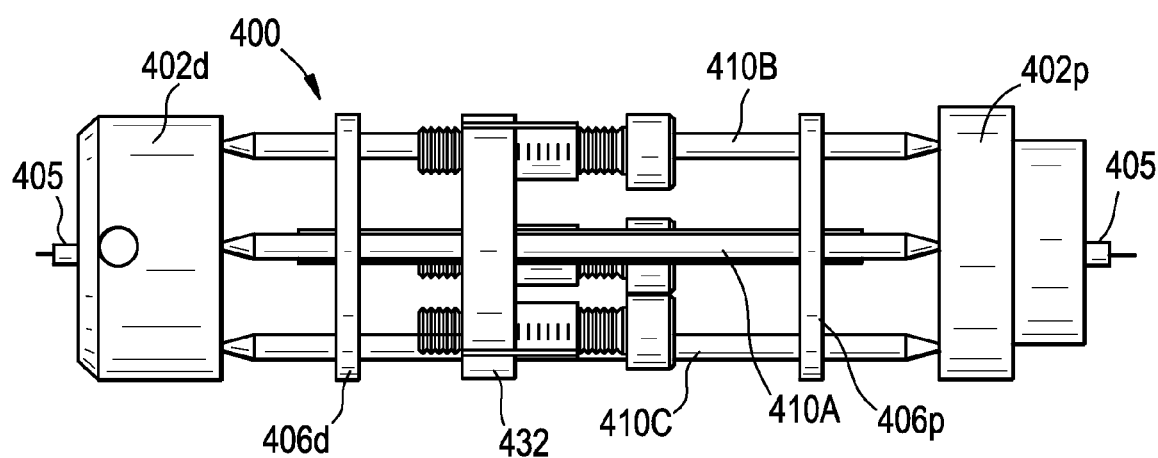
FIG. 6D is a top view of the proximal elbow assembly of FIG. 6A.
Figure 7A:
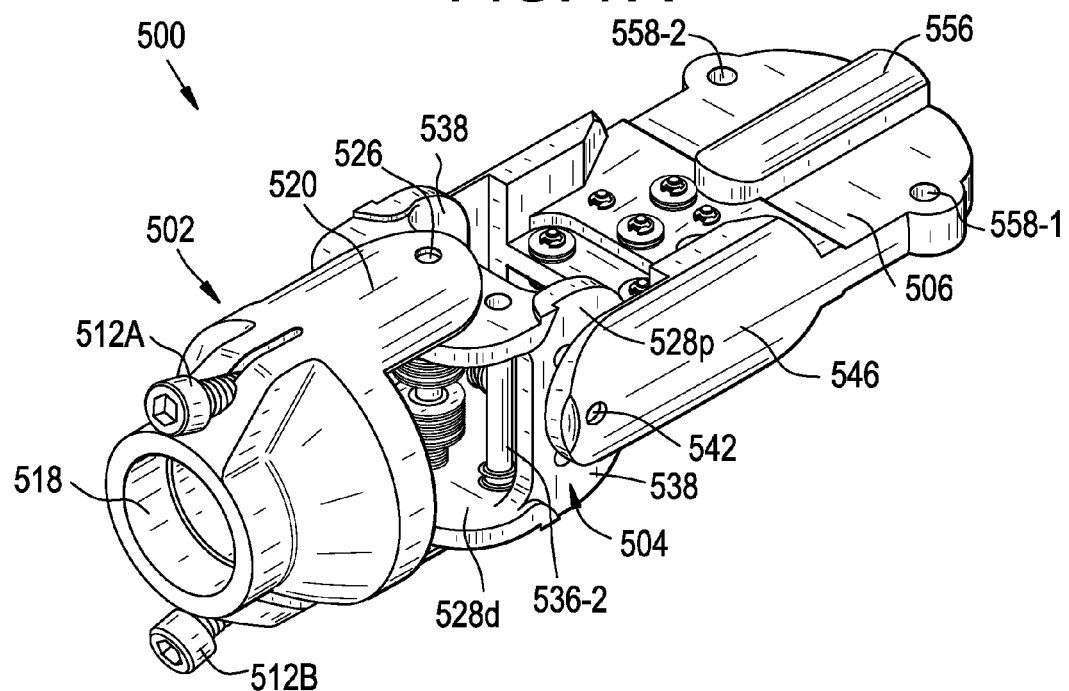
FIG. 7A is a perspective view of one embodiment of a proximal wrist assembly.
Figure 7B:
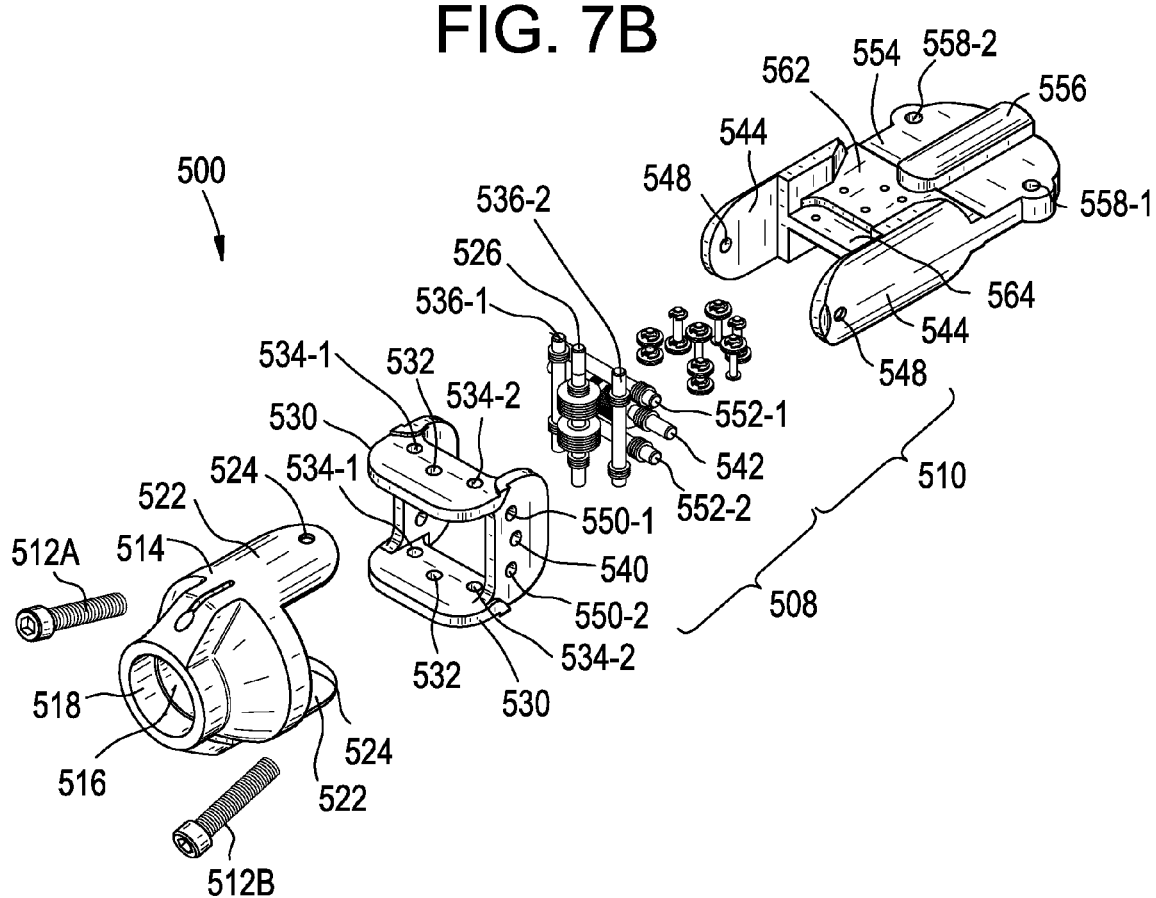
FIG. 7B is an exploded perspective view of the proximal wrist assembly of FIG. 7A.
Figure 7C:
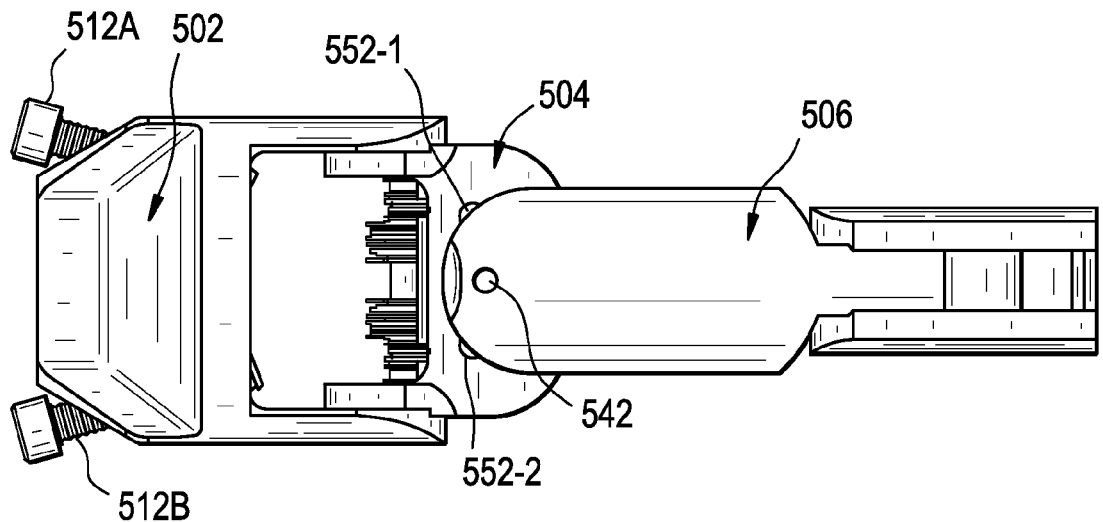
FIG. 7C is a side view of the proximal wrist assembly of FIG. 7A.
Figure 7D:
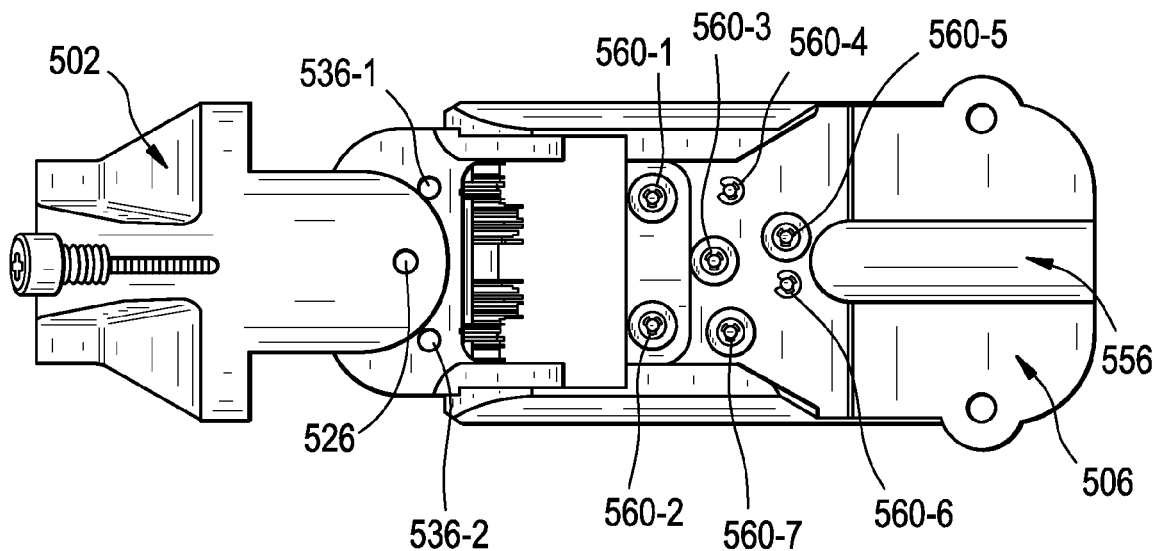
FIG. 7D is a top view of the proximal wrist assembly of FIG. 7A.

When the proximal retainer housing 402p moves laterally relative to the distal retainer housing 402d, the cone rods 410 tilt, causing the tension plate 432 to also move laterally and be angled relative to the distal retainer housing 402d. This results in tension being applied to one or more of the cables extending from the tension plate 432 while tension is simultaneously removed from one or more of the cables. In other words, one or more cables are pulled while one or more other cables are released. This pulling and releasing effects a lateral movement and angling of the proximal elbow plate 206p of the distal elbow assembly 200 relative to the proximal retainer housing 202p of the distal elbow assembly 200. Lateral motion of the proximal elbow assembly 400 is thus mirrored by lateral motion of the distal elbow assembly 200. This motion relationship is discussed in further detail below. As shown in FIGS. 6C and 6D, an anchor cable 403 can extend through the distal retainer housing 402d, the torque tube 408, and the proximal retainer housing 402p. First and second clips 405 can be crimped onto the ends of the anchor cable 403, adjacent to the proximal and distal retainer housings 402p, 402d. In addition, a center point 407 of the torque tube 408 can be crimped down around the anchor cable 403. The anchor cable 403 can thus be effective to maintain the torque tube 408 and the elbow plates 406p, 406d mounted thereto in a substantially fixed longitudinal position within the proximal elbow assembly 400 (e.g., approximately centered between the proximal and distal retainer housings 402p, 402d in the longitudinal direction).

Proximal Wrist Assembly

The proximal wrist assembly 500 is the "master" counterpart to the "slave" distal wrist assembly 100. The proximal wrist assembly 500 can provide a first pivot joint for pivoting the handle assembly 600 in the up-down direction (i.e., changing the pitch of the handle assembly 600) and a second pivot joint for pivoting the handle assembly 600 in the left-right direction (i.e. changing the yaw of the handle assembly 600). The proximal wrist assembly 500 can also include a plurality of pulleys for receiving the various cables that impart pitch (up-down) or yaw (left-right) pivot motion to the end effector assembly 108. Movement of the proximal wrist assembly 500 is mimicked by the distal wrist assembly 100 such that pivoting movement of components proximal to the proximal wrist assembly 500 is mimicked by components distal to the distal wrist assembly 100. This movement relationship is discussed in further detail below.

As shown in FIGS. 7A-7D, the proximal wrist assembly 500 can include a distal wrist frame 502, a central wrist frame 504, and a proximal wrist frame 506. The proximal wrist assembly 500 can also include a central pulley system 508 and a proximal pulley system 510, as well as first and second tension screws 512A, 512B. For clarity of illustration, the cables used to control movement of the distal wrist assembly 100, which cables extend through the proximal wrist assembly 500, are not shown in FIGS. 7A-7D. These cables are illustrated and described in detail below.

The distal wrist frame 502 can include a cylindrical body portion 514 that defines a central passageway 516 through which the control cables can be routed. The cylindrical body portion 514 can taper conically to a distal female receptacle 518, which can be sized to receive the reduced diameter proximal portion 414p of the proximal retainer housing 402p of the proximal elbow assembly 400. The proximal elbow assembly 400 can thus be coupled to the proximal wrist assembly 500. First and second tensions screws 512A, 512B are threadably received in the distal wrist frame 502, and can be rotated to adjust the tension applied to cables coupled thereto, as described further below.

A clevis 520 extending proximally from the cylindrical body portion 514 can be defined by a pair of opposed prongs 522 each prong having a through hole 524 formed therein for receiving a yaw (left-right) pivot pin 526.

The central wrist frame 504 can include a double clevis, the distal clevis 528d being oriented perpendicular to the proximal clevis 528p. The distal clevis 528d can include opposed prongs 530 having through holes 532 formed therein for receiving the yaw pivot pin 526 such that the central wrist frame 504 is rotatable about the yaw pivot pin 526 relative to the distal wrist frame 502. It will be appreciated that one of the central wrist frame 504 and the distal wrist frame 502 can be fixed to the yaw pivot pin 524, or that both the central wrist frame 504 and the distal wrist frame 502 can rotate relative to the yaw pivot pin 524. The distal clevis 528d can also include two pairs of through holes 534-1, 534-2 for receiving first and second vertical pulley axles 536-1, 536-2. The distal clevis 528d of the central wrist frame 504 can be sized to be received within the clevis 520 of the distal wrist frame 502 such that the distal wrist frame 502, central wrist frame 504, and yaw pivot pin 526 form a pivot joint about which the handle assembly 600 can be pivoted in the left-right direction (i.e., about which the yaw of the handle assembly 600 can be adjusted). The yaw pivot pin 526 can also serve as an axle for a plurality of pulleys, as detailed below.

The proximal clevis 528p of the central wrist frame 504 can include opposed prongs 538 having through holes 540 formed therein for receiving a pitch (up-down) pivot pin 542. The opposed prongs 538 can be sized to be received between opposed prongs 544 of a clevis 546 formed at the distal end of the proximal wrist frame 506. The opposed prongs 544 can also have through holes 548 formed therein for receiving the pitch pivot pin 542, such that the central wrist frame 504 is rotatable about the pitch pivot pin 542 relative to the proximal wrist frame 506. It will be appreciated that one of the central wrist frame 504 and the proximal wrist frame 506 can be fixed to the pitch pivot pin 542, or that both the central wrist frame 504 and the proximal wrist frame 506 can rotate relative to the pitch pivot pin 542. The proximal clevis 528p can also include two pairs of through holes 550-1, 550-2 for receiving first and second horizontal pulley axles 552-1, 552-2. Collectively, the proximal wrist frame 506, central wrist frame 504, and pitch pivot pin 542 form a pivot joint about which the handle assembly 600 can be pivoted in the up-down direction (i.e., about which the pitch of the handle assembly 600 can be adjusted). The pitch pivot pin 542 can also serve as an axle for a plurality of pulleys, as detailed below.

The proximal wrist frame 506 can include a generally rectangular body 554 having the clevis 546 described above extending distally therefrom. The proximal wrist frame 506 can also include a tubular female receptacle 556 at its proximal end for receiving the center link 632 of the handle assembly 600, as described below. First and second through holes 558-1, 558-2 can also be provided in the proximal wrist frame 506, adjacent to the tubular female receptacle 556, which each can receive a respective handle lever pivot pin 628A, 628B.

The proximal wrist frame 506 can also include seven through holes that receive seven corresponding idler pulley assemblies 560-1 through 560-7. Five of the idler pulley assemblies (560-3 through 560-7) can be received in through holes are formed in a main portion 562 of the proximal wrist frame 506. The other two idler pulley assemblies 560-1, 560-2 can be received in through holes formed in a recessed ledge potion 564 of the proximal wrist frame 506.

Figure 8:
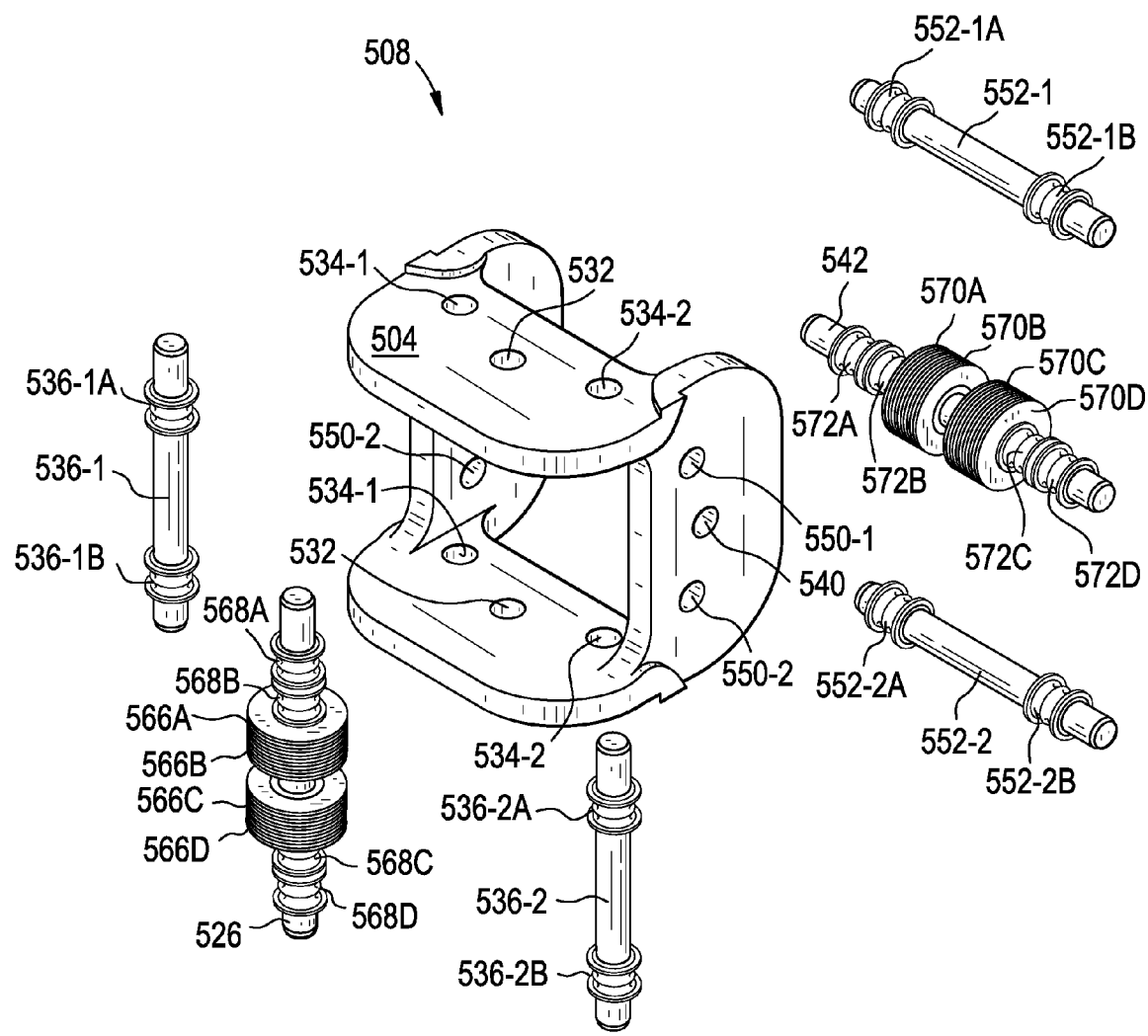
FIG. 8 is an exploded perspective view of the central pulley system of the proximal wrist assembly of FIG. 7A.

FIG. 8 illustrates the central pulley system 508 of the proximal wrist assembly 500 in more detail. As shown, the first vertical pulley axle 536-1 can include two idler pulleys 536-1A, 536-1B mounted thereon and can be mounted in through holes 534-1 formed in the central wrist frame 504. The second vertical pulley axle 536-2 can also include two idler pulleys 536-2A, 536-2B mounted thereon and can be mounted in through holes 534-2 formed in the central wrist frame 504. The yaw pivot pin 526 can include four major pulleys 566A, 566B, 566C, 566D and four minor pulleys 568A, 568B, 568C, 568D. The yaw pivot pin 526 can be mounted in through holes 532 formed in the central wrist frame 504.

As also shown in FIG. 8, the first horizontal pulley axle 552-1 can include two idler pulleys 552-1A, 552-1B mounted thereon and can be mounted in through holes 550-1 formed in the central wrist frame 504. The second horizontal pulley axle 552-2 can also include two idler pulleys 552-2A, 552-2B mounted thereon and can be mounted in through holes 550-2 formed in the central wrist frame 504. The pitch pivot pin 542 can include four major pulleys 570A, 570B, 570C, 570D and four minor pulleys 572A, 572B, 572C, 572D mounted thereon and can be mounted in through holes 540 formed in the central wrist frame 504.

Figure 9A:
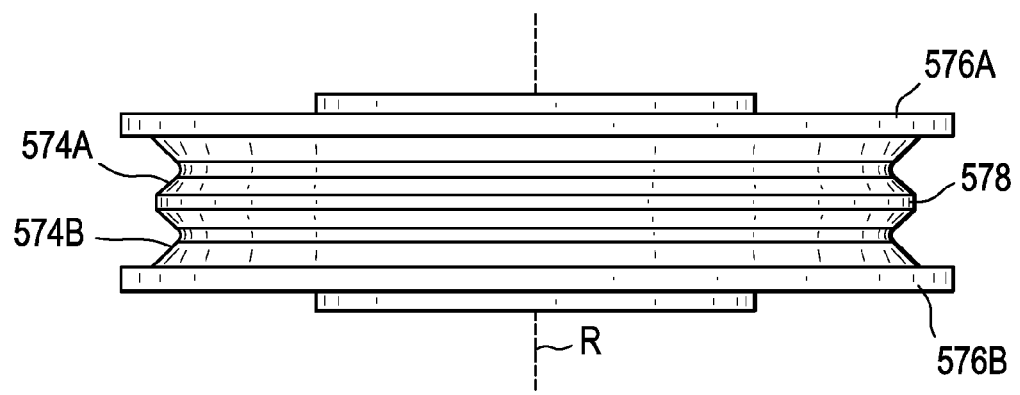
FIG. 9A is a side view of one embodiment of a pulley of the central pulley system of FIG. 8.
Figure 9B:
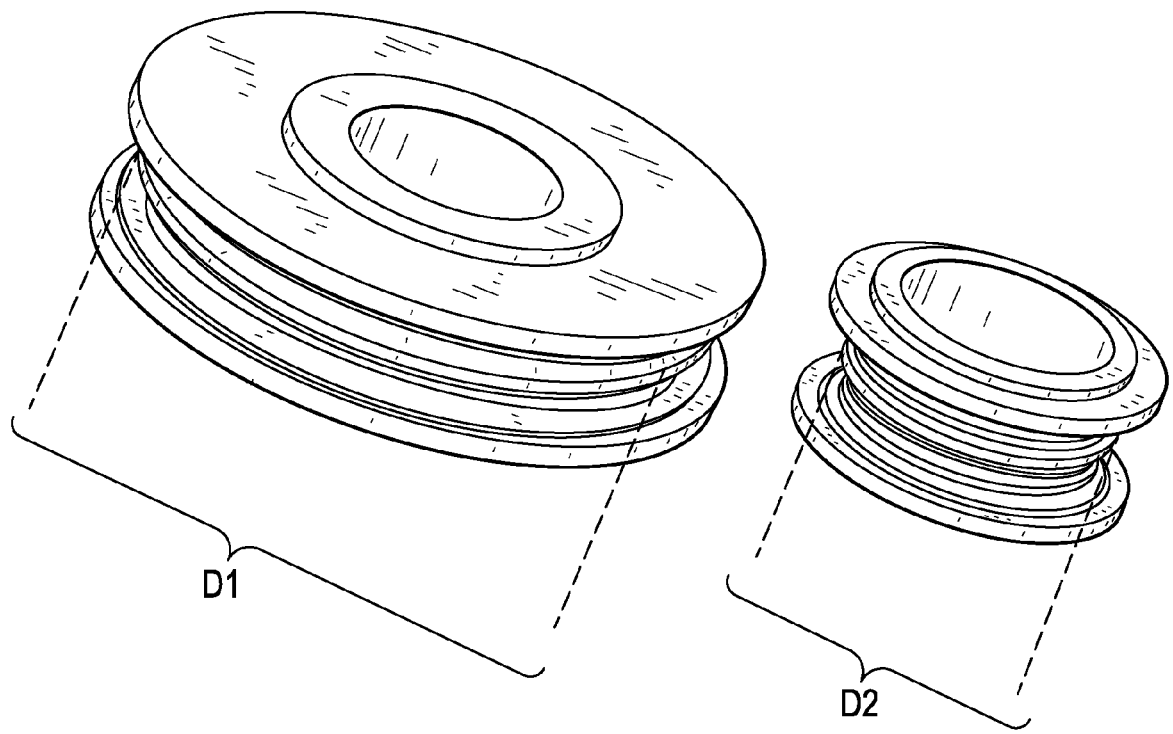
FIG. 9B is a perspective view of one embodiment of a major pulley and one embodiment of a minor pulley of the central pulley system of FIG. 8.

The pulleys of the central pulley system are shown in more detail in FIGS. 9A-9B. As shown, the pulleys can be generally cylindrical and can have a through hole formed along their central rotational axis R for receiving a pulley axle. The pulleys can be individually rotatable relative to their respective axles. Each pulley can have first and second V-shaped grooves or cable tracks 574A, 574B formed about the circumferential sidewall of the pulley. A pair of exterior retainer walls 576A, 576B can be positioned above and below the cable tracks 574A, 574B to prevent cables from slipping off of the pulley. The dividing wall 578 between the cable tracks can be rounded such that a single cable can be wound partially around the pulley in one track and then partially around the pulley in the other track. In other words, the cable can wrap onto the pulley in a first track, wrap partially around the pulley, cross over into the adjacent track, and then come back off of the pulley, such that the cable wraps 360 degrees around the pulley, approximately 180 degrees in the first track and approximately 180 degrees in the second track. It will be appreciated that the extent to which the cable wraps around the pulley is dictated in part by the degree to which the device 10 is articulated. In one embodiment, the cables are wrapped approximately 360 degrees around the pulleys when the device 10 is in a straight, non-articulated configuration. As the device 10 is articulated, more or less of the cable can be wrapped around the pulley. For example, in one embodiment, when the device 10 is fully articulated in a first direction, the cable can be wrapped 225 degrees around the pulley and when the device 10 is fully articulated in the opposite direction, the cable can be wrapped 495 degrees around the pulley.

This "double-winding" of cables around the pulleys provides a number of advantages. For example, the double-winding can help maintain enough contact radius between the cable and the pulley to keep the cable seated in the pulley when the pulley is moved during device manipulation. If not double-wound, the pulley systems of the device would require many more passive idler pulleys to keep the cables in their tracks. Otherwise, loss of contact radius between cable and pulley when the device is articulated could cause a cable to slip off of the pulley. By double-winding the cables, they can be prevented from slipping off of the pulleys without requiring the addition of several additional idler pulleys. This reduces the overall complexity of the device, and permits the pitch pivot pin 542 to be placed in very close proximity to the yaw pivot pin 526, minimizing wobble error. Wobble error is the deviation from a perfect spherical composite range of motion introduced when the pitch axis is offset from the yaw axis. Minimizing this offset reduces the wobble error and produces a tighter correspondence between master and slave motion.

As shown in FIG. 9B, the major pulleys can have a diameter D1 that is approximately twice the diameter D2 of the minor pulleys. This diameter ratio permits cables to be wound through the central pulley system 508 twice for tension compensation without skewing movement of the end effector assembly 108. This concept is described in further detail below. The guide pulleys 106A, 106B, 106C, 106D of the distal wrist assembly 100 (shown in FIGS. 3A-3D) can be substantially identical to the major pulleys shown in FIG. 9B, both in structure and dimension.

Figure 10A:
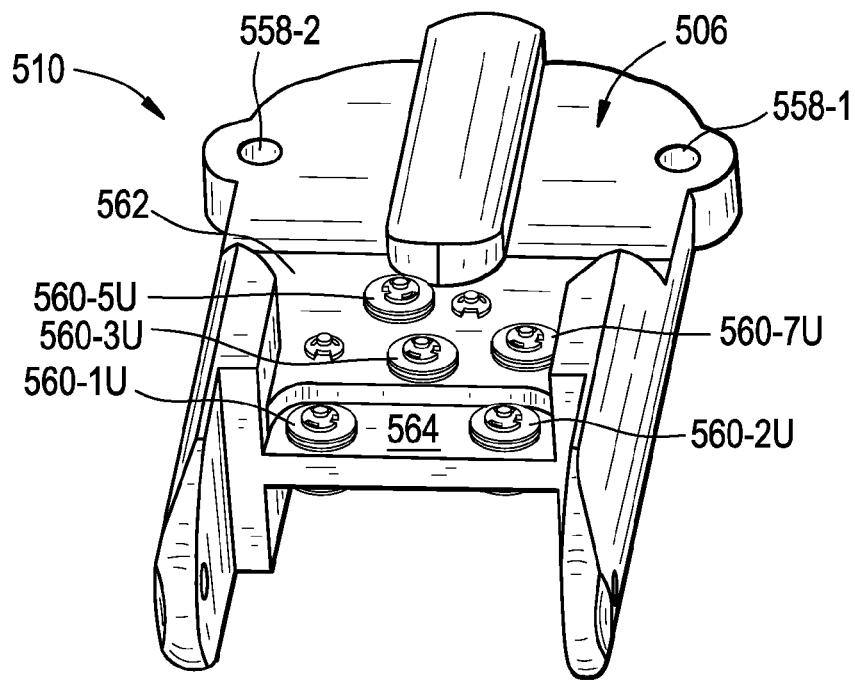
FIG. 10A is a perspective view from above of the proximal pulley system of the proximal wrist assembly of FIG. 7A.
Figure 10B:
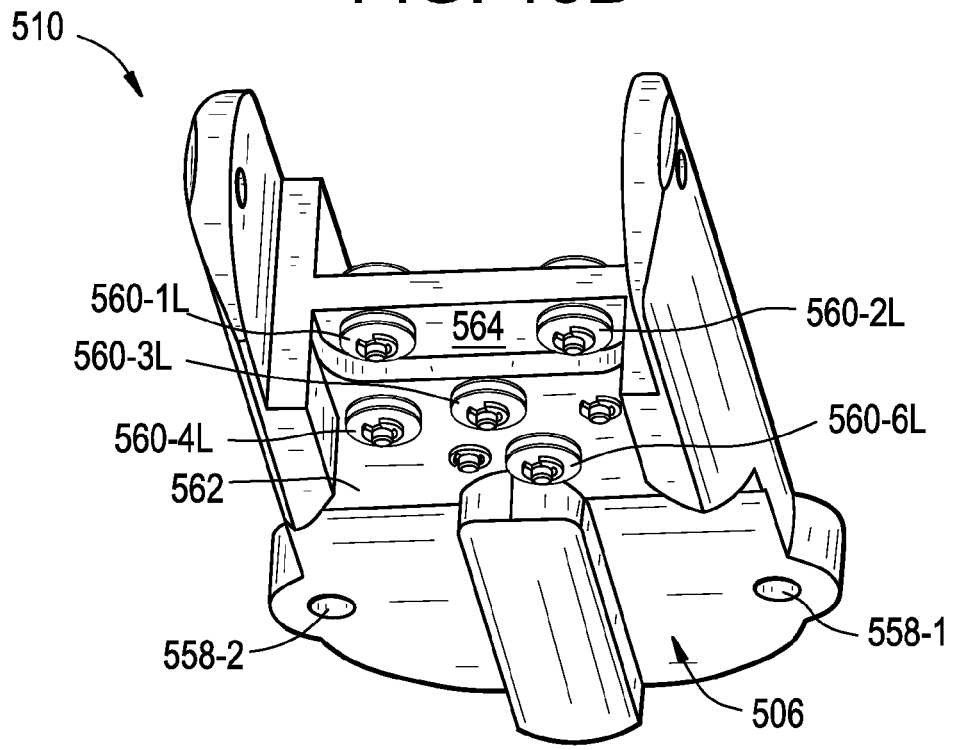
FIG. 10B is a perspective view from below of the proximal pulley system of the proximal wrist assembly of FIG. 7A.
Figure 10C:
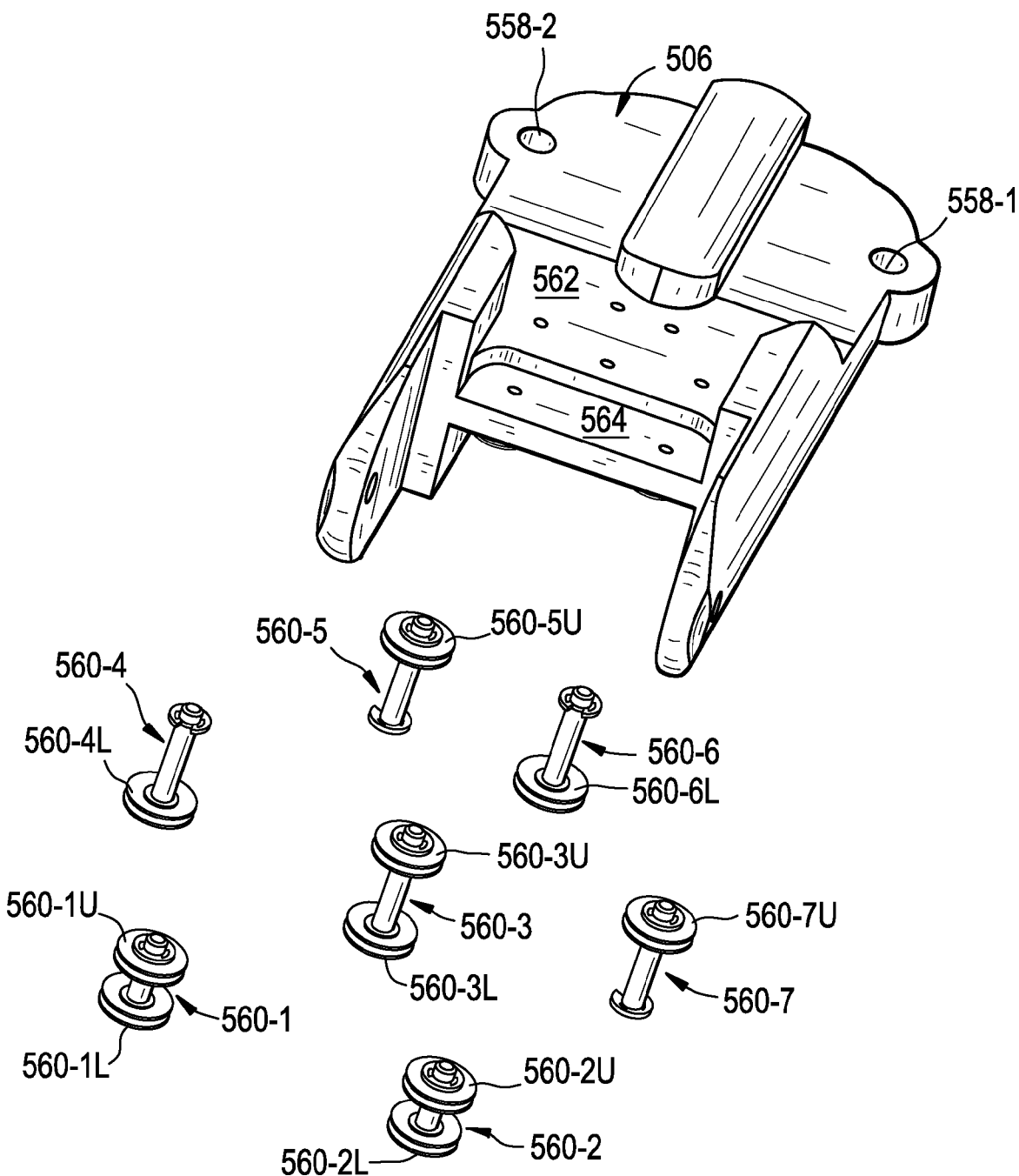
FIG. 10C is an exploded perspective view from above of the proximal pulley system of the proximal wrist assembly of FIG. 7A.

FIGS. 10A-10C illustrate the proximal pulley system 510 of the proximal wrist assembly 500 in more detail. As shown, the proximal pulley system 510 can be mounted to the proximal wrist frame 506 of the proximal wrist assembly 500. The proximal pulley system can generally include seven idler pulley assemblies 560-1 through 560-7, each having one or two idler pulleys, a pulley axle, and one or more c-clip retainers. FIG. 10A shows a top view of the proximal wrist frame 506, whereas FIG. 10B shows a bottom view. FIG. 10C is an exploded top view.

The first idler pulley assembly 560-1 extends through a through hole formed in the recessed ledge portion 564 of the proximal wrist frame 506. The first idler pulley assembly includes an upper pulley 560-1U that sits above the recessed ledge portion 564, and a lower pulley 560-1L that sits below the recessed ledge portion 564.

The second idler pulley assembly 560-2 extends through a through hole formed in the recessed ledge portion 564 of the proximal wrist frame 506. The second idler pulley assembly includes an upper pulley 560-2U that sits above the recessed ledge portion 564, and a lower pulley 560-2L that sits below the recessed ledge portion 564.

The third idler pulley assembly 560-3 extends through a through hole formed in the main portion 562 of the proximal wrist frame 506. The third idler pulley assembly includes an upper pulley 560-3U that sits above the main portion 562, and a lower pulley 560-3L that sits below the main portion 562.

The fourth idler pulley assembly 560-4 extends through a through hole formed in the main portion 562 of the proximal wrist frame 506. The fourth idler pulley assembly includes a lower pulley 560-4L that sits below the main portion 562.

The fifth idler pulley assembly 560-5 extends through a through hole formed in the main portion 562 of the proximal wrist frame 506. The fifth idler pulley assembly includes an upper pulley 560-5U that sits above the main portion 562.

The sixth idler pulley assembly 560-6 extends through a through hole formed in the main portion 562 of the proximal wrist frame 506. The sixth idler pulley assembly includes a lower pulley 560-6L that sits below the main portion 562.

The seventh idler pulley assembly 560-7 extends through a through hole formed in the main portion 562 of the proximal wrist frame 506. The seventh idler pulley assembly includes an upper pulley 560-7U that sits above the main portion 562.

The height of the pulleys of the first and second idler pulley assemblies 560-1, 560-2 can be selected such that the pulleys do not extend above the deck of the main potion 562 of the proximal wrist frame 506. This prevents interference between cables routed through the first and second idler pulley assemblies 560-1, 560-2 and cables routed through the third through seventh idler pulley assemblies 560-3 through 560-7.

Figure 11A:
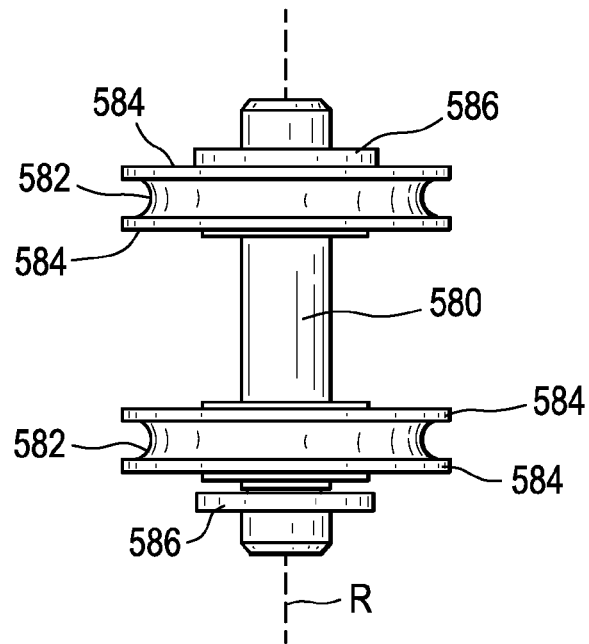
FIG. 11A is a side view of one embodiment of an idler pulley assembly of the proximal pulley system of FIG. 10A.
Figure 11B:
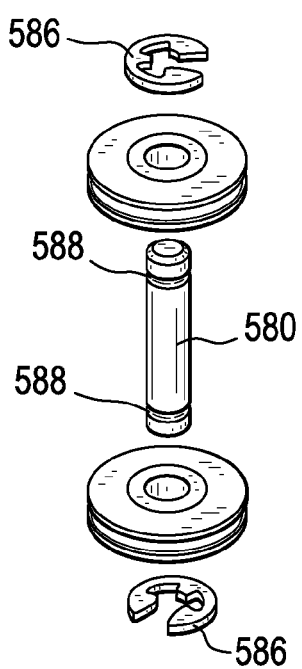
FIG. 11B is an exploded perspective view of the idler pulley assembly of FIG. 11A.
Figure 12A:
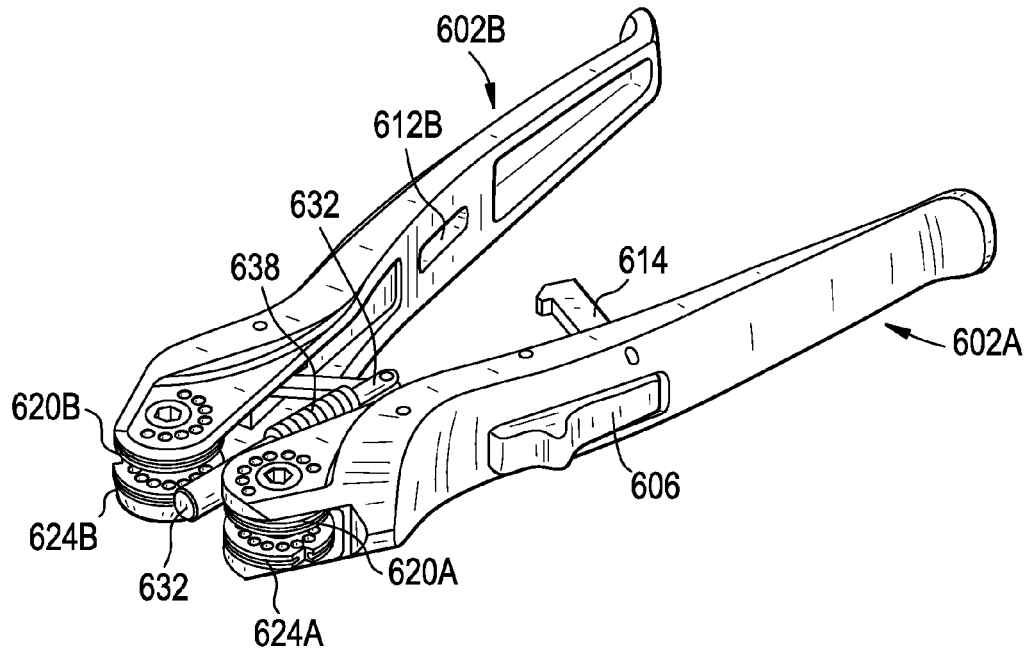
FIG. 12A is a perspective view of one embodiment of a handle assembly.
Figure 12B:
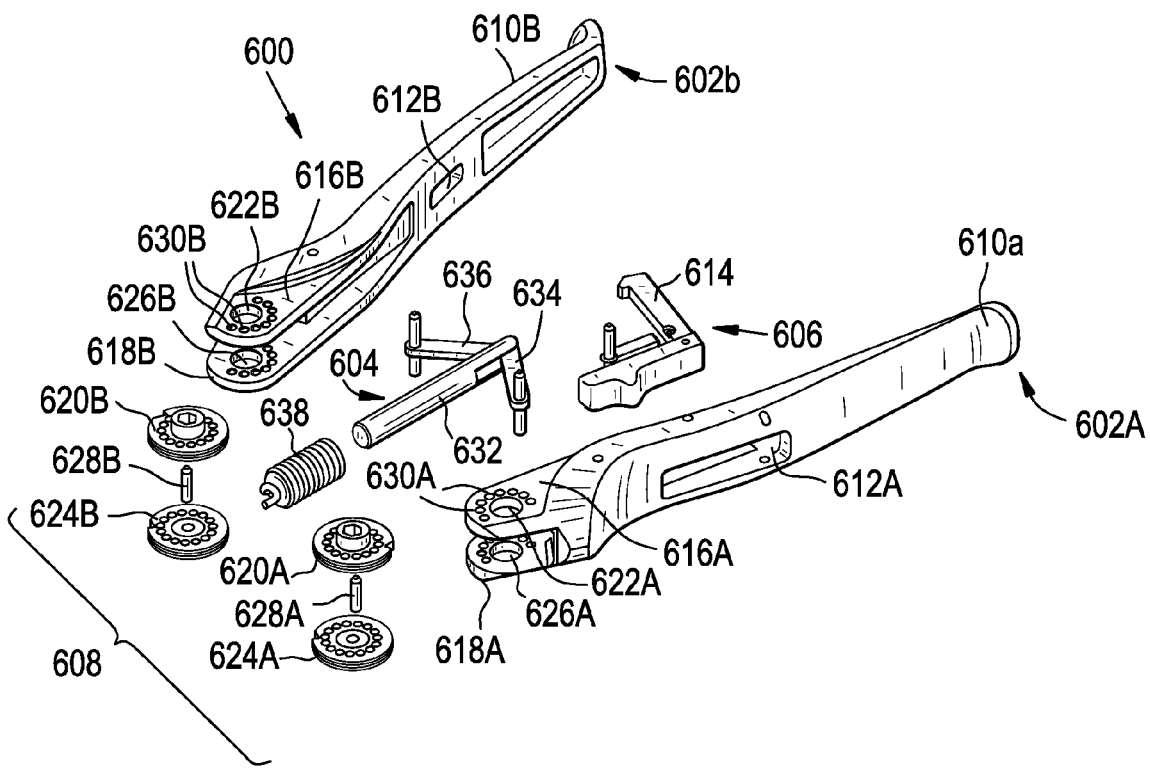
FIG. 12B is an exploded perspective view of the handle assembly of FIG. 12A.
Figure 12C:
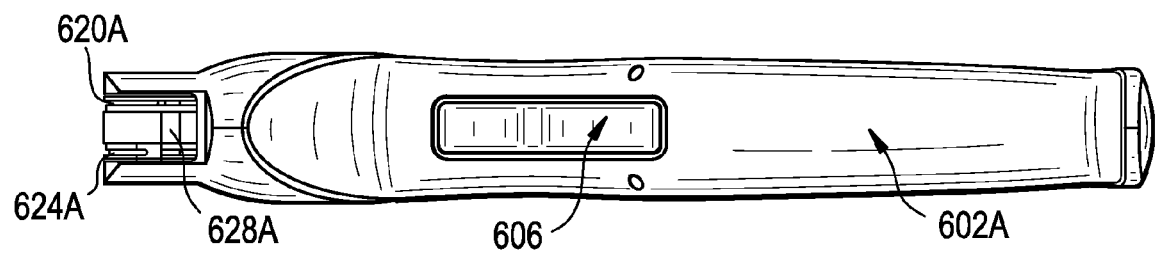
FIG. 12C is a side view of the handle assembly of FIG. 12A.
Figure 12D:
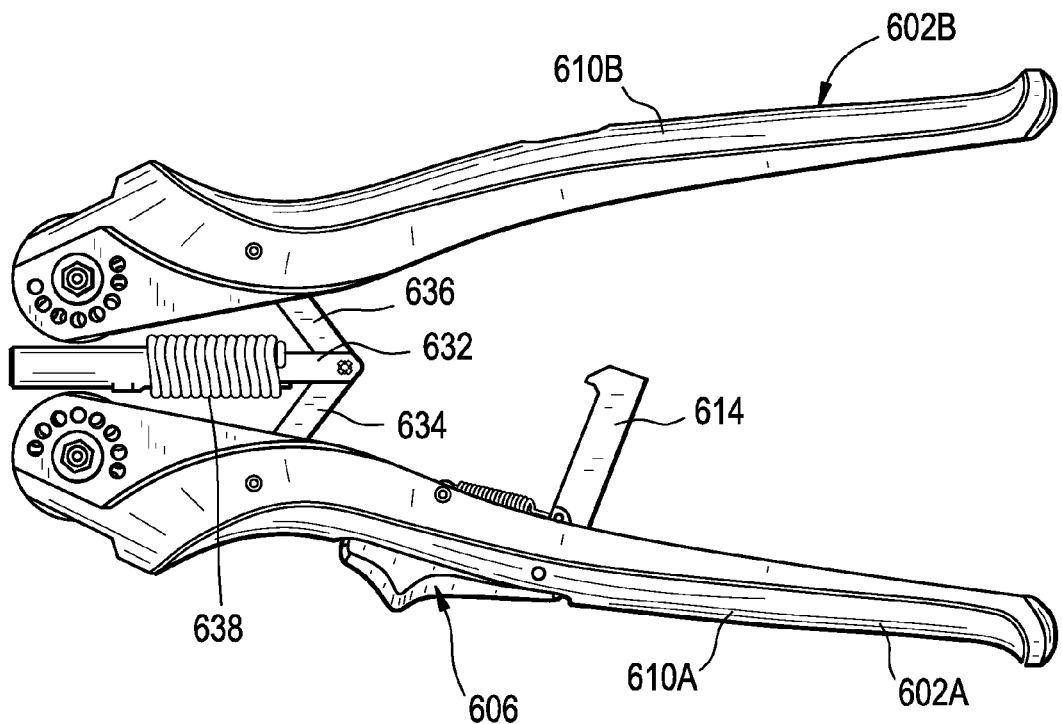
FIG. 12D is a top view of the handle assembly of FIG. 12A.

The pulleys of the proximal pulley system 510 are shown in more detail in FIGS. 11A-11B. As shown, the pulleys can be generally cylindrical and can have a through hole formed along their central rotational axis R for receiving a pulley axle 580. The pulleys can be individually rotatable relative to their respective axles. Since the pulleys of the illustrated proximal pulley system 510 are not double-wound, they include only a single cable track 582. A pair of exterior retainer walls 584 can be positioned above and below the cable track 582 to prevent cables from slipping off of the pulley. The pulleys can be slid onto the pulley axle 580 and retained by C-shaped retainer clips 586 that engage corresponding grooves 588 formed in the pulley axle 580.

Handle Assembly

The handle assembly 600 is the "master" counterpart to the "slave" end effector assembly 108. In other words, movement of the handle assembly 600 is mimicked and/or mirrored by the end effector assembly 108. This movement relationship is discussed in further detail below.

As shown in FIGS. 12A-12D, the handle assembly 600 can include first and second levers 602A, 602B, a biasing linkage assembly 604, a handle lock assembly 606, and a handle pulley system 608. For clarity of illustration, the cables used to control movement of the distal wrist assembly 100, which cables extend around the handle pulley system 608, are not shown in FIGS. 12A-12D. These cables are illustrated and described in detail below.

The first handle lever 602A can include a gripping portion 610A that can be contoured to provide an ergonomic gripping surface for a user. The handle lock assembly 606 can be mounted in a cutout 612A formed in the first handle lever 602A, and can include a spring biased locking hook 614 that can engage a corresponding cutout 612B formed in the second handle lever 602B to lock the handle levers 602A, 602B in a closed position (e.g., a position in which the handle levers are proximate to one another).

The distal end of the first handle lever 602A can include opposed prongs 616A, 618A in which half of the handle pulley system 608 can be received. In particular, a hub formed on the upper surface of an upper pulley 620A can be rotatably received within a through hole 622A formed in the upper prong 616A of the first handle lever 602A. Similarly, a hub formed on the lower surface of a lower pulley 624A can be rotatably received within a through hole 626A formed in the lower prong 618A of the first handle lever 602A. A handle lever pivot pin 628A can be positioned between the upper and lower pulleys 620A, 624A, providing a rotation axle for the pulleys and maintaining the pulleys in position spaced apart from one another. The handle lever pivot pin 628A can also be received in the through hole 558-1 formed in the proximal wrist frame 506 to couple the handle assembly 600 to the proximal wrist assembly 500.

The upper prong 616A of the first handle lever 602A can also include a plurality of tension adjustment holes 630A positioned circumferentially around the through hole 622A in which the upper pulley 620A is received. A locking pin (not shown) can be inserted through one of the tension adjustment holes 630A to lock the rotational orientation of the upper pulley 620A relative to the first handle lever 602A. The tension applied to a cable attached to the upper pulley 620A can be adjusted depending on which of the plurality of tension adjustment holes 630A the locking pin is inserted into. The lower prong 618A of the first handle lever 602A and the lower pulley 624A can include a similar tension adjustment system.

The second handle lever 620B can also provide a gripping portion 610B for the user, and can include a cutout 612B for receiving the locking hook 614 as described above. The second half of the handle pulley system 608 can be received within the distal end of the second handle lever 602B, and is identical in structure and function to the first half described above with respect to the first handle lever 602A.

The biasing linkage assembly 604 can be positioned between the first and second handle levers 602A, 602B, and can function to bias the handle levers 602A, 602B away from one another (e.g., towards a fully-opened position). The biasing linkage 604 can include a center link 632 that is slidably received within the tubular female receptacle 556 of the proximal wrist frame 506. The biasing linkage 604 can also include first and second side links 634, 636 that are pivotally coupled to the proximal end of the center link 632 and to the first and second handle levers 602A, 602B, respectively. A bias spring 638 can be fixedly coupled at its distal end to the proximal wrist frame 506 and at its proximal end to the center link 632. In operation, when the handle levers 602A, 602B are squeezed towards a closed position, the side links 634, 636 pivot in a proximal direction relative to the handle levers, causing the center link 632 to slide proximally within the tubular female receptacle 556 and causing the bias spring 638 to stretch. The potential energy stored in the stretched spring 638 pulls the center link 632 distally when the force is removed from the handle levers 602A, 602B, causing the side links 634, 636 to pivot in a distal direction relative to the handle levers, which in turn causes the handle levers to spread apart towards an open position.

Figure 13A:
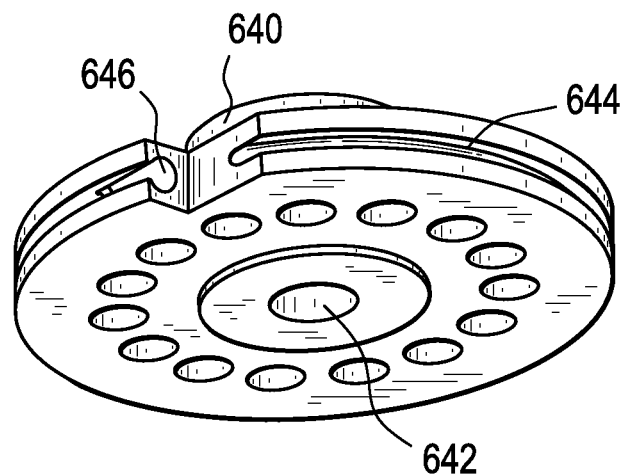
FIG. 13A is a perspective view of one embodiment of a handle pulley of the handle assembly of FIG. 12A.
Figure 13B:
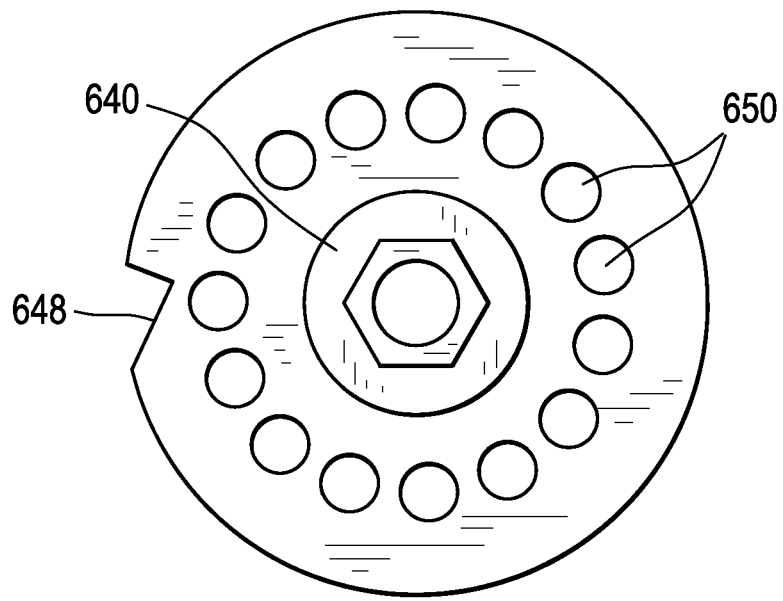
FIG. 13B is a top view of the handle pulley of FIG. 13A.

The pulleys of the handle pulley system are shown in more detail in FIGS. 13A-13B. As shown, the pulleys can be generally cylindrical. A raised hub 640 can be formed on one surface of the pulley and can be sized to rotate within a corresponding through hole formed in the handle levers 602A, 602B, as explained above. A receptacle 642 can be formed on the opposite side of the pulley for receiving a handle pivot pin 628A, 628B. Since the pulleys of the proximal pulley system are not double-wound in the illustrated embodiment, they include only a single cable track 644. The cable track can flare outward at one location along its length to form a cavity 646. The pulley can include a cross cut 648 adjacent to the cavity 646 such that the cavity can receive a cable termination (e.g., a ball or crimp). The cable termination can be small enough to at least partially fit within the cavity 646, but large enough so as not to pass into the remainder of the cable track 644. Accordingly, when a cable wound around the pulley is placed under tension, a cable termination attached thereto can be held in a fixed position along the circumference of the cable track 644. The handle pulleys can also include a plurality of tension adjustment holes 650 spaced circumferentially around the hub 640, which can be configured to receive one or more locking pins as explained above to adjust a rotational position of the pulley relative to the handle lever and thereby adjust the tension applied to a cable wound around the pulley.

Cable System Generally

Movement imparted by a user to the "master" components (e.g., the handle assembly 600) at the proximal end of the device 10 is translated into corresponding movement of the "slave" components (e.g., the end effector assembly 108) at the distal end of the device using a plurality of cables. The cables can be logically divided into two groups. A first group of six wrist cables can control up-down pivoting movement (pitch) of the slave components, left-right pivoting movement (yaw) of the slave components, and actuation of the slave components (e.g., opening and closing of the end effector jaws). A second group of three elbow cables can control up-down translational movement (heave) of the slave components and left-right translational movement of the slave components (sway).

Wrist Cables and Operation

The six wrist cables can include (1) an "up" cable, (2) a "down" cable, (3) a "left" first jaw cable, (4) a "right" first jaw cable, (5) a "left" second jaw cable, and (6) a "right" second jaw cable. The up and down wrist cables can extend from the proximal clevis prongs 130A, 130B of the second wrist frame 104 in the distal wrist assembly 100 and through the distal elbow assembly 200, the body assembly 300, the proximal elbow assembly 400, and the proximal wrist assembly 500, where they can be terminated. The four left and right wrist cables can extend from the first and second major jaws 110A, 110B, through the distal elbow assembly 200, the body assembly 300, the proximal elbow assembly 400, and the proximal wrist assembly 500, and into the handle assembly 600, where they can be terminated. The paths of each of the six wrist cables are described in detail below. For clarity of illustration, a number of components of the device 10 are not shown in the figures that accompany this description. For example, in the figures corresponding to each particular cable, all other cables are not shown.

The first wrist cable 702 (i.e., the "up" cable) is shown in FIGS. 14A-14B. As shown in FIG. 14A, the terminal distal end 702d of the first wrist cable 702 is attached to the left prong 130B of the proximal clevis 126 of the second wrist frame 104 of the distal wrist assembly 100. The cable 702 is then wrapped over the integral pulley 134B and extends proximally through the retainer inserts 204*d*, 204*p* of the distal elbow assembly 200, through the outer housing 302 of the body assembly 300, and through the retainer inserts 404*d*, 404*p* of the proximal elbow assembly 400. As shown in FIG.14B, the cable then enters the proximal wrist assembly 500, which is shown from above. The cable enters the central pulley system 508 where it is wrapped counterclockwise around an upper minor pulley 568B on the yaw pivot pin 526 and then counterclockwise around the upper idler pulley 536-2A on the second vertical pulley axle 536-2. The cable then wraps clockwise around the left idler pulley 552-1B on the first horizontal pulley axle 552-1 and then clockwise around a minor pulley 572D on the pitch pivot pin 542. The cable then 702 extends into the proximal pulley system 510, where it wraps counterclockwise around the upper pulley 560-2U of the second pulley assembly 560-2 and then counterclockwise around the upper pulley 560-1U of the first pulley assembly 560-1 before extending back into the central pulley system 508. The cable 702 then wraps counterclockwise around a minor pulley 572B on the pitch pivot pin 542, counterclockwise around the right idler pulley 552-1A on the first horizontal pulley axle 552-1, and then counterclockwise around the upper minor pulley 536-1A on the first vertical pulley axle 536-1. The cable 702 then wraps counterclockwise around the other upper minor pulley 568A on the yaw pivot pin 526 and extends distally into the proximal wrist frame 506, where its proximal terminal end 702*p* is fixedly attached to the upper tension screw 512A.

In operation, when the proximal wrist frame 506 is pivoted downwards relative to the central wrist frame 504, the first wrist cable 702 is pulled, which causes the second wrist frame 104 to pivot upwards relative to the first wrist frame 102. Thus, when the nose or distal end of the handle assembly 600 is aimed upwards (i.e., by tilting the proximal end of the handle assembly down), the distal end of the end effector assembly 108 is likewise aimed upwards. In other words, upwards pivoting motion of the master is mimicked by upwards pivoting motion of the slave.

Figure 15A:
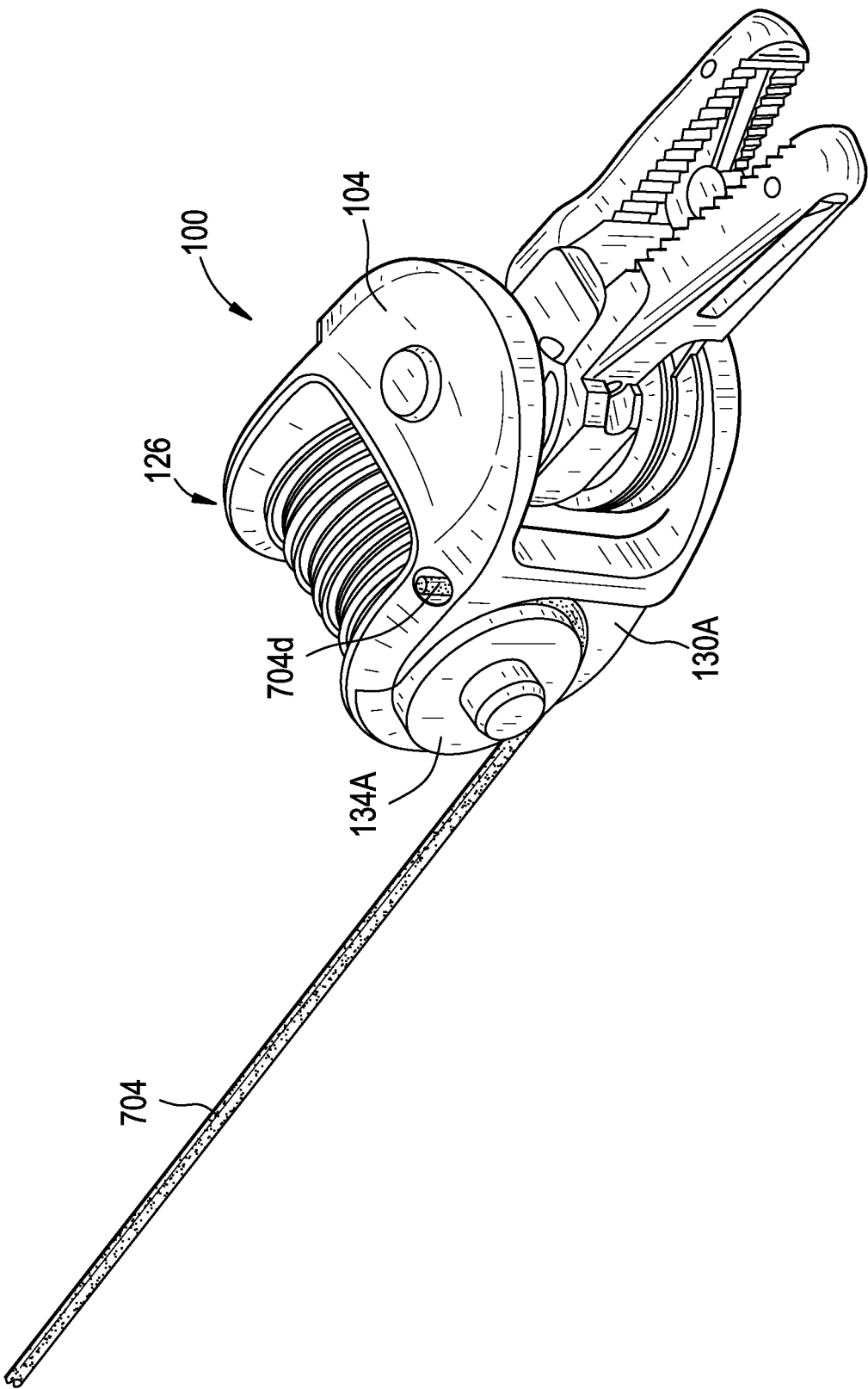
FIG. 15A is a perspective view of the distal path of a second wrist cable.
Figure 15B:
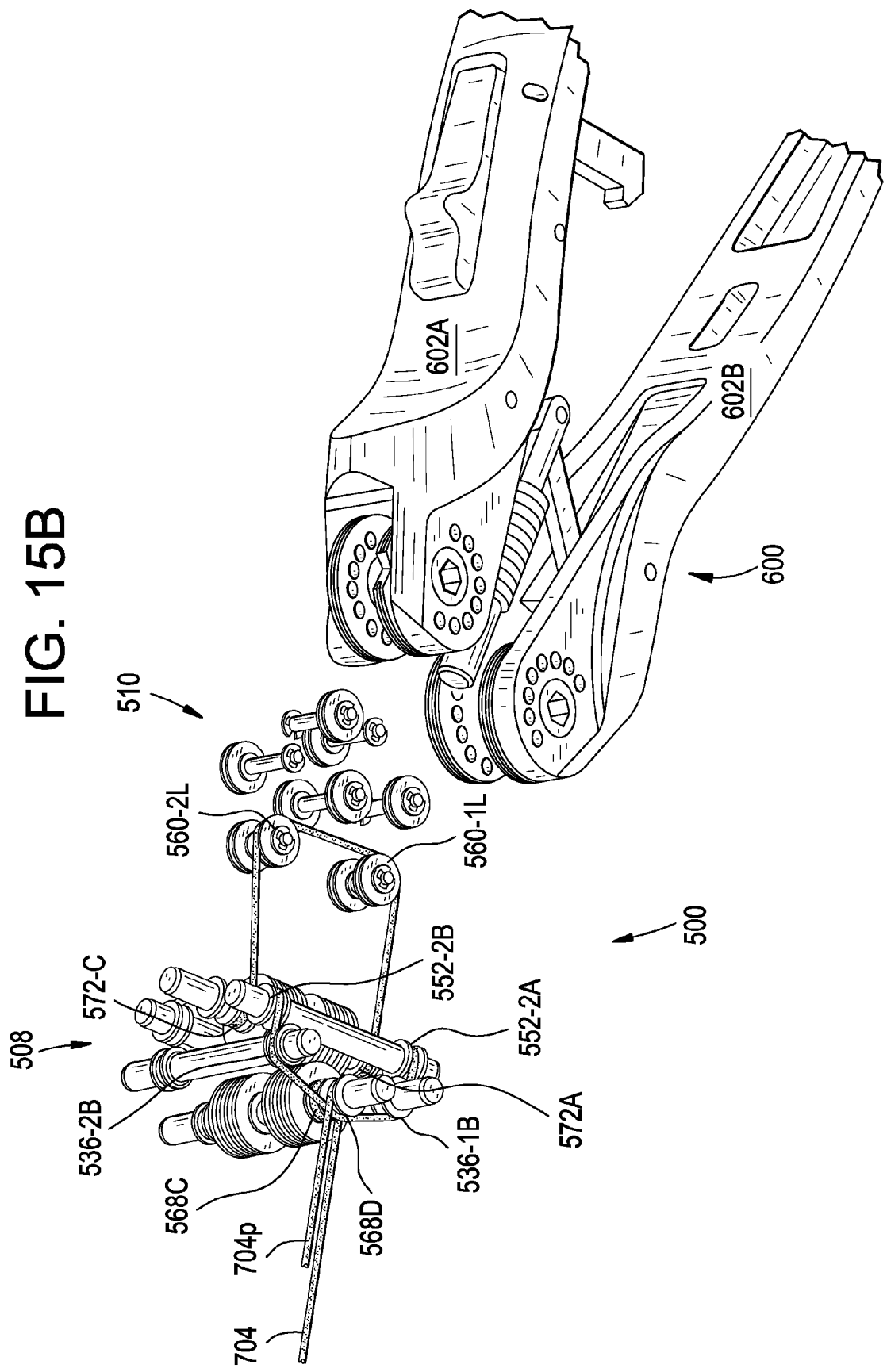
FIG. 15B is a perspective view of the proximal path of the second wrist cable of FIG. 15A.

The second wrist cable 704 (i.e., the "down" cable) is shown in FIGS. 15A-15B. As shown in FIG.15A, the terminal distal end 704*d* of the second wrist cable 704 is attached to the right prong 130A of the proximal clevis 126 of the second wrist frame 104 of the distal wrist assembly 100. The cable 704 is then wrapped under the integral pulley 134A and extends proximally through the retainer inserts 204*d*, 204*p* of the distal elbow assembly 200, through the outer housing 302 of the body assembly 300, and through the retainer inserts 404*d*, 404*p* of the proximal elbow assembly 400. As shown in FIG.15B, the cable 704 then enters the proximal wrist assembly 500, which is shown from below. The cable 704 enters the central pulley system 508 where it is wrapped clockwise around one of the lower minor pulleys 568C on the yaw pivot pin 526 and then clockwise around the lower idler pulley 536-1B on the first vertical pulley axle 536-1. The cable 704 then wraps counterclockwise around the right idler pulley 552-2A on the second horizontal pulley axle 552-2 and then counterclockwise around a minor pulley 572A on the pitch pivot pin 542. The cable 704 then extends into the proximal pulley system 510, where it wraps clockwise around the lower pulley 560-1L of the first pulley axle 560-1 and then clockwise around the lower pulley 560-2L of the second pulley axle 560-2 before extending back into the central pulley system 508. The cable 704 then wraps counterclockwise around a minor pulley 572C on the pitch pivot pin 542, clockwise around the left idler pulley 552-2B on the second horizontal pulley axle 552-2, and clockwise around the lower idler pulley 536-2B on the second vertical pulley axle 536-2. The cable 704 then wraps clockwise around the other lower minor pulley 568D on the yaw pivot pin 526 and extends distally into the proximal wrist frame 506, where its proximal terminal end 704*p* is fixedly attached to the lower tension screw 512B.

In operation, when the proximal wrist frame 506 is pivoted upwards relative to the central wrist frame 504, the second wrist cable 704 is pulled, which causes the second wrist frame 104 to pivot downwards relative to the first wrist frame 102. Thus, when the nose or distal end of the handle assembly 600 is aimed downwards (i.e., by tilting the proximal end of the handle assembly up), the distal end of the end effector assembly 108 is likewise aimed downwards. In other words, downwards pivoting motion of the master is mimicked by downwards pivoting motion of the slave.

The third wrist cable 706 (i.e., the "left" first jaw cable) is shown in FIGS. 16A-16B. As shown in FIG.16A, the terminal distal end 706*d* of the third wrist cable 706 is attached to the first major jaw 110A, where it is wound counterclockwise around the upper cable track 148A of the proximal cylindrical portion 142A. The cable 706 is then wrapped clockwise around a guide pulley 106C in the distal wrist assembly 100 before extending proximally through the retainer inserts 204*p*, 204*d* of the distal elbow assembly 200, through the outer housing 302 of the body assembly 300, and through the retainer inserts 404*p*, 404*d* of the proximal elbow assembly 400. As shown in FIG.16B, the cable 706 then enters the proximal wrist assembly 500, which is shown from above. The cable 706 enters the central pulley system 508 where it is wrapped counterclockwise around one of the upper major pulleys 566B on the yaw pivot pin 526 and then clockwise around one of the left major pulleys 570D of the pitch pivot pin 542. The cable 706 then extends into the proximal pulley system 510, where it wraps clockwise around the upper pulley 560-7U of the seventh pulley assembly 560-7 and then counterclockwise around the upper pulley 620A of the first handle lever 602A, where its terminal proximal end 706*p* is fixedly attached.

In operation, when the central wrist frame 504 is pivoted rightwards relative to the distal wrist frame 502, the third wrist cable 706 is pulled, which pulls the first major jaw 110A to the left. Thus, when the nose or distal end of the handle assembly 600 is aimed leftwards (i.e., by tilting the proximal end of the handle assembly to the right), the distal end of the first major jaw 110A is likewise aimed leftwards. In other words, leftwards pivoting motion of the master is mimicked by leftwards pivoting motion of the slave.

Figure 17B:
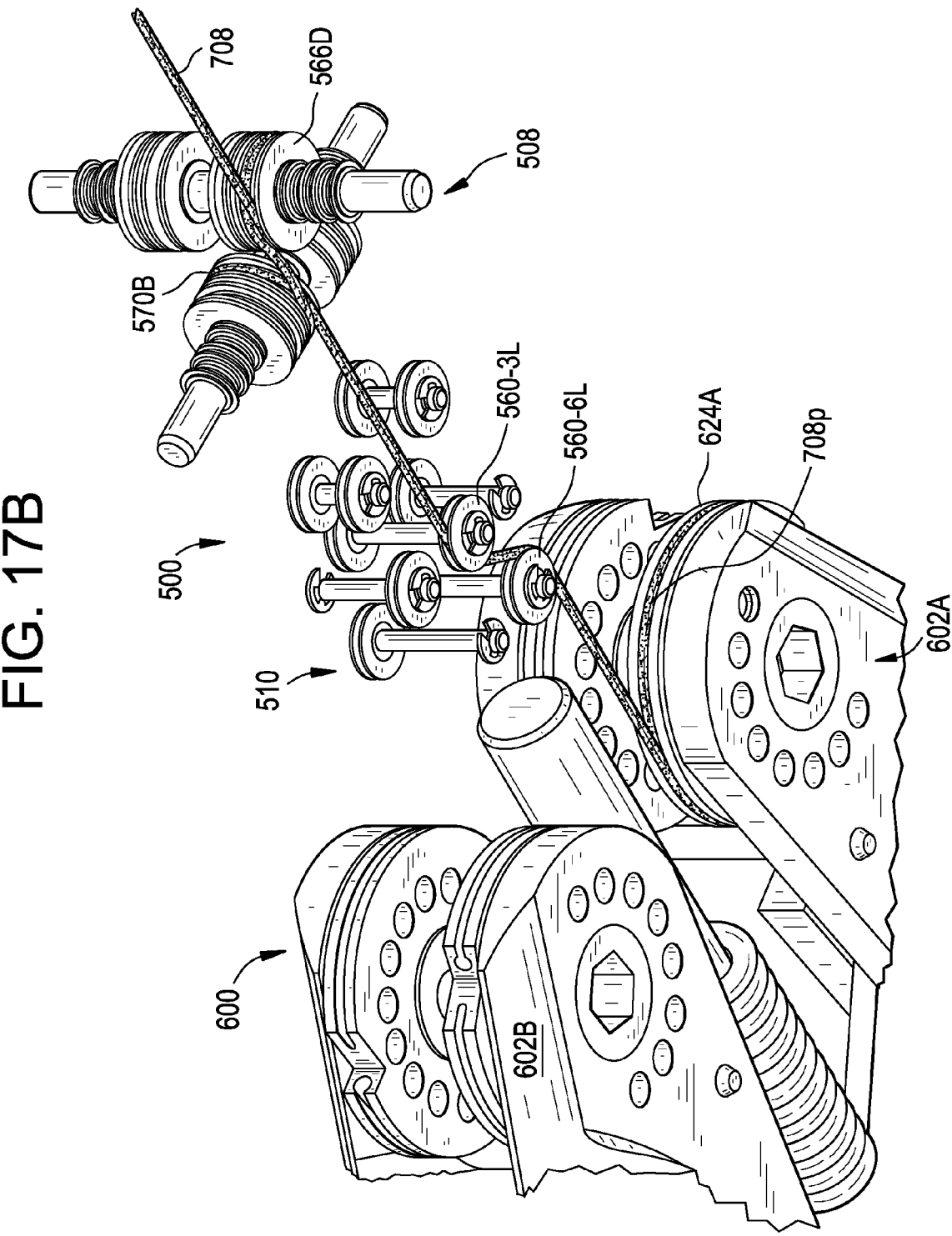
FIG. 17B is a perspective view of the proximal path of the fourth wrist cable of FIG. 17A.

The fourth wrist cable 708 (i.e., the "right" first jaw cable) is shown in FIGS. 17A-17B. As shown in FIG.17A, the terminal distal end 708*d* of the fourth wrist cable 708 is attached to the first major jaw 110A, where it is wound counterclockwise around the lower cable track 150A of the proximal cylindrical portion 142A. The cable 708 is then wrapped counterclockwise around a guide pulley 106B in the distal wrist assembly 100 before extending proximally through the retainer inserts 204*p*, 204*d* of the distal elbow assembly 200, through the outer housing 302 of the body assembly 300, and through the retainer inserts 404*p*, 404*d* of the proximal elbow assembly 400. As shown in FIG.17B, the cable 708 then enters the proximal wrist assembly 500, which is shown from below. The cable 708 enters the central pulley system 508 where it is wrapped clockwise around one of the lower major pulleys 566D on the yaw pivot pin 526 and then counterclockwise around one of the right major pulleys 570B of the pitch pivot pin 542. The cable 708 then extends into the proximal pulley system 510, where it wraps clockwise around the lower pulley 560-3L of the third pulley assembly 560-3, then counterclockwise around the lower pulley 560-6L of the sixth pulley assembly 560-6, and then finally clockwise around the lower pulley 624A of the first handle lever 602A, where its terminal proximal end 708p is fixedly attached.

In operation, when the central wrist frame 504 is pivoted leftwards relative to the distal wrist frame 502, the fourth wrist cable 708 is pulled, which pulls the first major jaw 110A to the right. Thus, when the nose or distal end of the handle assembly 600 is aimed rightwards (i.e., by tilting the proximal end of the handle assembly to the left), the distal end of the first major jaw 110A is likewise aimed rightwards. In other words, rightwards pivoting motion of the master is mimicked by rightwards pivoting motion of the slave.

It will be appreciated that instead of using two discrete cables, the third and fourth wrist cables 706, 708 can be replaced with a single cable, in which case the single cable can extend through a single cable track in the first major jaw 110A and the approximate midpoint of the single cable can be held in a fixed position relative to the first major jaw. This can be accomplished for example by threading the cable through an aperture in the cable track and forming crimps or knots in the cable which are unable to pass through the aperture. Where a single cable is used, it can be conceptualized as having a first length which acts as the third wrist cable and a second length which acts as the fourth wrist cable, the lengths extending proximally from the point where the cable is attached or fixed to the first major jaw.

Figure 18B:
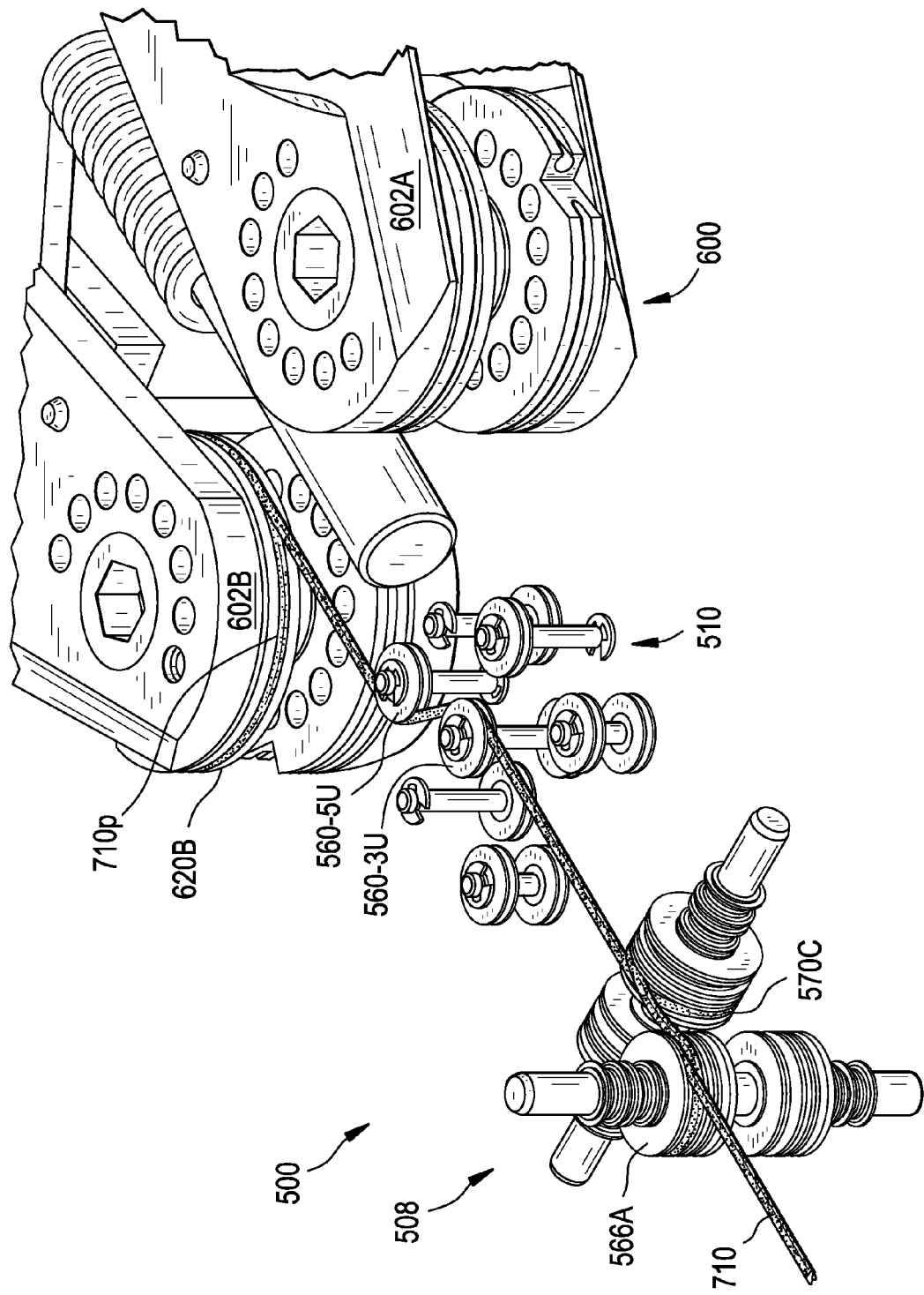
FIG. 18B is a perspective view of the proximal path of the fifth wrist cable of FIG. 18A.

The fifth wrist cable 710 (i.e., the "left" second jaw cable) is shown in FIGS. 18A-18B. As shown in FIG.18A, the terminal distal end 710d of the fifth wrist cable 710 is attached to the second major jaw 110B, where it is wound counterclockwise around the cable track 148B of the upper proximal cylindrical portion 142B. The cable 710 is then wrapped clockwise around a guide pulley 106D in the distal wrist assembly 100 before extending proximally through the retainer inserts 204p, 204d of the distal elbow assembly 200, through the outer housing 302 of the body assembly 300, and through the retainer inserts 404p, 404d of the proximal elbow assembly 400. As shown in FIG.18B, the cable 710 then enters the proximal wrist assembly 500, which is shown from above. The cable 710 enters the central pulley system 508 where it is wrapped counterclockwise around one of the upper major pulleys 566A on the yaw pivot pin 526 and then clockwise around one of the left major pulleys 570C of the pitch pivot pin 542. The cable 710 then extends into the proximal pulley system 510, where it wraps counterclockwise around the upper pulley 560-3U of the third pulley assembly 560-3, then clockwise around the upper pulley 560-5U of the fifth pulley assembly 560-5, and then finally counterclockwise around the upper pulley 620B of the second handle lever 602B, where its terminal proximal end 710p is fixedly attached.

In operation, when the central wrist frame 504 is pivoted rightwards relative to the distal wrist frame 502, the fifth wrist cable 710 is pulled, which pulls the second major jaw 110B to the left. Thus, when the nose or distal end of the handle assembly 600 is aimed leftwards (i.e., by tilting the proximal end of the handle assembly to the right), the distal end of the second major jaw 110B is likewise aimed leftwards. In other words, leftwards pivoting motion of the master is mimicked by leftwards pivoting motion of the slave.

The sixth wrist cable 712 (i.e., the "right" second jaw cable) is shown in FIGS. 19A-19B. As shown in FIG.19A, the terminal distal end 712d of the sixth wrist cable 712 is attached to the second major jaw 110B, where it is wound around the cable track 150B of the lower proximal cylindrical portion 142C. The cable 712 is then wrapped counterclockwise around a guide pulley 106A in the distal wrist assembly 100 before extending proximally through the retainer inserts 204p, 204d of the distal elbow assembly 200, through the outer housing 302 of the body assembly 300, and through the retainer inserts 404p, 404d of the proximal elbow assembly 400. As shown in FIG.19B, the cable 712 then enters the proximal wrist assembly 500, which is shown from below. The cable 712 enters the central pulley system 508 where it is wrapped clockwise around one of the lower major pulleys 566C on the yaw pivot pin 526 and then counterclockwise around one of the right major pulleys 570A of the pitch pivot pin 542. The cable 712 then extends into the proximal pulley system 510, where it wraps counterclockwise around the lower pulley 560-4L of the fourth pulley assembly 560-4, and then clockwise around the lower pulley 624B of the second handle lever 602B, where its terminal proximal end 712p is fixedly attached.

In operation, when the central wrist frame 504 is pivoted leftwards relative to the distal wrist frame 502, the sixth wrist cable 712 is pulled, which pulls the second major jaw 110B to the right. Thus, when the nose or distal end of the handle assembly 600 is aimed rightwards (i.e., by tilting the proximal end of the handle assembly to the left), the distal end of the second major jaw 110B is likewise aimed rightwards. In other words, rightwards pivoting motion of the master is mimicked by rightwards pivoting motion of the slave.

It will be appreciated that instead of using two discrete cables, the fifth and sixth wrist cables 710, 712 can be replaced with a single cable, in which case the single cable can extend through a single cable track in the second major jaw 110B and the approximate midpoint of the single cable can be held in a fixed position relative to the second major jaw. This can be accomplished for example by threading the cable through an aperture in the cable track and forming crimps or knots in the cable which are unable to pass through the aperture. Where a single cable is used, it can be conceptualized as having a first length which acts as the fifth wrist cable and a second length which acts as the sixth wrist cable, the lengths extending proximally from the point where the cable is attached or fixed to the second major jaw.

Figure 20A:
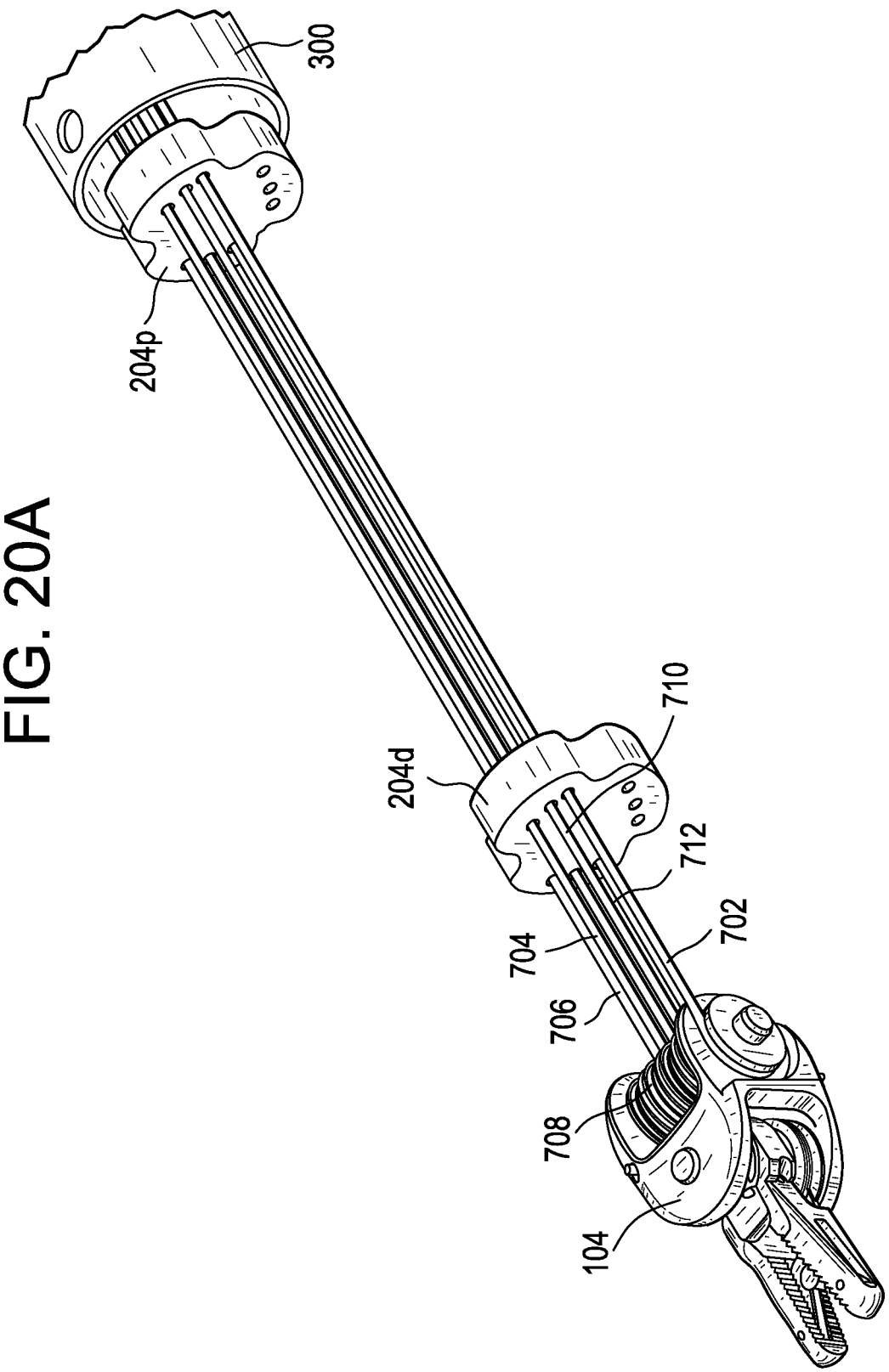
FIG. 20A is a perspective view of the distal paths of the first through sixth wrist cables of FIGS. 14A-19B.

FIGS. 20A-20B shows the various pulley systems of the device 10 with all six wrist cables visible.

In addition to controlling left and right pivoting motion of the end effector assembly 108, the third wrist cable 706, fourth wrist cable 708, fifth wrist cable 710, and sixth wrist cable 712 can also control actuation of the end effector assembly (e.g., opening and closing of the first and second major jaws 110A, 110B).

When the first and second handle levers 602A, 602B are squeezed towards one another, the third wrist cable 706 is wrapped further onto the upper pulley 620A of the first handle lever 602A, and the sixth wrist cable 712 is wrapped further onto the lower pulley 624B of the second handle lever 602B. At the same time, the fourth wrist cable 708 is partially unwrapped from the lower pulley 624A of the first handle lever 602A, and the fifth wrist cable 710 is partially unwrapped from the upper pulley 620B of the second handle lever 602B. In other words, the third and sixth wrist cables 706, 712 are pulled the fourth and fifth wrist cables 708, 710 are released. The tension applied to the third cable 706 pulls the first major jaw 110A to the left, while the tension applied to the sixth cable 712 pulls the second major jaw 110B to the right. Thus, the jaws 110A, 110B are pulled towards each other and towards a closed position.

When the first and second handle levers 602A, 602B are moved away from one another, the fourth wrist cable 708 is wrapped further onto the lower pulley 624A of the first handle lever 602A, and the fifth wrist cable 710 is wrapped further onto the upper pulley 620B of the second handle lever 602B. At the same time, the third wrist cable 706 is partially unwrapped from the upper pulley 620A of the first handle lever 602A, and the sixth wrist cable 712 is partially unwrapped from the lower pulley 624B of the second handle lever 602B. In other words, the fourth and fifth wrist cables 708, 710 are pulled while the third and sixth wrist cables 706, 712 are released. The tension applied to the fourth cable 708 pulls the first major jaw 110A to the right, while the tension applied to the fifth cable 710 pulls the second major jaw 110B to the left. Thus, the jaws 110A, 110B are pulled away from each other and towards an open position.

Tension Compensation

When yaw movement of the proximal wrist assembly 500 occurs, tension applied and/or removed from the third, fourth, fifth, and sixth wrist cables 706, 708, 710, 712 adjusts the yaw of the end effector assembly 108. This yaw movement of the proximal wrist assembly 500 can also produce incidental movement of the first and second wrist cables 702, 704 which, if not compensated for, could introduce unintended changes in the effective length of the first and second wrist cables 702, 704, and corresponding pitch adjustments of the end effector assembly 108. In other words, unless some compensation is provided, yaw movement of the master component can produce unintended pitch movement of the slave component, in addition to the intended yaw movement.

Similarly, when pitch movement of the proximal wrist assembly 500 occurs, tension applied and/or removed from the first and second wrist cables 702, 704 adjusts the pitch of the end effector assembly 108. This pitch movement of the proximal wrist assembly 500 can also produce incidental movement of the third, fourth, fifth, and sixth wrist cables 706, 708, 710, 712 which, if not compensated for, could introduce unintended changes in the effective length of these cables, and corresponding yaw adjustments of the end effector assembly 108. In other words, unless some compensation is provided, pitch movement of the master component can produce unintended yaw movement of the slave component, in addition to the intended pitch movement.

The device 10 can compensate for incidental movement of "non-active" pitch cables by running the first and second cables 702, 704 through the central pulley system 508 twice in opposite directions. Thus, referring for example to FIGS. 14A-14B, when yaw movement occurs that would otherwise tend to apply incidental tension to the first cable 702, the first cable 702 is simultaneously wrapped onto one of the minor pulleys 572D, 572B of the pitch pivot pin 542 and unwrapped from another of the minor pulleys 572D, 572B of the pitch pivot pin 542. The first cable 702 is also simultaneously wrapped onto one of the minor pulleys 568A, 568B on the yaw pivot pin 526 and unwrapped from another of the minor pulleys 568A, 568B on the yaw pivot pin 526. Accordingly, the net movement of the distal terminal end 702d of the first cable 702 is zero. In other words, as the pulley 560-2U pulls the cable 702 out of the central pulley system 508 during yaw articulation, the pulley 560-1U feeds the cable 702 back into the central pulley system, and vice versa. The same is true for the second cable 704. This prevents inadvertent pitch movement when only yaw movement is intended.

As noted above, the minor pulleys over which the first and second cables 702, 704 are wound can have a diameter that is one half the diameter of the major pulleys over which the third, fourth, fifth, and sixth cables 706, 708, 710, 712 are wound. This prevents the routing of the first and second cables through the central pulley system 508 twice from scaling pitch movement differently from yaw movement. In other words, if the pulleys were the same size, yaw of the master would be mapped 1:1 to the slave, whereas pitch movement of the master would be mapped 2:1 to the slave by virtue of the first and second cables being wrapped over twice as much pulley radius as the third, fourth, fifth, and sixth cables.

The device 10 can also compensate for incidental movement of "non-active" yaw cables during pitch articulation. Referring for example to FIGS. 16A-16B, when pitch movement occurs that would otherwise tend to apply incidental tension to the third cable 706, the third cable 706 is simultaneously wrapped onto one of the major pulleys 570D of the pitch pivot pin 542 and unwrapped from one of the guide pulleys 106C of the pitch pivot pin 124. In other words, as the cable 706 wraps onto the pulley 570D during pitch movement of the handle assembly 600, the pitch of the distal wrist assembly 100 changes, causing the cable 706 to unwrap from the guide pulley 106C. Similarly, as the cable 706 unwraps from the pulley 570D during pitch movement of the handle assembly 600 in the opposite direction, the pitch of the distal wrist assembly 100 changes in the opposite direction, causing the cable 706 to wrap onto the guide pulley 106C. Accordingly, the net movement of the distal terminal end 706d of the third cable 706 is zero in either case. This prevents inadvertent yaw movement when only pitch movement is intended. A similar effect occurs with the fourth, fifth, and sixth cables 708, 710, 712.

Elbow Cables and Operation

As noted above, the six wrist cables can control up-down pivoting movement (pitch) of the slave components, left-right pivoting movement (yaw) of the slave components, and actuation of the slave components (opening and closing of the end effector jaws). The three elbow cables, on the other hand, can control up-down translational movement (heave) of the slave components and left-right translational movement (sway) of the slave components.

The three elbow cables 714, 716, 718 can extend from the proximal elbow plate 206p of the distal elbow assembly 200, through the body assembly 300, to the tension plate 432 of the proximal elbow assembly 400.

The paths of each of the three elbow cables 714, 716, 718 are described in detail below. For clarity of illustration, a number of components of the device 10 are not shown in the figures that accompany this description. For example, in the figures corresponding to each particular cable, all other cables are not shown. Also, for clarity of illustration, the proximal elbow plate 206p and the tension plate 432 are shown in close proximity to one another, however it will be appreciated that in fact these components can be separated in the longitudinal direction by the body assembly 300 and other intervening components of the device 10, as described above.

Figure 21A:
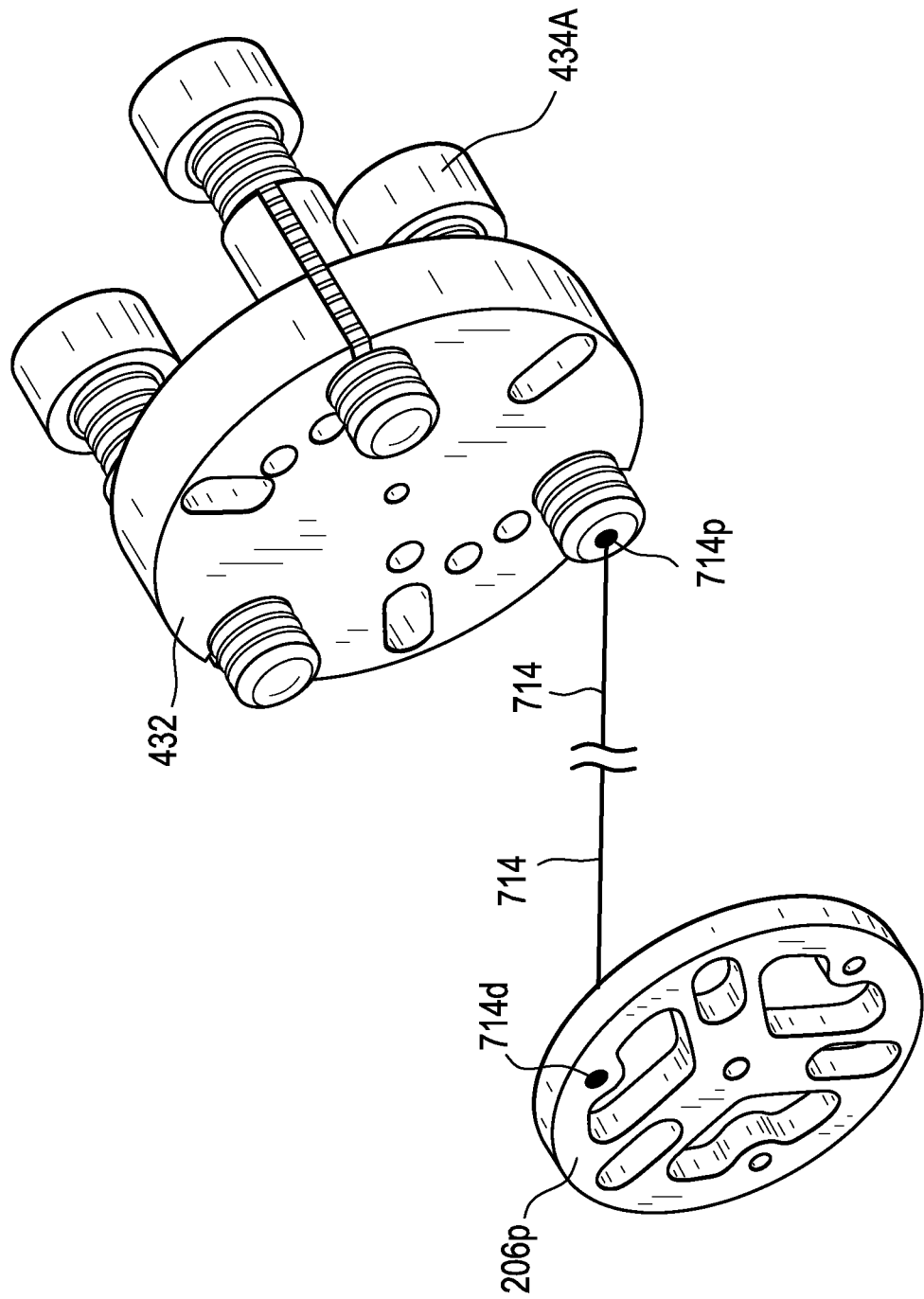
FIG. 21A is a perspective schematic view of the path of a first elbow cable.

The first elbow cable 714 is shown in FIG. 21A. As shown, the terminal distal end 714d of the cable is coupled to a first attachment point on the proximal elbow plate 206p of the distal elbow assembly 200. The terminal proximal end 714p of the cable 714 is coupled to a first attachment point on the tension plate 432 (e.g., a first tension screw 434A). As shown, the first attachment point on the proximal elbow plate 206p is rotationally offset 180 degrees from the first attachment point on the tension plate 432.

Figure 21B:
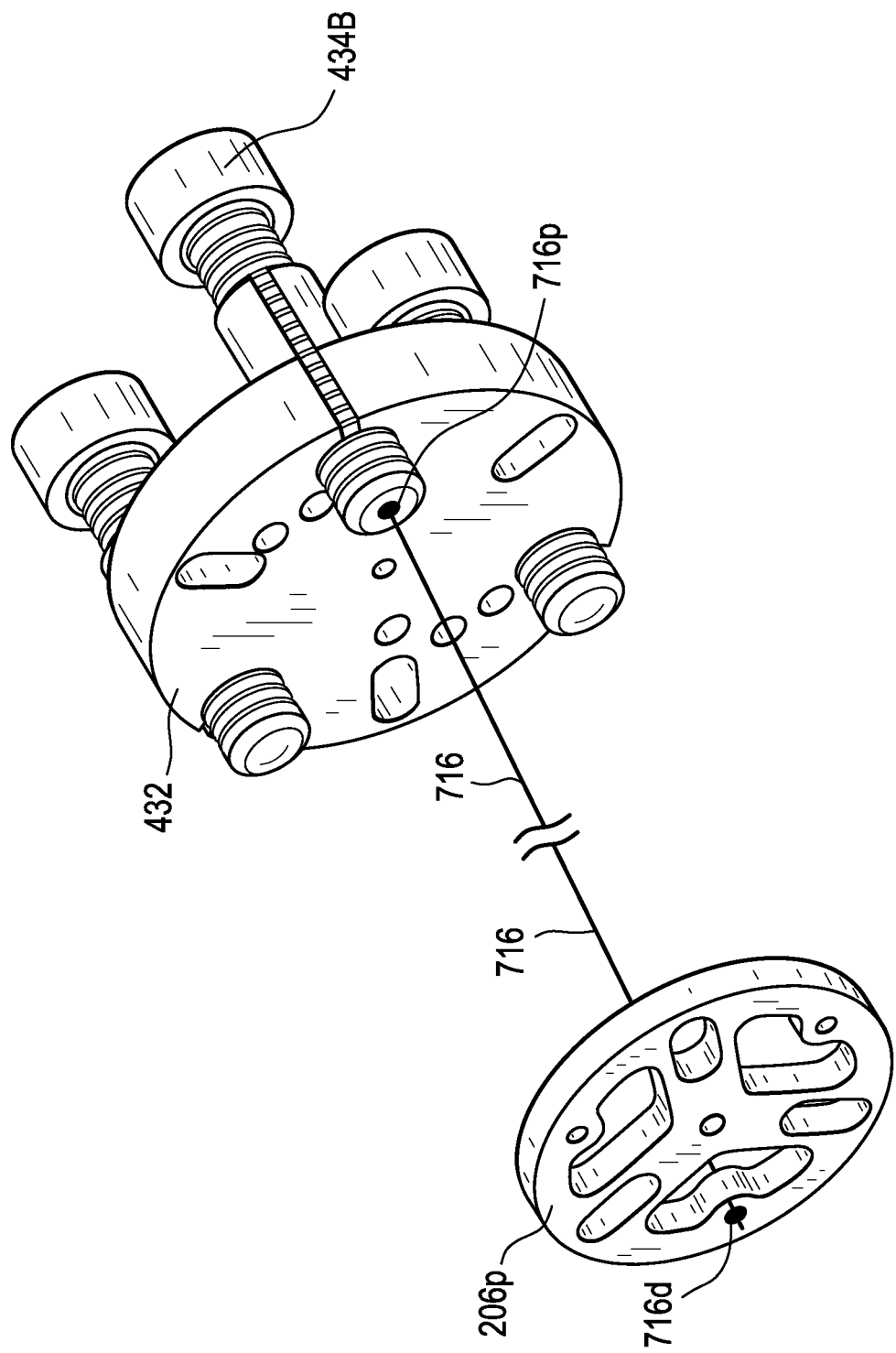
FIG. 21B is a perspective schematic view of the path of a second elbow cable.

The second elbow cable 716 is shown in FIG. 21B. As shown, the terminal distal end 716d of the cable 716 is coupled to a second attachment point on the proximal elbow plate 206p of the distal elbow assembly 200. The terminal proximal end 716p of the cable 716 is coupled to a second attachment point on the tension plate 432 (e.g., a second tension screw 434B). Again, the second attachment point on the proximal elbow plate 206p is rotationally offset 180 degrees from the second attachment point on the tension plate 432.

The third elbow cable 718 is shown in FIG.21C. As shown, the terminal distal end 718d of the cable 718 is coupled to a third attachment point on the proximal elbow plate 206p of the distal elbow assembly 200. The terminal proximal end 718p of the cable is coupled to a third attachment point on the tension plate 432 (e.g., a third tension screw 434C). Again, the third attachment point on the proximal elbow plate 206p is rotationally offset 180 degrees from the third attachment point on the tension plate 432.

The three attachment points on the proximal elbow plate 206p are spaced 120 degrees apart from one another about the circumference of the plate, as are the three attachment points on the tension plate 432. The proximal elbow plate 206p is positioned such that it is rotated approximately 60 degrees relative to the tension plate 432. Accordingly, the cables 714, 716, 718 are coupled to proximal and distal attachment points that are offset 180 degrees from one another. This 180 degree rotational offset in attachment points causes the elbow cables to "cross over" as they extend through the body assembly 300 and other intervening components of the device 10. This crossing of attachment points produces mirrored motion between the distal elbow assembly 200 and the proximal elbow assembly 400, which in turn produces mimicked translational motion between the end effector assembly 108 and the handle assembly 600.

FIG.22 schematically illustrates the cable interconnection between the proximal and distal elbow assemblies 200, 400. For clarity of illustration, the proximal retainer housing 202p of the distal elbow assembly 200 and the distal retainer housing 402d of the proximal elbow assembly 400 are shown in phantom. In addition, the proximal and distal elbow assemblies 200, 400 are shown in close proximity to one another, even though in fact they can be separated in the longitudinal direction by the body assembly 300 and other intervening components of the device 10, as described above. As shown, when the handle assembly 600 is translated downwards (e.g., a downward heave motion), the proximal retainer housing 402p of the proximal elbow assembly 400 moves laterally relative to the distal retainer housing 402d of the proximal elbow assembly 400. This causes the cone rods 410 to pivot in the concavities in which they are received, such that the cone rods tilt relative to the proximal and distal retainer housings 402p, 402d. The tension plate 432 tilts with the cone rods, which pulls on the second and third cables 716, 718 while simultaneously releasing the first cable 714.

The pulling of the second and third cables 716, 718 causes the lower portion of the proximal elbow plate 206p of the distal elbow assembly 200 to tilt towards the proximal retainer housing 202p of the distal elbow assembly 200. Meanwhile, the releasing of the first cable 714 allows the upper portion of the proximal elbow plate 206p to tilt away from the proximal retainer housing 202p. Accordingly, the proximal elbow plate 206p tilts relative to the proximal retainer housing 202p, causing the cone rods 210 to tilt in a similar fashion. This causes the distal retainer housing 202d to translate downwards, such that the distal elbow assembly 200 minors the proximal elbow assembly 400 and mimicked downward heave is achieved. Thus, the mirrored relationship between the proximal and distal elbow assemblies allows for heave and sway of the proximal retainer housing 402p to be mimicked by heave and sway of the distal retainer housing 202d.

Other Features

Some cables can be prone to stretching or contracting over time or when tension is applied thereto. This can introduce movement error into the system, particularly when cables extend over a long distance. Accordingly, one or more of the wrist cables and/or elbow cables can include an anti-stretch bracing, as shown in FIG.23. The anti-stretch bracing 720 can be in the form of a stretch-resistant member 722 that is fixedly attached to a cable C at least two points 724, 726. For example, a rigid tube through which the cable is passed can be crimped at its proximal and distal ends to first and second points along the length of the cable. Since the rigid tube does not stretch or contract substantially, the cable is prevented from stretching or contracting between the first and second points. Any length of any cable of the device 10 can include an anti-stretch bracing. In one embodiment, all of the wrist cables and all of the elbow cables include an anti-stretch bracing along substantially the entire portion of the cable that extends through the body assembly 300.

Figure 24:
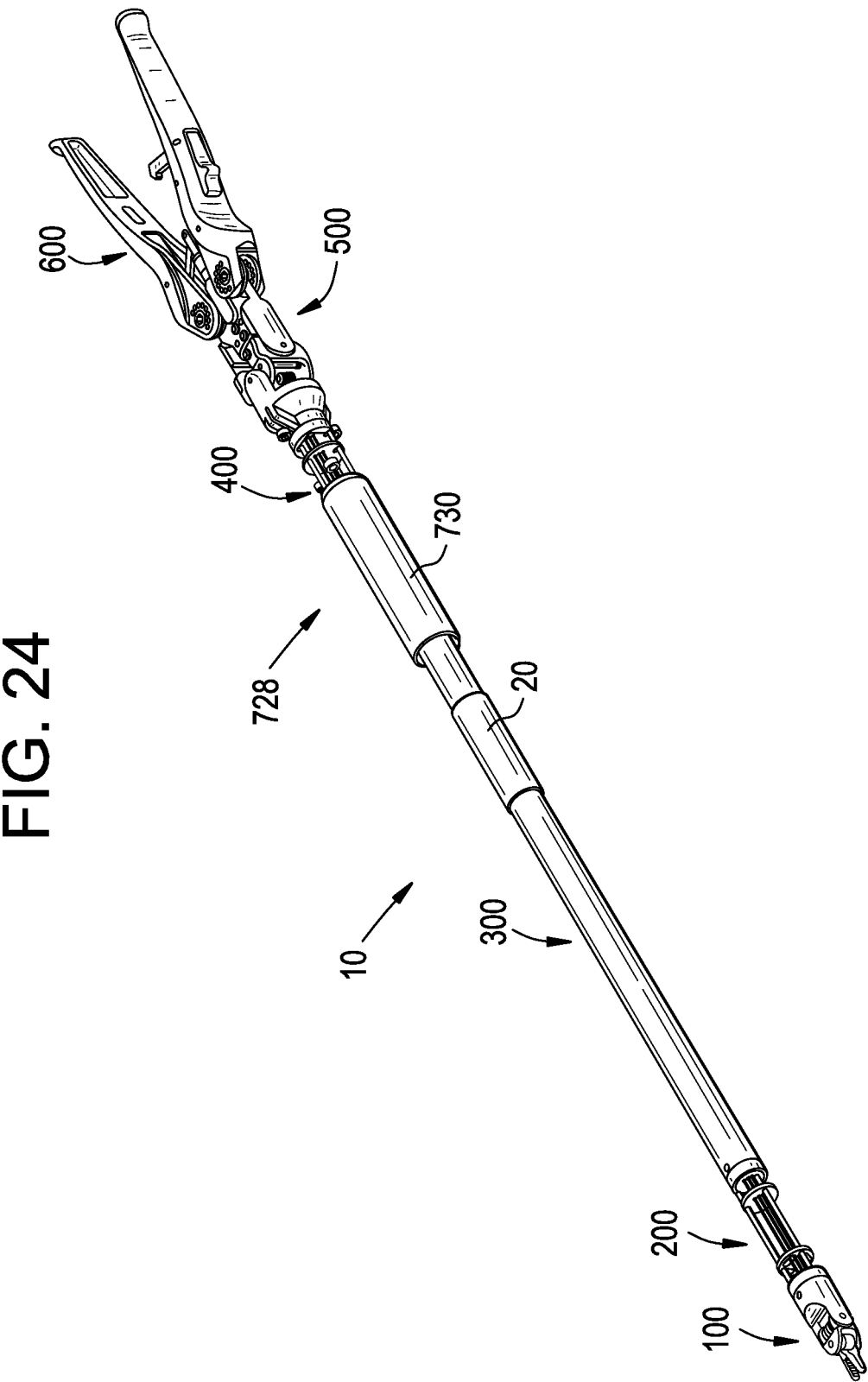
FIG. 24 is a perspective view of the surgical device of FIG. 2A, shown with a locking mechanism.

As shown in FIG.24, the device 10 can also include one or more locking mechanisms. In the illustrated embodiment, the locking mechanism 728 is in the form of a rigid tubular housing 730 slidably disposed over the body assembly 300 and proximal elbow assembly 400. When the locking mechanism 728 is placed in a "locked" position, as shown in FIG.24, the tubular housing 730 can maintain the tension plate 432 of the proximal elbow assembly 400 in a position that is parallel to the distal retainer housing 402d of the proximal elbow assembly 400. This locks the proximal elbow assembly 400 and prevents up-down translational movement (heave) and left-right translational movement (sway) of the handle assembly 600 relative to the body assembly 300. The locking mechanism 728 can also be slid distally along the body assembly 300 to an "unlocked" position, in which the tension plate 432 and the rest of the proximal elbow assembly 400 are positioned outside of the tubular housing 730. In this position, the proximal elbow assembly 400 can be free to move such that heave and sway of the handle assembly 600 is permitted. The locking mechanism 728 can be coupled to the body assembly 300 so as to limit its range of longitudinal motion, and can include one or more biasing springs or other elements to bias it towards either the locked or unlocked configuration.

The device 10 can also include a mechanism for locking the proximal wrist assembly 500 (e.g., a second tubular housing that can slide over one or more of the distal, central, and proximal wrist frames 502, 504, 506, maintaining them in longitudinal alignment). While the illustrated locking mechanism 728 includes a tubular housing 730, other locking mechanisms can also be employed, such as locking pins, straps, screws, or cables. Such locking mechanisms can be configured to lock the various joints of the device 10 in a non-articulated position, in a fully-articulated position, and/or in any intermediate position therebetween.

The inclusion of one or more locking mechanisms can allow the device to function in a plurality of different "modes" of operation, in which various degrees of freedom are restricted. Some users are more comfortable with a rigid tool like a traditional laparoscopic tool and/or do not need several degrees of freedom for certain procedures or for certain aspects of procedures. Thus, for these users, the locking mechanism can be selectively engaged to limit the degrees of freedom in which the end effector assembly can be moved. When extra degrees of freedom are desired or necessary (e.g., during a knot tying or suturing operation), the locking mechanism can be disengaged to restore complete freedom of movement. It will also be appreciated that, if surge and roll capabilities are not required, the body assembly 300 can be coupled directly to the frame 22 without the linear bearing 20, thereby eliminating these degrees of freedom. This ability to change operating modes on the fly prevents the user from having to change tools in the middle of a procedure.

It will thus be appreciated that one or more locking mechanisms can be provided to allow the device 10 to be locked in any of a variety configurations. One exemplary configuration is a "hook" configuration in which the wrist joint is locked in an articulated position, the jaws are locked in a closed position, and the elbow assembly is locked in a non-articulated position. The hook configuration can be useful for performing tissue dissection and for "hooking" and pulling tissue during dissection. Another exemplary operating mode is a "right angle" configuration, which is the same as the hook configuration except that the jaws are not locked. The right angle configuration can be useful for spreading or dissecting tissue that is "behind" an important structure such as a vessel or cystic duct. Selectively locking or unlocking the elbow joint in either of these configurations can allow for a hook or right angle configuration that is customized to the specific anatomy or task at hand. This is also useful for single site surgery to reduce instrument clashing and increase triangulation. Another exemplary configuration is a "wristed straight stick" configuration in which the elbow joint is locked and the jaws and wrist joint remain unlocked. This configuration can provide increased ability to grasp and dissect at different angles compared to non-wristed straight stick. A variation on this configuration is one in which the wrist joint is partially locked (e.g., such that yaw movement of the wrist joint is allowed while pitch movement is prevented, or such that pitch movement of the wrist joint is allowed while yaw movement is prevented).

Although mimicked motion is obtained in the illustrated embodiments, mirrored motion or some combination of the two can also be achieved by reversing the direction in which cables are wound around pulleys, reversing the mapping of cables to handle pulleys, running the elbow cables straight through the device instead of crossing them, etc.

In some embodiments, it can be desirable to scale motion and/or actuation of the device.

A movement ratio can be defined as the ratio of the magnitude of master component movement to the magnitude of slave component movement. In other words, a movement ratio of 5:1 would mean that a 5 mm movement of the master component would be necessary to achieve a 1 mm movement of the slave component. Large movement ratios can advantageously absorb small movements, insulating the slave component from slight tremors or shaking introduced at the master component. Small movement ratios can advantageously reduce surgeon fatigue by minimizing the degree to which they must move the master component. In addition, movement ratios that are less than 1:1 (e.g., 0.5:1) can achieve motion beyond the angulation limits of the human wrist without requiring complex clutching mechanisms. In other words, a 1 mm movement of the master component can be scaled to a greater than 1 mm movement at the slave component to effectively increase the angulation range of a human user.

An actuation ratio can be defined as the ratio of the magnitude of actuation applied to the master component to the magnitude of actuation experienced at the slave component. A high actuation ratio can allow for more precise actuation control at the slave component, whereas a low actuation ratio can reduce surgeon fatigue by limiting the actuation input required at the master component.

Because the pivot axis of the handle levers 602A, 602B (which control actuation) and the yaw pivot axis of the proximal wrist assembly 500 (which controls movement) are offset from one another, the movement ratio and the actuation ratio of the device 10 can be adjusted independently of one another. For example, the diameter of the handle pulleys 620A, 620B, 624A, 624B can be decreased to obtain a higher actuation ratio without affecting the movement ratio. Similarly, the diameter of the pulleys in the central pulley system 508 can be decreased to obtain a higher movement ratio without affecting the actuation ratio.

Progressive scaling can also be achieved by forming an eccentric portion on the circumference of the pulleys (e.g., such that the pulleys have the shape of a cam lobe). This can allow for an initial movement ratio or actuation ratio that increases or decreases as the pulley rotates (i.e., as the cable is wrapped over the eccentric portion).

Figure 25A:
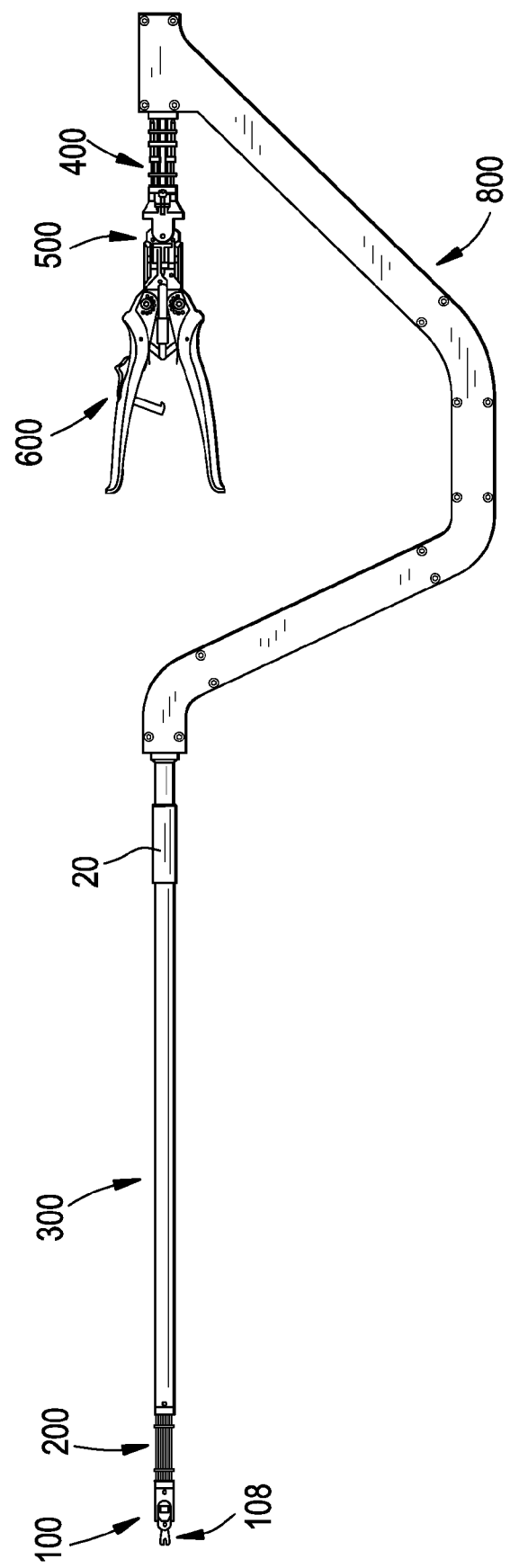
FIG. 25A is a side view of the surgical device of FIG. 2A, shown with a frame assembly.
Figure 25B:
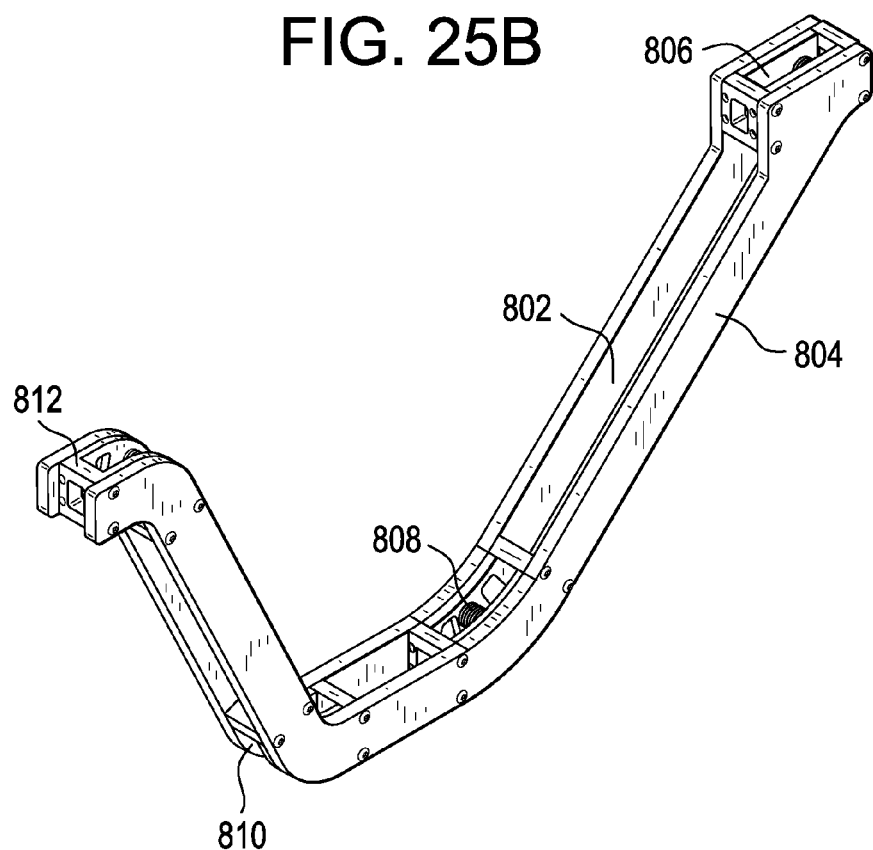
FIG. 25B is a perspective view of the frame assembly of FIG. 25A.
Figure 25C:
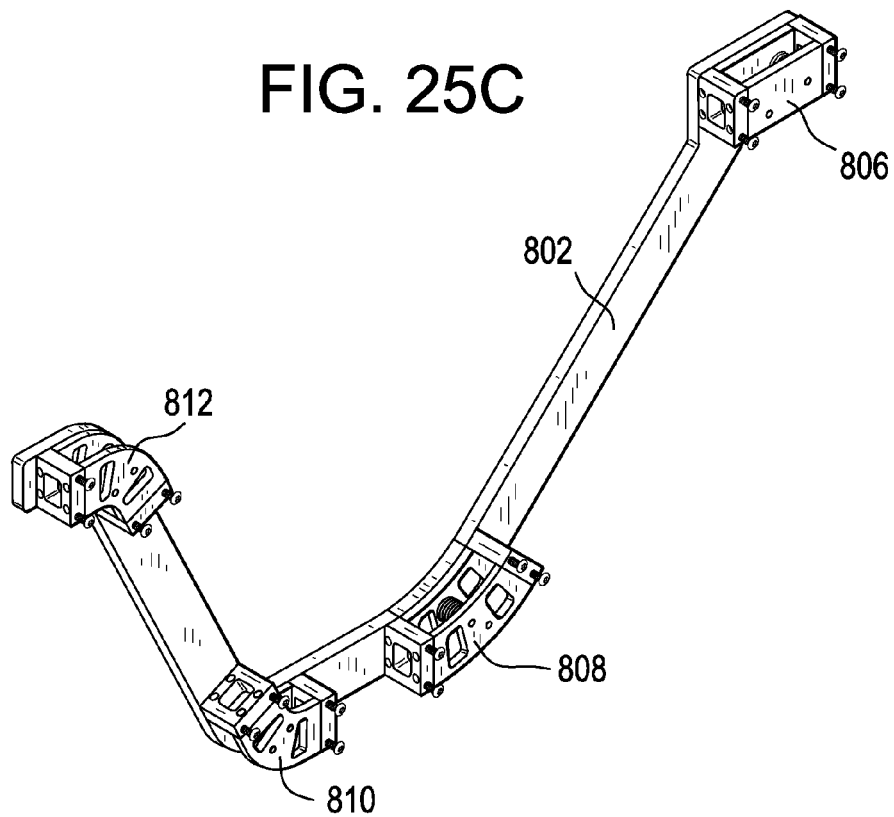
FIG. 25C is a perspective view of the frame assembly of FIG. 25A with one C-shaped side plate removed.

The device 10 can also include a frame assembly 800, as shown in FIGS. 25A-25C. The frame assembly 800 can be positioned between the body assembly 300 and the proximal elbow assembly 400 such that the proximal elbow assembly 400, proximal wrist assembly 500, and handle assembly 600 can be flipped 180 degrees in the proximal-distal direction relative to the body assembly 300. The frame assembly 800 can include first and second C-shaped side plates 802, 804 and a plurality of pulley housings 806, 808, 810, 812 sandwiched therebetween. Each pulley housing 806, 808, 810, 812 can include one or more pulleys mounted to one or more pulley axles for routing the wrist cables 702, 704, 706, 708, 710, 712 and elbow cables 714, 716, 718 through the frame assembly 800 from the proximal elbow assembly 400 to the body assembly 300.

The frame assembly 800 can act as a handle for providing the fixed frame of reference, such that the device 10 can operate with six degrees of freedom even without being coupled to the linear bearing 20 and/or stationary frame 22.

Also, without the frame assembly 800, the movement of the distal "tethered" end of handle assembly 600 is mimicked by the distal "free" end of the end effector assembly 108. With the frame assembly 800, movement of the formerly-proximal "free" end of the handle assembly 600 is mimicked by the distal "free" end of the end effector 108 assembly, which some users might find to be more natural. To obtain this mimicked motion when the frame assembly 800 is included, the wrist cable routing can be swapped at one end of the device 10. For example, the first wrist cable 702 can be routed through the proximal wrist assembly 500 following the path usually followed by the second wrist cable 704, while the second wrist cable 704 can be routed through the proximal wrist assembly 200 following the path usually followed by the first wrist cable 702. The third wrist cable 706 can be similarly swapped with the sixth wrist cable 712 and the fourth wrist cable 708 can be similarly swapped with the fifth wrist cable 710.

As will be appreciated by those skilled in the art, any and all of the embodiments disclosed herein can be interchangeable with one another as needed. In addition, the devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
    an elongate body having proximal and distal ends and a longitudinal axis;
    a master assembly coupled to the proximal end of the elongate body, the master assembly including a handle;
    a slave assembly coupled to the distal end of the elongate body, the slave assembly including an end effector;
    wherein heave and sway of the handle relative to the longitudinal axis of the elongate body causes corresponding heave and sway of the end effector relative to the longitudinal axis of the elongate body;
    wherein the master assembly is coupled to the elongate body by a proximal elbow joint and the slave assembly is coupled to the elongate body by a distal elbow joint;
    wherein the proximal elbow joint is configured to allow for heaving and swaying of the handle relative to the elongate body without allowing for pitching and yawing of the handle relative to the elongate body at the proximal elbow joint; and
    wherein the distal elbow joint is configured to allow for heaving and swaying of the end effector relative to the elongate body without allowing for pitching and yawing of the end effector relative to the elongate body at the distal elbow joint.

2. The device of claim 1, wherein the proximal and distal elbow joints are coupled to one another by a plurality of cables.

3. The device of claim 1, further comprising at least one mechanical linkage extending between the master assembly and the slave assembly.

4. The device of claim 1, wherein the corresponding heave and sway of the slave component is scaled in magnitude relative to the heave and sway of the master component.

5. The device of claim 1, wherein the heave and sway of the master component is mimicked by the corresponding heave and sway of the slave component.

6. The device of claim 1, wherein the heave and sway of the master component is mirrored by the corresponding heave and sway of the slave component.

7. The device of claim 1, wherein actuation of the master assembly causes corresponding actuation of the slave assembly.

8. The device of claim 1, further comprising a linear bearing in which the elongate body is slidably and rotatably received such that the elongate body can surge and roll with respect to the linear bearing.

9. The device of claim 1, further comprising a locking member slidable along the elongate body between a first position in which heave and sway of the master assembly is restrained by the locking member and a second position in which heave and sway of the master assembly is not restrained by the locking member.

10. The device of claim 1, wherein yaw of the handle pulls at least one of a plurality of yaw cables to cause corresponding yaw of the end effector, pitch of the handle pulls at least one of a plurality of pitch cables to cause corresponding pitch of the end effector, and heave and sway of the handle pulls at least one of a plurality of elbow cables to cause corresponding heave and sway of the end effector.

11. The device of claim 10, wherein the master assembly includes a central pulley system comprising a first pulley axle and a second pulley axle, the second pulley axle being perpendicularly oriented relative to the first pulley axle.

12. The device of claim 11, wherein each of the plurality of yaw cables wrap around one pulley disposed on the first pulley axle and one pulley disposed on the second pulley axle.

13. The device of claim 11, wherein each of the plurality of pitch cables wrap around two pulleys disposed on the first pulley axle and two pulleys disposed on the second pulley axle.

14. The device of claim 11, wherein pulleys on the first and second pulley axles around which the yaw cables are wrapped have a diameter that is approximately two times greater than a diameter of pulleys on the first and second pulley axles around which the pitch cables are wrapped.

15. The device of claim 11, wherein the central pulley system comprises a plurality of pulleys, each of the plurality of pulleys having first and second cable tracks extending circumferentially therearound.

16. The device of claim 11, wherein each of the plurality of yaw cables and each of the plurality of pitch cables are wrapped at least 225 degrees around at least one pulley of the central pulley system.

17. A surgical device, comprising:
    an end effector having proximal and distal ends;
    a distal wrist assembly coupled to the proximal end of the end effector, the distal wrist assembly having a first pivot joint about which the end effector yaws and a second pivot joint about which the end effector pitches;
    a distal elbow assembly coupled to a proximal end of the distal wrist assembly, the distal elbow assembly having a first elbow joint about which the distal wrist assembly heaves and sways;
    a handle assembly having proximal and distal ends and first and second handle levers;
    a proximal wrist assembly coupled to the distal end of the handle assembly, the proximal wrist assembly having a third pivot joint about which the handle assembly yaws and a fourth pivot joint about which the handle assembly pitches;
    a proximal elbow assembly coupled to a distal end of the proximal wrist assembly, the proximal elbow assembly having a second elbow joint about which the proximal wrist assembly heaves and sways;
    an elongate body disposed between the proximal and distal elbow assemblies;

a plurality of yaw cables extending from the handle assembly to the end effector;
a plurality of pitch cables extending from the proximal wrist assembly to the distal wrist assembly; and
a plurality of elbow cables extending from the proximal elbow assembly to the distal elbow assembly;
wherein yaw of the handle assembly pulls at least one of the yaw cables to cause corresponding yaw of the end effector, pitch of the handle assembly pulls at least one of the pitch cables to cause corresponding pitch of the end effector, and heave and sway of the handle assembly pulls at least one of the elbow cables to cause corresponding heave and sway of the end effector;
wherein the distal wrist assembly heaves and sways while maintaining the pitch and yaw orientation of the end effector relative to the elongate body; and
wherein the proximal wrist assembly heaves and sways whilemaintainingthe pitch and yaw orientation of the master component relative to the elongate body.

18. The device of claim 17, wherein the yaw of the handle assembly is mimicked by the corresponding yaw of the end effector.

19. The device of claim 17, wherein the yaw of the handle assembly is mirrored by the corresponding yaw of the end effector.

20. The device of claim 17, wherein the corresponding yaw of the end effector is scaled in magnitude relative to the yaw of the handle assembly.

21. The device of claim 17, wherein the pitch of the handle assembly is mimicked by the corresponding pitch of the end effector.

22. The device of claim 17, wherein the pitch of the handle assembly is mirrored by the corresponding pitch of the end effector.

23. The device of claim 17, wherein the corresponding pitch of the end effector is scaled in magnitude relative to the pitch of the handle assembly.

24. The device of claim 17, wherein the heave and sway of the handle assembly are mimicked by the corresponding heave and sway of the end effector.

25. The device of claim 17, wherein the heave and sway of the handle assembly are mirrored by the corresponding heave and sway of the end effector.

26. The device of claim 17, wherein movement of the first and second handle levers towards one another pulls at least one of the yaw cables to cause corresponding movement of first and second jaws of the end effector towards one another.

27. The device of claim 17, wherein the first and second handle levers pivot about at least one handle axis, the at least one handle axis being offset from a pivot axis of the third pivot joint and a pivot axis of the fourth pivot joint.

28. The device of claim 17, further comprising a linear bearing in which the elongate body is slidably and rotatably received such that the elongate body can surge and roll with respect to the linear bearing.

29. The device of claim 17, wherein each of the plurality of elbow cables includes a first end coupled to a first attachment point within the proximal elbow assembly and a second end coupled to a second attachment point within the distal elbow assembly, the first and second attachment points being offset 180 degrees from one another.

30. The device of claim 17, further comprising a locking member slidable along the elongate body between a first position in which movement of the proximal elbow assembly is restrained by the locking member and a second position in which movement of the proximal elbow assembly is not restrained by the locking member.

31. The device of claim 17, wherein the proximal wrist assembly comprises a central pulley system having a first pulley axle and a second pulley axle, the second pulley axle being perpendicularly oriented relative to the first pulley axle.

32. The device of claim 31, wherein each of the plurality of yaw cables wrap around one pulley disposed on the first pulley axle and one pulley disposed on the second pulley axle.

33. The device of claim 31, wherein each of the plurality of pitch cables wrap around two pulleys disposed on the first pulley axle and two pulleys disposed on the second pulley axle.

34. The device of claim 31, wherein pulleys on the first and second pulley axles around which the yaw cables are wrapped have a diameter that is approximately two times greater than a diameter of pulleys on the first and second pulley axles around which the pitch cables are wrapped.

35. The device of claim 31, wherein the central pulley system comprises a plurality of pulleys, each of the plurality of pulleys having first and second cable tracks extending circumferentially therearound.

36. The device of claim 31, wherein each of the plurality of yaw cables and each of the plurality of pitch cables are wrapped at least 225 degrees around at least one pulley of the central pulley system.

37. The device of claim 17, wherein the handle assembly comprises a plurality of handle pulleys, each of the plurality of handle pulleys having a terminal end of a respective yaw cable fixedly attached thereto.

38. A surgical device, comprising:
an end effector having proximal and distal ends;
a distal wrist assembly coupled to the proximal end of the end effector, the distal wrist assembly having a first pivot joint about which the end effector yaws and a second pivot joint about which the end effector pitches;
a distal elbow assembly coupled to a proximal end of the distal wrist assembly, the distal elbow assembly having a first elbow joint about which the distal wrist assembly heaves and sways;
a handle assembly having proximal and distal ends and first and second handle levers;
a proximal wrist assembly coupled to the distal end of the handle assembly, the proximal wrist assembly having a third pivot joint about which the handle assembly yaws and a fourth pivot joint about which the handle assembly pitches;
a proximal elbow assembly coupled to a distal end of the proximal wrist assembly, the proximal elbow assembly having a second elbow joint about which the proximal wrist assembly heaves and sways;
an elongate body disposed between the proximal and distal elbow assemblies;
a plurality of yaw cables extending from the handle assembly to the end effector;
a plurality of pitch cables extending from the proximal wrist assembly to the distal wrist assembly;
a plurality of elbow cables extending from the proximal elbow assembly to the distal elbow assembly; and
a frame assembly that couples the elongate body to the proximal elbow assembly, the frame assembly comprising a plurality of pulleys for guiding the plurality of yaw cables, the plurality of pitch cables, and the plurality of elbow cables therethrough;
wherein yaw of the handle assembly pulls at least one of the yaw cables to cause corresponding yaw of the end effector, pitch of the handle assembly pulls at least one of the pitch cables to cause corresponding pitch of the end effector, and heave and sway of the handle assembly pulls at least one of the elbow cables to cause corresponding heave and sway of the end effector.

39. A surgical device, comprising:
an end effector having proximal and distal ends;
a distal wrist assembly coupled to the proximal end of the end effector, the distal wrist assembly having a first pivot joint about which the end effector yaws and a second pivot joint about which the end effector pitches;
a distal elbow assembly coupled to a proximal end of the distal wrist assembly, the distal elbow assembly having a first elbow joint about which the distal wrist assembly heaves and sways;
a handle assembly having proximal and distal ends and first and second handle levers;
a proximal wrist assembly coupled to the distal end of the handle assembly, the proximal wrist assembly having a third pivot joint about which the handle assembly yaws and a fourth pivot joint about which the handle assembly pitches;
a proximal elbow assembly coupled to a distal end of the proximal wrist assembly, the proximal elbow assembly having a second elbow joint about which the proximal wrist assembly heaves and sways;
an elongate body disposed between the proximal and distal elbow assemblies;
a plurality of yaw cables extending from the handle assembly to the end effector;
a plurality of pitch cables extending from the proximal wrist assembly to the distal wrist assembly; and
a plurality of elbow cables extending from the proximal elbow assembly to the distal elbow assembly;
wherein yaw of the handle assembly pulls at least one of the yaw cables to cause corresponding yaw of the end effector, pitch of the handle assembly pulls at least one of the pitch cables to cause corresponding pitch of the end effector, and heave and sway of the handle assembly pulls at least one of the elbow cables to cause corresponding heave and sway of the end effector, and
wherein each of the plurality of elbow cables is coupled to a corresponding tension adjustment screw threadably received in a tension plate of the proximal elbow assembly.

40. A surgical device, comprising:
an end effector having proximal and distal ends;
a distal wrist assembly coupled to the proximal end of the end effector, the distal wrist assembly having a first pivot joint about which the end effector yaws and a second pivot joint about which the end effector pitches;
a distal elbow assembly coupled to a proximal end of the distal wrist assembly, the distal elbow assembly having a first elbow joint about which the distal wrist assembly heaves and sways
a handle assembly having proximal and distal ends and first and second handle levers;
a proximal wrist assembly coupled to the distal end of the handle assembly, the proximal wrist assembly having a third pivot joint about which the handle assembly yaws and a fourth pivot joint about which the handle assembly pitches;
a proximal elbow assembly coupled to a distal end of the proximal wrist assembly, the proximal elbow assembly having a second elbow joint about which the proximal wrist assembly heaves and sways
an elongate body disposed between the proximal and distal elbow assemblies;
a plurality of yaw cables extendin from the handle assembly to the end effector;
a plurality of pitch cables extending from the proximal wrist assembly to the distal wrist assembly;
a plurality of elbow cables extending from the proximal elbow assembly to the distal elbow assembly; and
a plurality of cable braces, each of the plurality of cable braces being coupled to a respective one of the plurality of elbow cables at two or more points, each of the plurality of braces being less susceptible to stretching than the plurality of elbow cables;
wherein yaw of the handle assembly pulls at least one of the yaw cables to cause corresponding yaw of the end effector, pitch of the handle assembi pulls at least one of the pitch cables to cause corresponding pitch of the end effector, and heave and sway of the handle assembly pulls at least one of the elbow cables to cause corresponding heave and sway of the end effector.

* * * * *